United States Patent
Gravestock et al.

(10) Patent No.: US 7,141,583 B2
(45) Date of Patent: Nov. 28, 2006

(54) OXAZOLIDINONE DERIVATIVES WITH ANTIBIOTIC ACTIVITY

(75) Inventors: Michael Barry Gravestock, Waltham, MA (US); Michael John Betts, Macclesfield (GB); Ian Richard Matthews, Haselmere (GB); David Alan Griffin, Haselmere (GB)

(73) Assignee: AstraZeneca AB, Södertälje (SE)

( * ) Notice: Subject to any disclaimer, the term of this patent is extended or adjusted under 35 U.S.C. 154(b) by 293 days.

(21) Appl. No.: 10/258,355

(22) PCT Filed: Apr. 23, 2001

(86) PCT No.: PCT/GB01/01815

§ 371 (c)(1), (2), (4) Date: May 6, 2003

(87) PCT Pub. No.: WO01/81350

PCT Pub. Date: Nov. 1, 2001

(65) Prior Publication Data

US 2003/0216373 A1    Nov. 20, 2003

(30) Foreign Application Priority Data

Apr. 25, 2000  (GB) ................. 0009803.8

(51) Int. Cl.
*A61K 31/4439* (2006.01)
*A61K 31/454* (2006.01)
*C07D 401/14* (2006.01)

(52) U.S. Cl. ............. 514/326; 514/340; 546/210; 546/271.4

(58) Field of Classification Search ............. 514/326, 514/340; 546/210, 271.4
See application file for complete search history.

(56) References Cited

U.S. PATENT DOCUMENTS

| | | |
|---|---|---|
| 4,150,029 A | 4/1979 | Dostert et al. |
| 4,287,351 A | 9/1981 | Bourgery et al. |
| 4,340,606 A | 7/1982 | Fugitt et al. |
| 4,372,967 A | 2/1983 | Langlois et al. |
| 4,476,136 A | 10/1984 | Dostert et al. |
| 4,705,799 A | 11/1987 | Gregory |
| 4,851,423 A | 7/1989 | Girijavallabhan et al. |
| 4,942,183 A | 7/1990 | Gregory et al. |
| 4,948,801 A | 8/1990 | Carlson et al. |
| 4,977,173 A | 12/1990 | Brittelli et al. |
| 5,164,510 A | 11/1992 | Brickner |
| 5,182,403 A | 1/1993 | Brickner |
| 5,225,565 A | 7/1993 | Brickner |
| 5,231,188 A | 7/1993 | Brickner |
| 5,247,090 A | 9/1993 | Brickner |
| 5,272,167 A | 12/1993 | Girijavallabhan et al. |
| 5,459,144 A | 10/1995 | Girijavallabhan et al. |
| 5,480,899 A | 1/1996 | Yano et al. |
| 5,521,202 A | 5/1996 | Yano et al. |
| 5,523,403 A | 6/1996 | Barbachyn |
| 5,529,998 A | 6/1996 | Habich et al. |

(Continued)

FOREIGN PATENT DOCUMENTS

DE    199 01 306    7/2000

(Continued)

OTHER PUBLICATIONS 1995-2002 ICAAC (Interscience Congress of Antimicrobial Agents and Chemotherapy) conference abstracts.

(Continued)

*Primary Examiner*—Kamal A. Saeed
*Assistant Examiner*—Rebecca Anderson

(57) ABSTRACT

Compounds of the formula (I), or a pharmaceutically acceptable salt, or an in-vivo-hydrolysable ester thereof,

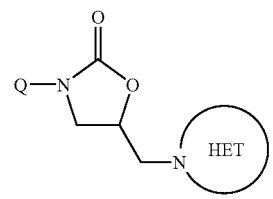
(I)

wherein HET is an N-linked 5-membered heteroaryl ring, optionally substituted on a C atom by an oxo or thioxo group; and/or by 1 or 2 (1–4C) alkyl groups; and/or on an available nitrogen atom by (1–4C)alkyl; or HET is an N-linked 6-membered heteroaryl ring containing up to three nitrogen heteroatoms in total, optionally substituted on a C atom as above; Q is selected from, for example, Q1

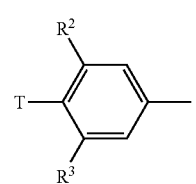

Q1

$R^2$ and $R^3$ are independently hydrogen or fluoro;
T is selected from a range of groups, for example, of formula (TC5)

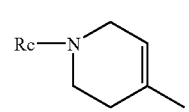

(TC5)

wherein Rc is, for example, $R^{13}CO—$, $R^{13}SO_2—$ or $R^{13}CS—$;
wherein $R^{13}$ is, for example, optionally substituted (1–10C)alkyl or $R^{14}C(O)O(1-6C)alkyl$
wherein $R^{14}$ is optionally substituted (1–10C)alkyl; are useful as antibacterial agents; and processes for their manufacture and pharmaceutical compositions containing them are described.

5 Claims, No Drawings

U.S. PATENT DOCUMENTS

| | | |
|---|---|---|
| 5,532,255 A | 7/1996 | Raddatz et al. |
| 5,547,950 A | 8/1996 | Hutchinson et al. |
| 5,561,148 A | 10/1996 | Gante et al. |
| 5,574,055 A | 11/1996 | Borgulya et al. |
| 5,627,181 A | 5/1997 | Riedl et al. |
| 5,652,238 A | 7/1997 | Brickner et al. |
| 5,668,286 A | 9/1997 | Yamada et al. |
| 5,684,023 A | 11/1997 | Riedl et al. |
| 5,688,792 A | 11/1997 | Barbachyn et al. |
| 5,698,574 A | 12/1997 | Riedl et al. |
| 5,700,799 A | 12/1997 | Hutchinson et al. |
| 5,708,169 A | 1/1998 | Hester, Jr. et al. |
| 5,719,154 A | 2/1998 | Tucker et al. |
| 5,736,545 A | 4/1998 | Gadwood et al. |
| 5,750,532 A | 5/1998 | Girijavallabhan et al. |
| 5,785,976 A | 7/1998 | Westesen et al. |
| 5,792,765 A | 8/1998 | Riedl et al. |
| 5,827,857 A | 10/1998 | Riedl et al. |
| 5,837,870 A | 11/1998 | Pearlman et al. |
| 5,843,967 A | 12/1998 | Riedl et al. |
| 5,861,413 A | 1/1999 | Habich et al. |
| 5,869,659 A | 2/1999 | Stolle et al. |
| 5,880,118 A | 3/1999 | Barbachyn et al. |
| 5,883,093 A | 3/1999 | Hutchinson et al. |
| 5,910,504 A | 6/1999 | Hutchinson |
| 5,922,708 A | 7/1999 | Riedl et al. |
| 5,929,083 A | 7/1999 | Yoon et al. |
| 5,952,324 A | 9/1999 | Barbachyn et al. |
| 5,955,460 A | 9/1999 | Thomas |
| 5,968,962 A | 10/1999 | Thomas et al. |
| 5,981,528 A | 11/1999 | Gravestock |
| 6,028,090 A | 2/2000 | Gante et al. |
| 6,051,716 A | 4/2000 | Hutchinson et al. |
| 6,069,145 A | 5/2000 | Betts |
| 6,069,160 A | 5/2000 | Stolle et al. |
| 6,090,820 A | 7/2000 | Barbachyn et al. |
| 6,107,519 A | 8/2000 | Pearlman |
| 6,110,936 A | 8/2000 | Gravestock |
| 6,124,334 A | 9/2000 | Hutchinson |
| 6,129,940 A | 10/2000 | Leadbeater |
| 6,140,318 A | 10/2000 | Cama et al. |
| 6,194,441 B1 | 2/2001 | Roberts et al. |
| 6,271,388 B1 | 8/2001 | Yaegashi et al. |
| 6,362,191 B1 | 3/2002 | Mills |
| 6,455,529 B1 | 9/2002 | Gante et al. |
| 6,462,056 B1 | 10/2002 | Bottcher et al. |
| 2002/0045625 A1 | 4/2002 | Sciotti et al. |
| 2002/0103186 A1 | 8/2002 | Mehta et al. |

FOREIGN PATENT DOCUMENTS

| | | |
|---|---|---|
| DE | 199 07 701 | 8/2000 |
| DE | 199 09 785 | 9/2000 |
| DE | 100 14 961 | 1/2001 |
| DE | 100 34 624 | 1/2002 |
| DE | 100 34 625 | 1/2002 |
| EP | 0 127 902 | 12/1984 |
| EP | 0 184 170 | 11/1986 |
| EP | 0 359 418 | 3/1990 |
| EP | 0 609 905 | 8/1994 |
| EP | 0 710 657 | 5/1996 |
| EP | 1 029 854 | 8/2000 |
| EP | 1 130 016 | 9/2001 |
| FR | 2 338 268 | 8/1977 |
| FR | 2 458 547 | 1/1981 |
| JP | 07-309850 | 11/1995 |
| JP | 11-322729 | 11/1999 |
| JP | 2000-136186 | 5/2000 |
| WO | WO 93/09103 | 5/1993 |
| WO | WO 93/23384 | 11/1993 |
| WO | WO 94/01110 | 1/1994 |
| WO | WO 97/06791 | 2/1997 |
| WO | WO 97/10223 | 3/1997 |
| WO | WO 97/14690 | 4/1997 |
| WO | WO 97/23212 | 7/1997 |
| WO | WO 97/31917 | 9/1997 |
| WO | WO 98/01446 | 1/1998 |
| WO | WO 98/01447 | 1/1998 |
| WO | WO 98/07708 | 2/1998 |
| WO | WO 98/54161 | 12/1998 |
| WO | WO 99/02525 | 1/1999 |
| WO | WO 99/03846 | 1/1999 |
| WO | WO 99/10342 | 3/1999 |
| WO | WO 99/12914 | 3/1999 |
| WO | WO 99/24428 | 5/1999 |
| WO | WO 99/25344 | 5/1999 |
| WO | WO 99/29688 | 6/1999 |
| WO | WO 99/32175 | 7/1999 |
| WO | WO 99/33839 | 7/1999 |
| WO | WO 99/37630 | 7/1999 |
| WO | WO 99/37641 | 7/1999 |
| WO | WO 99/37652 | 7/1999 |
| WO | WO 99/40094 | 8/1999 |
| WO | WO 99/41244 | 8/1999 |
| WO | WO 99/43671 | 9/1999 |
| WO | WO 99/59616 | 11/1999 |
| WO | WO 99/62504 | 12/1999 |
| WO | WO 99/63937 | 12/1999 |
| WO | WO 99/64416 | 12/1999 |
| WO | WO 99/64417 | 12/1999 |
| WO | WO 00/03710 | 1/2000 |
| WO | WO 00/10566 | 3/2000 |
| WO | WO 00/21960 | 4/2000 |
| WO | WO 00/27816 | 5/2000 |
| WO | WO 00/27817 | 5/2000 |
| WO | WO 00/27827 | 5/2000 |
| WO | WO 00/29396 | 5/2000 |
| WO | WO 00/29409 | 5/2000 |
| WO | WO 00/32599 | 6/2000 |
| WO | WO 00/41473 | 7/2000 |
| WO | WO 00/44741 | 8/2000 |
| WO | WO 00/45177 | 8/2000 |
| WO | WO 00/62783 | 10/2000 |
| WO | WO 00/73301 | 12/2000 |
| WO | WO 01/40222 | 6/2001 |
| WO | WO 01/40236 | 6/2001 |
| WO | WO 01/42229 | 6/2001 |
| WO | WO 01/42242 | 6/2001 |
| WO | WO 01/44212 | 6/2001 |
| WO | WO 01/46164 | 6/2001 |
| WO | WO 01/46185 | 6/2001 |
| WO | WO 01/47919 | 7/2001 |
| WO | WO 01/58885 | 8/2001 |
| WO | WO 01/74812 | 10/2001 |
| WO | WO 01/80841 | 11/2001 |
| WO | WO 01/81350 | 11/2001 |
| WO | WO 01/94342 | 12/2001 |
| WO | WO 01/98297 | 12/2001 |
| WO | WO 02/02095 | 1/2002 |
| WO | WO 02/15940 | 2/2002 |
| WO | WO 02/18354 | 3/2002 |
| WO | WO 02/20515 | 3/2002 |
| WO | WO 02/32459 | 4/2002 |
| WO | WO 02/32857 | 4/2002 |
| WO | WO 02/48139 | 6/2002 |
| WO | WO 02/50040 | 6/2002 |
| WO | WO 02/050061 | 6/2002 |
| WO | WO 02/051819 | 7/2002 |
| WO | WO 02/056013 | 7/2002 |
| WO | WO 02/059115 | 8/2002 |
| WO | WO 02/059116 | 8/2002 |
| WO | WO 02/080841 | 10/2002 |
| WO | WO 02/081468 | 10/2002 |
| WO | WO 02/081469 | 10/2002 |

| | | |
|---|---|---|
| WO | WO 02/081470 | 10/2002 |
| WO | WO 02/096890 | 12/2002 |
| WO | WO 02/096916 | 12/2002 |
| WO | WO 02/096917 | 12/2002 |
| WO | WO 02/096918 | 12/2002 |
| WO | WO 02/102785 | 12/2002 |
| WO | WO 03/000256 | 1/2003 |

OTHER PUBLICATIONS

Ashtekar, D. et al. Oxazolidinones, a New Class of Synthetic Antituberculosis Agent: In vitro and in vivo Activities of Dup-721 Against Mycobacterium tuberculosis. *Diagn. Microbiol. Infect. Dis.* 14, 465-471 (1991).

Barbachyn, M. et al. Synthesis and Antibacterial Activity of New Tropone-Substituted Phenyloxazolidinone Antibacterial Agents. 1. Identification of Leads and Importance of the Tropone Substitution Pattern. *Bioorganic and Medicinal Chem. Letters* 6, 1003-1008 (1996).

Barbachyn, M. et al. Synthesis and Antibacterial Activity of New Tropone-Substituted Phenyloxazolidinone Antibacterial Agents. 2. Modification of the Phenyl Ring—the Potentiating Effect of Fluorine Substitution on In Vivo Activity. *Bioorganic and Medicinal Chem. Letters* 6, 1009-1014 (1996).

Barbachyn, M. et al. Identification of a Novel Oxazolidinone (U-100480) with Potent Antimycobacterial Activity. *J. Med. Chem.* 39, 680-685 (1996).

Barry, A. et al. In Vitro Evaluation of Dup 105 and Dup 721, Two New Oxazolidinone Antimicrobial Agents. *Antimicrobial Agents and Chemotherapy* 32, 150-152 (1988).

Borthwick, A. et al. 5-(Acetamidomethyl)-3-Aryldihydrofuran-2-ones, and 5-(Acetamidomethyl)-3-Aryltetrahydrofuran-2-ones, Two New Classes of Antibacterial Agents. *Med. Chem. Res.* 6, 22-27 (1996).

Brickner, S. et al. Oxazolidinone Antibacterial Agents. *Current Pharmaceutical Design* 2, 194 (1996).

Brickner, S. et al. Synthesis and Antibacterial Activity of U-100592 and U-100766, Two Oxazolidinone Antibacterial Agents for the Potential Treatment of Multidrug-Resistant Gram-Positive Bacterial Infections. *J. Med. Chem.* 39, 673-679 (1996).

Bronson, J.J. and Barrett, J.F. Recent Developments in Antibacterial Research. In Ann. Reports Med. Chem. 36, Section III, Chapter 9, pp. 89-98 (2001).

Brumfitt, W. et al. In-vitro Microbiological Activities of Dup 105 and Dup 721, Novel Synthetic Oxazolidinones. *J. Antimicrobial Chemotherapy* 21, 711-720 (1988).

Brumfitt, W. et al. Variation in Response of Gram-Positive cocci to the Combination Dup 721 and ciprofloxacin. *J. Antimicrob. Chemotherapy* 24, 465-466 (1989).

Brunfitt, W. et al. Antibacterial Oxazolidinones: In Vitro Activity of a New Analogue, E33709. *Diagn. Microbiol. Infect. Dis.* 15, 621-625 (1992).

Clemett, D. and Markham, A. Linezolid. Drugs 59, 815-827 (2000).

Daly, J. et al. Activity and Mechanism of Action of Dup 105 and Dup 721, New Oxazolidinone Compounds. *J. Antimicrobial Chemotherapy* 21, 721-730 (1988).

Denis, A. et al. 5-Aryl-beta, gamma Butenolide, A New Class of Antibacterial Derived from the N-Aryl Oxazolidinone Dup 721. *Bioorganic and Med. Chem. Letters* 4, 1925-1930 (1994).

Diekama, D.J. and Jones, R.N. Oxazolidinones. Drugs 59, 7-16 (2000).

Dostert, P. et al. Structural Modifications in Oxazolidinone Series Leading to Type A or B Selective Monoamine Oxidase Inhibitors. *Int. Congress Series, Excerpta Medica* 564, 197-208 (1982).

Eliopoulos, G. et al. In Vitro Activities of New Oxazolidinone Antimicrobial Agents against Enterococci. *Antimicrobial Agents and Chemotherapy* 3240, 1745-1747 (1996).

Eustice, D. et al. Mechanism of Action of Dup 721: Inhibition of an Early Event during Initiation of Protein Synthesis. *Antimicrobial Agents and Chemotherapy* 32, 1218-1222 (1988).

Eustice, D. et al. The Mechanism of Action of Dup 721, a New Antibacterial Agent: Effects on Macromolecular Synthesis. *Biochem. And Biophys. Res. Comm.* 150, 965-971 (1988).

Eustice, D. et al. An Automated Pulse Labeling Method for Structure-Activity Relationship Studies with Antibacterial Oxazolidinones. *Drugs Exp. Clin. Res.* 16, 149-155 (1990).

Ford, C. et al. In Vivo Activities of U-100592 and U-100766, Novel Oxazolidinone Antimicrobial Agents, against Experimental Bacterial Infections. *Antimicrobial Agents and Chemotherapy* 40, 1508-1513 (1996).

Gadwood, R.C. and Shinabarger, D.A. Progress in the Oxazolidinone Antibacterials. Ann. Report Med. Chem. 35, 135-144 (2000).

Grega, K. et al. Regioselective Metalation of Fluoroanilines. An Application to the Synthesis of Fluorinated Oxazolidinone Antibacterial Agents. *J. Org. Chem.* 60, 5255-5261 (1995).

Gregory, W. et al. Antibacterials. Synthesis and Structure-Activity Studies of 3-Arly-2-Oxazolidinones. 1. The "B" Group. *J. Med. Chem.* 32, 1673-1681 (1989).

Gregory, W. et al. Antibacterials. Synthesis and Structure-Activity Studies of 3-Aryl-2-oxooxazolidines. 2. The "A" Group. *J. Med. Chem.* 33, 2569-2578 (1990).

Jegham, S. & George, P. Monoamine oxidase A and B inhibitors. Exp. Opin. Ther. Patents 8, 1143-1150 (1998).

Jones, R. et al. In Vitro Antimicrobial Activities and Spectra of U-100592 and U-100766, Two Novel Fluorinated Oxazolidinones. *Antimicrobial Agents and Chemotherapy* 40, 720-726 (1996).

Jorgensen, J. et al. In Vitro Activities of the Oxazolidinone Antibodies U-100592 and U-100766 against *Staphylococcus aureus* and Coagulase-Negative Staphylococcus Species. *Antimicrobial Agents and Chemotherapy* 41, 465-467 (Feb. 1997).

Kaatz, G. et al. In Vitro Activities of Oxazolidinone Compounds U100592 and U100766 against *Staphylococcus aureus* and *Staphylococcus epidermis*. *Antimicrobial Agents and Chemotherapy* 40, 799-801 (1996).

Kalgutkar, A.S. et al. Interactions of Nitrogen-Containing Xenobiotics with Monoamine Oxidase (MAO) Isozymes A and B: SAR Studies on MAO Substrates and Inhibitors. Chemical. Res. in Toxicology 14, Section 10.2, p. 1149 (2001).

Lin, A. et al. The Oxazolidinone Eperezolid Binds to the 50S Ribosomal Subunit and Competes with Binding of Chloramphenical and Lincomycin. *Antimicrobial Agents and Chemotherapy* 41, 2127-2131 (1997).

Lizondo, J. et al. Linezolid. *Drugs of the Future* 21, 1116-1123 (1996).

Lund, J. et al. Hypersegmented Megakaryocytes and Megakaryocytes with Multiple Separate Nuclei in Dogs Treated with PNU-100592, an Oxazolidinone Antibiotic. *Toxicologic Pathology* 25, 339-343 (1997).

Maple, P. et al. Comparative in-vitro activity of vancomycin, teicoplanin, ramoplanin (formerly A16686), paldimycin, Dup 721 and Dup 105 against methicillin and gentamicin resistant *Staphylococcus aureus*. *J. Antimicrobial Chemotherapy* 23, 517-525 (1989).

Mason, E. et al. In Vitro Activities of Oxazolidinones U-100592 and U-100766 against Penicillin-Resistant and Cephalosporin-Resistant Strains of *Streptococcus pneumoniae*. *Antimicrobial Agents and Chemotherapy* 40, 1039-1040 (1996).

Mini, E. et al. Comparative in Vitro Activity of the New Oxazolidinones Dup 721 and Dup 105 against Staphylococci and Streptococci. *Eur. J. Clin. Microbiol. Infect. Dis.* 8, 256-260 (1989).

Mulazimoglu, L. et al. In Vitro Activities of Two Novel Oxazolidinones (U100592 and U100766), a New Fluroquinolone (Trovafloxacin), and Dalfopristin-Quinupristin against *Staphylococcus aureus* and *Staphylococcus epidermis*. *Antimicrobial Agents and Chemotherapy* 40, 2428-2430 (1996).

Neu, H. et al. In Vitro Activities of Two Oxazolidinone Antimicrobial Agents, Dup 721 and Dup 105. *Antimicrobial Agents and Chemotherapy* 32, 580-583 (1988).

Park, C. et al, Antibacterials. Synthesis and Structure-Activity Studies of 3-Aryl-2-Oxazolidinones. 4. Multiply-Substituted Aryl Derivatives. *J. Med. Chem.* 35, 1156-1165 (1992).

Patel, U. et al. Oxazolidinones Mechanism of Action: Inhibition of the First Peptide Bond Formation. J. Biol. Chem. 276, 37199-37205 (Oct. 5, 2001).

Phillips, O.A. et al. Synthesis and Antibacterial Activity of 5-Substituted Oxazolidinones. *Bioorganic Med. Chem.* 11 35-41 (2000).

Ranaldi, G. et al. Transport of the Antibacterial Agent Oxazolidin-2-One and Derivatives across Intestinal (Caco-2) and Renal (MDCK) Epithelial Cell Lines. *Antimicrobial Agents and Chemotherapy* 40, 652-658 (1996).

Riedl, B. & Endermann, R. Recent developments with oxazolidinone antibiotics. *Exp. Opin. Ther. Patents* 9, 625-633 (1999).

Schaadt, R. et al. Serum Inhibitory Titers and Serum Bactericidal Titers for Human Subjects Receiving Multiple Doses of the Antibacterial Oxazolidinones Eperezolid and Linezolid. *Diagn. Microbiol. Infect. Dis.* 28, 201-204 (1997).

Schaus, S. et al. Dynamic Kinetic Resolution of Epichlorohydrin via Enantioselective Catalytic Ring Operation with TMSN3. Practical Synthesis of Aryl Oxazolidinone Antibacterial Agents. *Tetrahedron Letters* 37, 7937-7940 (1996).

Scholl, J. et al. Micellar Electrokinetic Chromatography as a Generalized Alternative to High-Performance Liquid Chromatography for Purity Determination of a Class of Investigational Antibacterial Drugs. *J. Chromatography* 695, 147-156 (1997).

Seneci, P. et al. Synthesis and Antimicrobial Activity of Oxazolidin-2-ones and Related Heterocycles. *J. Chem. Soc. Perkin Trans.* 1, 16, 2345-2351 (1994).

Shinabarger, D. et al. Mechanism of Action of Oxazolidinones: Effects of Linezolid and Eperezolid on Translation Reactions. *Antimicrobial Agents and Chemotherapy* 41, 2132-2136 (1997).

Silverman, R. et al. The Oxazolidinone Antibacterial Agent DuP 105 Does Not Act on Cell Wall Biosynthesis or on a Beta-Lactamase. *Biochemical and Biophys. Res. Comm.* 195, 1077-1080 (1993).

Slee, A. et al. Oxazolidinones, a New Class of Synthetic Antibacterial Agents: In Vitro and In Vivo Activities of DuP 105 and DuP 721. *Antimicrobial Agents and Chemotherapy* 31, 1791-1797 (1987).

Spangler, S. et al. Activities of RPR 106972 (a New Oral Streptogramin), Cefditoren (a New Oral Cephalosporin), Two New Oxazolidinones (U-100592 and U-100766), and Other Oral and Parenteral Agents against 203 Penicillin-Susceptible and -Resistant Pneumococci. *Antimicrobial Agents and Chemotherapy* 40, 481-484 (1996).

Takagi, H. et al. Safety Pharmacology Evaluation of the Oxazolidinone, U-100766. *Society of Toxicologists Annual Meeting*—Abstract 564, (1996).

Tucker, J. A. et al. Piperazinyl Oxazolidinone Antibacterial Agents Containing a Pyridine, Diazene, or Triazene Heteroaromatic Ring. *J. Med. Chem.* 41, 3727-2735 (1998).

Wang, C. et al. Chiral Synthesis fo DuP 721, a New Antibacterial Agent. *Tetrahedron* 45, 1323-1326 (1989).

Worth, S. et al. Quality Control Guidelines for Amoxicillin, Amoxicillin-Clavulanate, Azithromycin. Piperacillin-Tazobactam, Roxithromycin, Ticarcillin-Clavulanate, Trovafloxacin (CP 99,219), U-100592, and U-100766 for Various National Committee . . . *Diagn. Microbiol. Infect. Dis.* 24, 87-91 (1996).

Zurenko, G. et al. In Vitro Activities of U-100592 and U-100766, Novel Oxazolidinone Antibacterial Agents. *Antimicrobial Agents and Chemotherapy* 40, 839-845 (1996).

Zurenko, G. et al. Oxazolidinone antibacterial agents: Development of the Clinical Candidates Eperezolid and Linezolid. *Exp. Opin. Invest. Drugs* 6, 151-158 (1997).

OXAZOLIDINONE DERIVATIVES WITH ANTIBIOTIC ACTIVITY

This application is a national stage filing under 35 U.S.C. 371 of PCT application PCT/GB01/01815, filed Apr. 23, 2001, which claims priority from United Kingdom Application No. 0009803.8, filed Apr. 25, 2000, the specifications of each of which are incorporated by reference herein. PCT Application PCT/GB01/01815 was published under PCT Article 21(2) in English.

The present invention relates to antibiotic compounds and in particular to antibiotic compounds containing a substituted oxazolidinone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens, but are also regarded as effective against certain Gram-negative pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant *staphylococcus* (MRSA), methicillin resistant coagulase negative staphylococci (MRCNS), penicillin resistant *Streptococcus pneumoniae* and multiply resistant *Enterococcus faecium*.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of certain Gram negative strains responsible for upper respiratory tract infections. These strains include H.influenzae and M.catarrhalis.

Certain antibacterial compounds containing an oxazolidinone ring have been described in the art (for example, Walter A. Gregory et al in J. Med. Chem. 1990, 33, 2569–2578 and 1989, 32(8), 1673–81; Chung-Ho Park et al in J. Med. Chem. 1992, 35, 1156–1165). Such antibacterial oxazolidinone compounds with a 5-methylacetamide sidechain may be subject to mammalian peptidase metabolism. Furthermore, bacterial resistance to known antibacterial agents may develop, for example, by (i) the evolution of active binding sites in the bacteria rendering a previously active pharmacophore less effective or redundant, and/or (ii) the evolution of means to chemically deactivate a given pharmacophore. Therefore, there remains an ongoing need to find new antibacterial agents with a favourable pharmacological profile, in particular for compounds containing new pharmacophores.

We have discovered a class of antibiotic compounds containing a new class of substituted oxazolidinone ring which has useful activity against Gram-positive pathogens including MRSA and MRCNS and, in particular, against various strains exhibiting resistance to vancomycin and against *E. faecium* strains resistant to both aminoglycosides and clinically used β-lactams, but also to fastidious Gram negative strains such as H.influenzae and M.catarrhalis.

Accordingly the present invention provides a compound of the formula (I), or a pharmaceutically-acceptable salt, or an in-vivo-hydrolysable ester thereof,

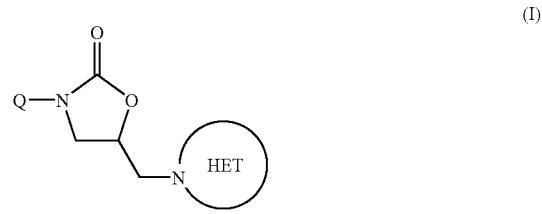

(I)

wherein

HET is an N-linked 5-membered heteroaryl ring, containing either (i) 1 to 3 further nitrogen heteroatoms or (ii) a further heteroatom selected from O and S together with an optional further nitrogen heteroatom; which ring is optionally substituted on a C atom by an oxo or thioxo group; and/or the ring is optionally substituted on a C atom by 1 or 2 (1–4C)alkyl groups; and/or on an available nitrogen atom (provided that the ring is not thereby quaternised) by (1–4C) alkyl; or HET is an N-linked 6-membered heteroaryl ring containing up to three nitrogen heteroatoms in total (including the linking heteroatom), which ring is substituted on a suitable C atom by oxo or thioxo and optionally substituted on any available C atom by 1 or 2 (1–4C)alkyl substituents;

Q is selected from Q1 to Q9

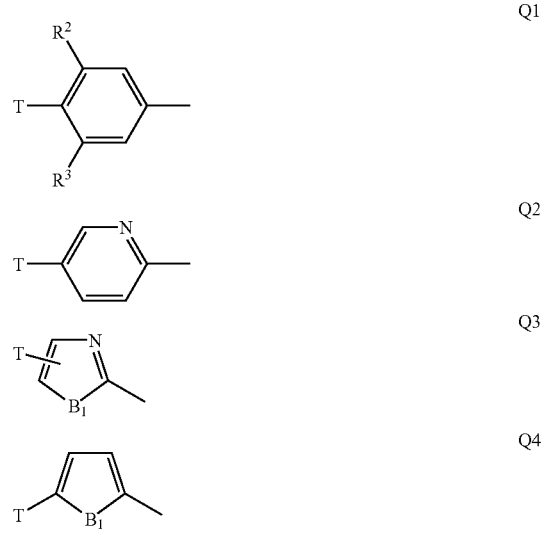

-continued

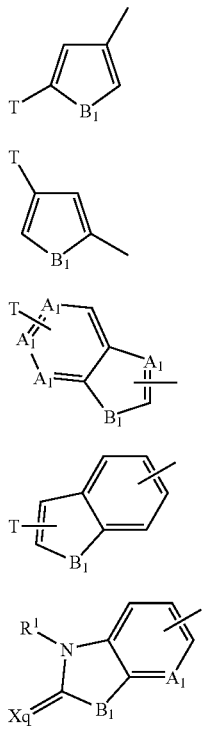

wherein R² and R³ are independently hydrogen or fluoro;

wherein A₁ is carbon or nitrogen; B₁ is O or S (or, in Q9 only, NH); X_q is O, S or N—R¹ (wherein R¹ is hydrogen, (1–4C) alkyl or hydroxy-(1–4C)alkyl); and wherein in Q7 each A₁ is independently selected from carbon or nitrogen, with a maximum of 2 nitrogen heteroatoms in the 6-membered ring, and Q7 is linked to T via any of the A₁ atoms (when A₁ is carbon), and linked in the 5-membered ring via the specified carbon atom, or via A₁ when A₁ is carbon; Q8 is linked to T via either of the specified carbon atoms in the 5-membered ring, and linked in the benzo-ring via either of the two specified carbon atoms on either side of the linking bond shown; and Q9 is linked via either of the two specified carbon atoms on either side of the linking bond shown;

wherein T is selected from the groups in (TA) to (TD) below (wherein AR1, AR2, AR2a, AR2b, AR3, AR3a, AR3 b, AR4, AR4a, CY1 and CY2 are defined hereinbelow);

(TA) T is selected from the following groups:—

(TAa) AR1, AR1-(1–4C)alkyl-, AR2 (carbon linked), AR3;

(TAb) AR1-CH(OH), AR2-CH(OH)—, AR3-CH(OH)—;

(TAc) AR1-CO—, AR2-CO—, AR3-CO—, AR4-CO—;

(TAd) AR1-O—, AR2-O—, AR3-O—;

(TAe) A R1-S(O)q—, AR2-S(O)q—, AR3-S(O)q— (q is 0, 1 or 2);

(TAf) an optionally substituted N-linked (fully unsaturated) 5-membered heteroaryl ring system containing 1, 2 or 3 nitrogen atoms;

(TAg) a carbon linked tropol-3-one or tropol-4-one, optionally substituted in a position not adjacent to the linking position; or (TB) T is selected from the following groups (TBa) halo or (1–4C)alkyl {optionally substituted by one or more groups each independently selected from hydroxy, (1–4C)alkoxy, (1–4C)alkanoyl, cyano, halo, trifluoromethyl, (1–4C)alkoxycarbonyl, —NRvRw, (1–6C)alkanoylamino, (1–4C)alkoxycarbonylamino, N-(1–4C)alkyl-N-(1–6C)alkanoylamino, (1–4C)alkylS(O)q— (q is 0, 1 or 2), CY1, CY2 or AR1};

(TBb) —NRv¹Rw¹;

(TBc) ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl;

(TBd) R¹⁰CO—, R¹⁰S(O)_q— (q is 0, 1 or 2) or R¹⁰CS— wherein R¹⁰ is selected from the following groups:—

(TBda) CY1 or CY2;

(TBdb) hydrogen, (1–4C)alkoxycarbonyl, trifluoromethyl, —NRvRw, ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl or 2-(AR2)ethenyl; or (TBdc) (1–4C)alkyl {optionally substituted as defined in (TBa) above, or by (1–4C)alkylS(O)pNH— or (1–4C)alkylS(O)p-((1–4C)alkyl)N-(p is 1 or 2)};

wherein Rv is hydrogen or (1–4C)alkyl; Rw is hydrogen or (1–4C)alkyl; Rv¹ is hydrogen, (1–4C)alkyl or (3–8C)cycloalkyl; Rw¹ is hydrogen, (1–4C)alkyl, (3–8C)cycloalkyl, (1–4C)alkyl-CO— or (1–4C)alkylS(O)q— (q is 1 or 2); or (TC) T is selected from the following groups (TCa) an optionally substituted, fully saturated 4-membered monocyclic ring containing 1 heteroatom selected from O, N and S (optionally oxidised), and linked via a ring nitrogen or sp³ carbon atom;

(TCb) an optionally substituted 5-membered monocyclic ring containing 1 heteroatom selected from O, N and S (optionally oxidised), and linked via a ring nitrogen atom or a ring sp³ or sp² carbon atom, which monocyclic ring is fully saturated other than (where appropriate) at a linking sp² carbon atom;

(TCc) an optionally substituted 6- or 7-membered monocyclic ring containing 1 or 2 heteroatoms independently selected from O, N and S (optionally oxidised), and linked via a ring nitrogen atom or a ring sp³ or sp² carbon atom, which monocyclic ring is fully saturated other than (where appropriate) at a linking sp² carbon atom; or (TD) T is selected from the following groups:—

(TDa) a bicyclic spiro-ring system containing 0, 1 or 2 ring nitrogen atoms as the only ring heteroatoms, the structure consisting of a 5- or 6-membered ring system (linked via a ring nitrogen atom or a ring sp³ or sp² carbon atom) substituted (but not adjacent to the linking position) by a 3-, 4- or 5-membered spiro-carbon-linked ring; which bicyclic ring system is (i) fully saturated other than (where appropriate) at a linking sp² carbon atom;

(ii) contains one —N(Rc)— group in the ring system (at least two carbon atoms away from the linking position when the link is via a nitrogen atom or an sp² carbon atom) or one —N(Rc)— group in an optional substituent (not adjacent to the linking position) and is (iii) optionally further substituted on an available ring carbon atom; or (TDb) a 7-, 8- or 9-membered bicyclic ring system (linked via a ring nitrogen atom or a ring sp³ or sp² carbon atom) containing 0, 1 or 2 ring nitrogen atoms (and optionally a further O or S ring heteroatom), the structure containing a bridge of 1, 2 or 3 carbon atoms; which bicyclic ring system is (i) fully saturated other than (where appropriate) at a linking sp² carbon atom;

(ii) contains one O or S heteroatom, or one —N(Rc)— group in the ring (at least two carbon atoms away from the linking position when the link is via a nitrogen atom or an sp² carbon atom) or one —N(Rc)— group in an optional substituent (not adjacent to the linking position) and is (iii) optionally further substituted on an available ring carbon atom;

wherein Rc is selected from groups (Rc 1) to (Rc5)

(Rc1) (1–6C)alkyl {optionally substituted by one or more (1–4C)alkanoyl groups (including geminal disubstitution) and/or optionally monosubstituted by cyano, (1–4C)alkoxy, trifluoromethyl, (1–4C)alkoxycarbonyl, phenyl (optionally substituted as for AR defined hereinafter), (1–4C)alkylS(O)$_q$— (q is 0, 1 or 2); or, on any but the first carbon atom of the (1–6C)alkyl chain, optionally substituted by one or more groups (including geminal disubstitution) each independently selected from hydroxy and fluoro, and/or optionally monosubstituted by oxo, —NRvRw [wherein Rv is hydrogen or (1–4C)alkyl; Rw is hydrogen or (1–4C)alkyl], (1–6C)alkanoylamino, (1–4C)alkoxycarbonylamino, N-(1–4C)alkyl-N-(1–6C)alkanoylamino, (1–4C)alkylS(O)pNH— or (1–4C)alkylS(O)p-((1–4C)alkyl)N— (p is 1 or 2)};

(Rc2) R¹³CO—, R¹³SO₂— or R¹³CS— wherein R¹³ is selected from (Rc2a) to (Rc2e)

(Rc2a) AR1, AR2, AR2a, AR2b, AR3, AR3a, AR3b, AR4, AR4a, CY1, CY2;

(Rc2b) hydrogen, (1–4C)alkoxycarbonyl, trifluoromethyl, —NRvRw [wherein Rv is hydrogen or (1–4C)alkyl; Rw is hydrogen or (1–4C)alkyl], ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl, 2-(AR2a)ethenyl;

(Rc2c) (1–10C)alkyl

{optionally substituted by one or more groups (including geminal disubstitution) each independently selected from hydroxy, (1–10C)alkoxy, (1–4C)alkoxy-(1–4C)alkoxy, (1–4C)alkoxy-(1–4C)alkoxy-(1–4C)alkoxy, (1–4C)alkanoyl, phosphoryl [—O—P(O)(OH)₂, and mono- and di-(1–4C)alkoxy derivatives thereof], phosphiryl [—O—P(OH)₂ and mono- and di-(1–4C)alkoxy derivatives thereof], and amino; and/or optionally substituted by one group selected from phosphonate [phosphono, —P(O)(OH)₂, and mono- and di-(1–4C)alkoxy derivatives thereof], phosphinate [-P(OH)₂ and mono- and di-(1–4C)alkoxy derivatives thereof], cyano, halo, trifluoromethyl, (1–4C)alkoxycarbonyl, (1–4C)alkoxy-(1–4C)alkoxycarbonyl, (1–4C)alkoxy-(1–4C)alkoxy-(1–4C)alkoxycarbonyl, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)pNH—, (1–4C)alkylS(O)p-((1–4C)alkyl)N—, fluoro(1–4C)alkylS(O)pNH—, fluoro(1–4C)alkylS(O)p((1–4C)alkyl)N—, (1–4C)alkylS(O)p-[the (1–4C)alkyl group of (1–4C)alkylS(O)$_q$— being optionally substituted by one substituent selected from hydroxy, (1–4C)alkoxy, (1–4C)alkanoyl, phosphoryl [—O—P(O)(OH)₂, and mono- and di-(1–4C)alkoxy derivatives thereof], phosphiryl [—O—P(OH)₂ and mono- and di-(1–4C)alkoxy derivatives thereof], amino, cyano, halo, trifluoromethyl, (1–4C)alkoxycarbonyl, (1–4C)alkoxy-(1–4C)alkoxycarbonyl, (1–4C)alkoxy-(1–4C)alkoxy-(1–4C)alkoxycarbonyl, carboxy, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)pNH—, (1–4C)alkylS(O)p-((1–4C)alkyl)N—, (1–4C)alkylS(O)q—, AR1-S(O)q—, AR2-S(O)q—, AR3-S(O)q— and also AR2a, AR2b, AR3a and AR3b versions of AR2 and AR3 containing groups], CY1, CY2, AR1, AR2, AR3, AR1—O—, AR2—O—, AR3—O—, AR1-S(O)q—, AR2-S(O)q—, AR3-S(O)q—, AR1—NH—, AR2—NH—, AR3—NH— (p is 1 or 2 and q is 0, 1 or 2), and also AR2a, AR2b, AR3a and AR3b versions of AR2 and AR3 containing groups};

(Rc2d) R¹⁴C(O)O(1–6C)alkyl wherein R¹⁴ is AR1, AR2, (1–4C)alkylamino (the (1–4C)alkyl group being optionally substituted by (1–4C)alkoxycarbonyl or by carboxy), benzyloxy-(1–4C)alkyl or (1–10C)alkyl {optionally substituted as defined for (Rc2c)};

(Rc2e) R¹⁵O— wherein R¹⁵ is benzyl, (1–6C)alkyl {optionally substituted as defined for (Rc2c)}, CY1, CY2 or AR2b;

(Rc3) hydrogen, cyano, 2-cyanoethenyl, 2-cyano-2-((1–4C)alkyl)ethenyl, 2-((1–4C)alkylaminocarbonyl)ethenyl, 2-((1–4C)alkoxycarbonyl)ethenyl, 2-nitroethenyl, 2-nitro-2-((1–4C)alkyl)ethenyl, 2-(AR1)ethenyl, 2-(AR2)ethenyl, or of the formula (Rc3a)

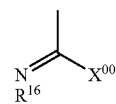

(Rc3a)

wherein X⁰⁰ is —OR¹⁷, —SR¹⁷, —NHR¹⁷ and —N(R¹⁷)₂;

wherein R¹⁷ is hydrogen (when X⁰⁰ is —NHR¹⁷ and —N(R¹⁷)₂), and R¹⁷ is (1–4C)alkyl, phenyl or AR2 (when X⁰⁰ is —OR¹⁷, —SR¹⁷ and —NHR¹⁷); and R¹⁶ is cyano, nitro, (1–4C)alkylsulfonyl, (4–7C)cycloalkylsulfonyl, phenylsulfonyl, (1–4C)alkanoyl and (1–4C)alkoxycarbonyl;

(Rc4) trityl, AR1, AR2, AR2a, AR2b, AR3, AR3a, AR3b;

(Rc5) RdOC(Re)=CH(C=O)—, RfC(=O)C(=O)—, RgN=C(Rh)C(=O)— or

RiNHC(Rj)=CHC(=O)— wherein Rd is (1–6C)alkyl; Re is hydrogen or (1–6C)alkyl, or Rd and Re together form a (3–4C)alkylene chain; Rf is hydrogen, (1–6C)alkyl, hydroxy (1–6C)alkyl, (1–6C)alkoxy(1–6C)alkyl, —NRvRw [wherein Rv is hydrogen or (1–4C)alkyl; Rw is hydrogen or (1–4C)alkyl], (1–6C)alkoxy, (1–6C)alkoxy(1–6C)alkoxy, hydroxy(2–6C)alkoxy, (1–4C)alkylamino(2–6C)alkoxy, di-(1–4C)alkylamino(2–6C)alkoxy; Rg is (1–6C)alkyl, hydroxy or (1–6C)alkoxy; Rh is hydrogen or (1–6C)alkyl; Ri is hydrogen, (1–6C)alkyl, AR1, AR2, AR2a, AR2b and Rj is hydrogen or (1–6C)alkyl;

wherein

AR1 is an optionally substituted phenyl or optionally substituted naphthyl;

AR2 is an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;

AR2a is a partially hydrogenated version of AR2 (i.e. AR2 systems retaining some, but not the full, degree of unsaturation), linked via a ring carbon atom or linked via a ring nitrogen atom if the ring is not thereby quaternised;

AR2b is a fully hydrogenated version of AR2 (i.e. AR2 systems having no unsaturation), linked via a ring carbon atom or linked via a ring nitrogen atom;

AR3 is an optionally substituted 8-, 9- or 10-membered, fully unsaturated (i.e with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;

AR3a is a partially hydrogenated version of AR3 (i.e. AR3 systems retaining some, but not the full, degree of unsaturation), linked via a ring carbon atom, or linked via a ring nitrogen atom if the ring is not thereby quaternised, in either of the rings comprising the bicyclic system;

AR3b is a fully hydrogenated version of AR3 (i.e. AR3 systems having no unsaturation), linked via a ring carbon atom, or linked via a ring nitrogen atom, in either of the rings comprising the bicyclic system;

AR4 is an optionally substituted 13- or 14-membered, fully unsaturated (i.e with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;

AR4a is a partially hydrogenated version of AR4 (i.e. AR4 systems retaining some, but not the full, degree of unsaturation), linked via a ring carbon atom, or linked via a ring nitrogen atom if the ring is not thereby quaternised, in any of the rings comprising the tricyclic system;

CY1 is an optionally substituted cyclobutyl, cyclopentyl or cyclohexyl ring;

CY2 is an optionally substituted cyclopentenyl or cyclohexenyl ring.

In this specification, where it is stated that a ring may be linked via an $sp^2$ carbon atom, which ring is fully saturated other than (where appropriate) at a linking $sp^2$ carbon atom, it is to be understood that the ring is linked via one of the carbon atoms in a C=C double bond.

In another embodiment, (Rc1) is as defined above other than the optional phenyl substituent on (1–6C)alkyl is optionally substituted as for AR1 defined hereinafter; and (Rc2c), is as defined above and further includes carboxy as an optional substituent on $R^{13}$ as (1–10C)alkyl.

(TAf) When T is an optionally substituted N-linked (fully unsaturated) 5-membered heteroaryl ring system containing 1, 2 or 3 nitrogen atoms, it is preferably selected from a group of formula (TAf1) to (TAf6) below (particularly (TAf1), (TAf2), (TAf4) and (TAf5), and especially (TAf1) and/or (TAf2)). The above preferred values of (TAf) are particularly preferred when present in Q1 or Q2, especially Q1.

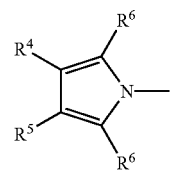

(TAf1)

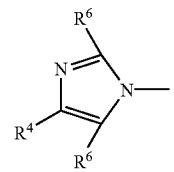

(TAf2)

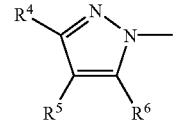

(TAf3)

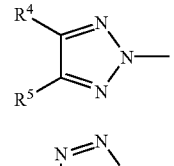

(TAf4)

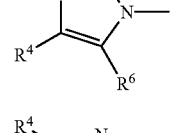

(TAf5)

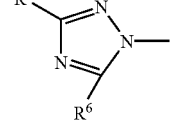

(TAf6)

wherein:

$R^6$ is selected (independently where appropriate) from hydrogen, (1–4C)alkyl, (1–4C)alkoxycarbonyl, (1–4C)alkanoyl, carbamoyl and cyano;

$R^4$ and $R^5$ are independently selected from hydrogen, halo, trifluoromethyl, cyano, nitro, (1–4C)alkoxy, (1–4C)alkylS(O)q— (q is 0, 1 or 2), (1–4C)alkanoyl, (1–4C)alkoxycarbonyl, (2–4C)alkanoyloxy-(1–4C)alkyl, benzoxy-(1–4C)

alkyl, (2–4C)alkanoylamino, —CONRvRw, —NRvRw and (1–4C)alkyl {optionally substituted by hydroxy, trifluoromethyl, cyano, nitro, (1–4C)alkoxy, (1–4C)alkylS(O)$_q$— (q is 0, 1 or 2), (1–4C)alkoxycarbonyl, (1–4C)alkanoylamino, —CONRvRw, —NRvRw; wherein RvRw is hydrogen or (1–4C)alkyl; Rw is hydrogen or (1–4C)alkyl};

or R$^4$ is selected from one of the groups in (TAfa) to (TAfc) below, or (where appropriate) one of R$^4$ and R$^5$ is selected from the above list of R$^4$ and R$^5$ values, and the other is selected from one of the groups in (TAfa) to (TAfc) below:—

(TAfa) a group of the formula (TAfa1)×

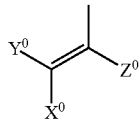

(TAfa1)

wherein Z° is hydrogen or (1–4C)alkyl;

X° and Y° are independently selected from hydrogen, (1–4C)alkyl, (1–4C)alkoxycarbonyl, halo, cyano, nitro, (1–4C)alkylS(O)q— (q is 0, 1 or 2), RvRwNSO$_2$—, trifluoromethyl, pentafluoroethyl, (1–4C)alkanoyl and —CONRvRw [wherein Rv is hydrogen or (1–4C)alkyl; Rw is hydrogen or (1–4C)alkyl]; or one of X° and Y° is selected from the above list of X° and Y° values, and the other is selected from phenyl, phenylcarbonyl, —S(O)$_q$-phenyl (q is 0, 1 or 2), N-(phenyl)carbamoyl, phenylaminosulfonyl, AR2, (AR2)—CO—, (AR2)—S(O)$_q$— (q is 0, 1 or 2), N-(AR2)carbamoyl and (AR2)aminosulfonyl; wherein any phenyl group in (TAfa) may be optionally substituted by up to three substituents independently selected from (1–4C)alkyl, cyano, trifluoromethyl, nitro, halo and (1–4C)alkylsulfonyl;

(TAfb) an acetylene of the formula —≡—H or —≡—(1–4C)alkyl;

(TAfc)—X$^1$—Y$^1$—AR2, —X$^1$—Y$^1$—AR2a, —X$^1$—Y$^1$—AR2b, —X$^1$—Y$^1$—AR3, —X$^1$—Y$^1$—AR3a or —X$^1$—Y$^1$—AR3b;

wherein X$^1$ is a direct bond or —CH(OH)— and

Y$^1$ is —(CH$_2$)$_m$—, —(CH$_2$)$_n$—NH—(CH$_2$)$_m$—, —CO—(CH$_2$)$_m$—, —CONH—(CH$_2$)$_m$—, —C(=S)NH—(CH$_2$)$_m$— or —C(=O)O—(CH$_2$)$_m$—;

or wherein X$^1$ is —(CH$_2$)$_n$— or —CH(Me)-(CH$_2$)$_m$— and

Y$^1$ is —(CH$_2$)$_m$—NH—(CH$_2$)$_m$—, —CO—(CH$_2$)$_m$—, —CONH—(CH$_2$)$_m$—, —C(=S)NH—(CH$_2$)$_m$—, —C(=O)O—(CH$_2$)$_m$— or —S(O)$_q$—(CH$_2$)$_m$—;

or wherein X$^1$ is —CH$_2$O—, —CH$_2$NH— or —CH$_2$N((1–4C)alkyl)- and

Y$^1$ is —CO—(CH$_2$)$_m$—, —CONH—(CH$_2$)$_m$— or —C(=S)NH—(CH$_2$)$_m$—; and additionally Y$^1$ is —SO$_2$— when X$^1$ is —CH$_2$NH— or —CH$_2$N((1–4C)alkyl)-, and Y$^1$ is —(CH$_2$)$_m$— when X$^1$ is —CH$_2$O— or —CH$_2$N((1–4C)alkyl)—; wherein n is 1, 2 or 3; m is 0, 1, 2 or 3 and q is 0, 1 or 2; and when Y$^1$ is —(CH$_2$)$_m$—NH—(CH$_2$)$_m$— each m is independently selected from 0, 1, 2 or 3.

It is to be understood that when a value for —X$^1$—is a two-atom link and is written, for example, as —CH$_2$NH— it is the left hand part (—CH$_2$— here) which is bonded to the group of formula (TAf1) to (TAf6) and the right hand part (—NH— here) which is bonded to —Y$^1$— in the definition in (TAfc). Similarly, when —Y$^1$— is a two-atom link and is written, for example, as —CONH— it is the left hand part of —Y$^1$— (—CO— here) which is bonded to the right hand part of —X$^1$-, and the right hand part of —Y$^1$— (—NH— here) which is bonded to the AR2, AR2a, AR2b, AR3, AR3a or AR3b moiety in the definition in (TAfc).

Preferably R is hydrogen or (1–4C)alkyl, and R$^4$ and R$^5$ are independently selected from hydrogen, (1–4C)alkyl or one of R$^4$ and R$^5$ is selected from group (TAfa). Other preferable substituents on the (TAf1) to (TAf6) are illustrated in the accompanying Examples. Most preferable is (TAf2) with such preferable substituents.

(TAg) When T is a carbon linked tropol-3-one or tropol-4-one, optionally substituted in a position not adjacent to the linking position (TAg), it is preferably selected from a group of formula (TAg1), (TAg2) or (TAg3). The above preferred values of (TAg) are particularly preferred when present in Q1 or Q2, especially Q1.

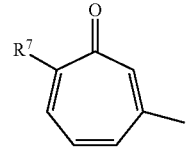

(TAg1)

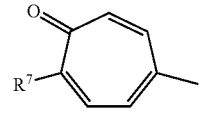

(TAg2)

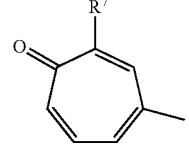

(TAg3)

wherein R$^7$ is selected from (TAga) hydrogen, (1–4C)alkyl {optionally substituted by one or two substituents (excluding geminal disubstitution) independently selected from fluoro, hydroxy, (1–4C)alkoxy and —NRvRw]}; or (TAgb)R$^8$—O—, R$^8$—S—, R$^8$—NH— or R$^8$R$^8$—N—;

wherein R$^8$ is selected (independently where appropriate) from hydrogen, (1–4C)alkyl or (3–8C)cycloalkyl {both optionally substituted by one or two substituents (excluding geminal disubstitution) independently selected from hydroxy, (1–4C)alkoxy, (1–4C)alkoxycarbonyl and —NRvRw}, (2–4C)alkenyl {optionally substituted by one or two —NRvRw substituents}, (1–4C)alkanoyl {optionally substituted by one or two substituents independently selected from —NRvRw and hydroxy}, phenyl-(1–4C)alkyl or pyridyl-(1–4C)alkyl {the phenyl and pyridyl (preferably pyridin-4-yl) rings being optionally substituted by one or two —NRvRw substituents}; or (TAgc) morpholino, thiomorpholino, pyrrolidino {optionally independently substituted in the 3- and/or 4-positions by (1–4C)alkyl}, piperidino substituted in the 4-position by $R^9$—, $R^9$—O—, $R^9$—S—, $R^9$—NH— or $R^9R^9$—N—; wherein $R^9$ is selected (independently where appropriate) from hydrogen, (1–4C)alkyl {optionally substituted by one or two (excluding geminal disubstitution) hydroxy, (1–4C) alkoxy, (1–4C)alkoxycarbonyl or —NRvRw} and piperazino {optionally substituted in the 4-position by (1–4C) alkyl, (3–8C)cycloalkyl, (1–4C)alkanoyl, (1–4C) alkoxycarbonyl or (1–4C)alkylsulfonyl, and optionally independently substituted in the 3- and/or 5-positions by (1–4C)alkyl}; wherein Rv is hydrogen or (1–4C)alkyl; Rw is hydrogen or (1–4C)alkyl.

(TC) Preferred values for the optional substituents and groups defined in (TCa) to (TCc) are defined by formulae (TC1) to (TC4):—

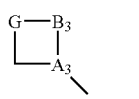

(TC1)

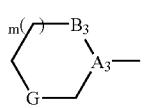

(TC2)

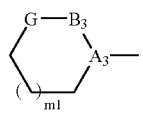

(TC3)

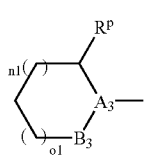

(TC4)

wherein in (TC1): $>A_3$-$B_3$— is $>$C(Rq)-CH(Rr)- and G is —O—, —S—, —SO—, —SO$_2$— or $>$N(Rc);

wherein in (TC2): m1 is 0, 1 or 2; $>A_3$-$B_3$- is $>$C=C(Rr)- or $>$C(Rq)-CH(Rr)- and G is —O—, —S—, —SO—, —SO$_2$— or $>$N(Rc);

wherein in (TC3) m1 is 0, 1 or 2; $>A_3$-$B_3$- is $>$C(Rq)-CH(Rr)— (other than when Rq and Rr are both together hydrogen) and G is —O—, —S—, —SO—, —SO$_2$— or $>$N(Rc);

wherein in (TC4): n1 is 1 or 2; o1 is 1 or 2 and n1+o1=2 or 3; $>A_3$-$B_3$— is $>$C=C(Rr)— or $>$C(Rq)—CH(Rr)— or $>$N—CH$_2$— and G is —O—, —S—, —SO—, —SO$_2$— or $>$N(Rc); Rp is hydrogen, (1–4C)alkyl (other than when such substitution is defined by $>A_3$-$B_3$-), hydroxy, (1–4C)alkoxy or (1–4C)alkanoyloxy;

wherein in (TC1), (TC2) and (TC4); m1, n1 and o1 are as defined hereinbefore:

$>A_3$-$B_3$- is $>$N—CH$_2$— and G is $>$C($R^{11}$)($R^{12}$), $>$C=O, $>$C—OH, $>$C-(1–4C)alkoxy, $>$C=N—OH, $>$C=N-(1–4C)alkoxy, $>$C=N—NH-(1–4C)alkyl, $>$C=N—N((1–4C)alkyl)$_2$ (the last two (1–4C)alkyl groups above in G being optionally substituted by hydroxy) or $>$C=N—N—CO-(1–4C)alkoxy; wherein $>$ represents two single bonds;

Rq is hydrogen, hydroxy, halo, (1–4C)alkyl or (1–4C) alkanoyloxy;

Rr is (independently where appropriate) hydrogen or (1–4C) alkyl;

$R^{11}$ is hydrogen, (1–4C)alkyl, fluoro(1–4C)alkyl, (1–4C) alkyl-thio-(1–4C)alkyl or hydroxy-(1–4C)alkyl and $R^{12}$ is —[C(Rr)(Rr)]$_{m2}$-N(Rr)(Rc) wherein m2 is 0, 1 or 2;

and, other than the ring substitution defined by G, $>A_3$-$B_3$- and Rp, each ring system may be optionally further substituted on a carbon atom not adjacent to the link at $>A_3$- by up to two substituents independently selected from (1–4C) alkyl, fluoro(1–4C)alkyl (including trifluoromethyl), (1–4C) alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, AR-oxymethyl, AR-thiomethyl, oxo (=O) (other than when G is $>$N-Rc and Rc is group (Rc2) defined hereinbefore) or independently selected from Rc; and also hydroxy or halo (the last two optional substituents only when G is —O— or —S—); wherein AR (or ARp) is as defined for formula (IP) hereinafter; Rc is selected from groups (Rc1) to (Rc5) defined hereinbefore.

For the avoidance of doubt, ( )$_{m1}$, ( )$_{n1}$ and ( )$_{o1}$ indicate (—CH$_2$-)$_{m1}$, (—CH$_2$-)$_{n1}$ and (—CH$_2$—)$_{o1}$ respectively (optionally substituted as described above).

In the above definition of (TC1) to (TC4) and of the further optional substituents, AR is preferably AR2, and the further optional substituents are preferably not selected from the values listed for Rc. A preferred value for G is $>$N(Rc) or $>$C($R^{11}$)($R^{12}$).

Particularly preferred values for the optional substituents and groups defined in (TCa) to (TCc), and (TC1) to (TC4) are contained in the following definitions (TC5) to (TC11):—

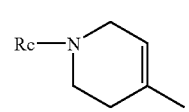

(TC5)

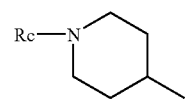

(TC6)

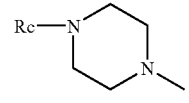

(TC7)

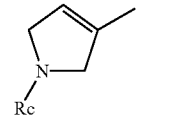

(TC8)

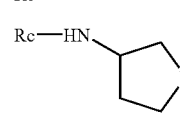

(TC9)

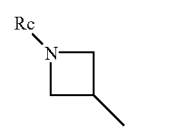

(TC10)

-continued (TC11)

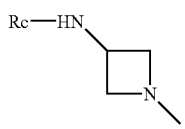

wherein Rc has any of the values listed hereinbefore or hereinafter.

Especially preferred are (TC5), (TC6), (TC7) and (TC9), most especially (TC5) in which Rc has any of the values listed hereinbefore or hereinafter (especially $R^{13}CO$— with the preferable $R^{13}$ values given hereinafter). In (TC5) Rc is preferably selected from the group (Rc2), especially $R^{13}CO$— with the preferable $R^{13}$ values given hereinafter. In (TC7) Rc is preferably selected from group (Rc3) or (Rc4).

The above preferred values of (TCa) to (TCc) are particularly preferred when present in Q1 or Q2, especially Q1 (especially when HET is isoxazole).

(TDa) When T is a bicyclic spiro-ring system as defined in (TDa), it is preferably selected from a group of formula (TDa1) to (TDa9). The above preferred values of (TDa) are particularly preferred when present in Q1 or Q2, especially Q1.

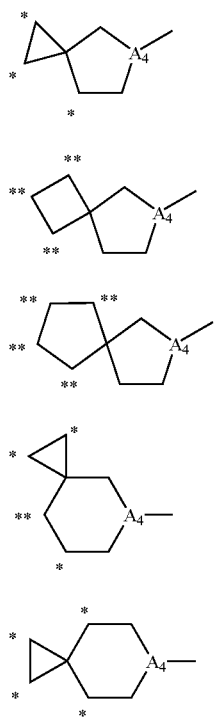

(TDa1)
(TDa2)
(TDa3)
(TDa4)
(TDa5)
(TDa6)

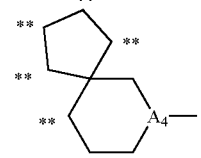

(TDa7)

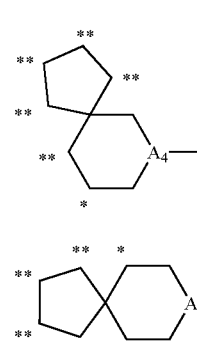

(TDa8)

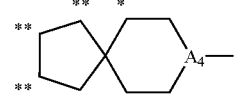

(TDa9)

wherein;

(i) the $A_4$ linking group is a nitrogen atom or an $sp^3$ or $sp^2$ carbon atom (with the double bond, where appropriate, orientated in either direction); and (ii) one of the ring carbon atoms at positions marked * and ** is replaced by one of the following groups —NRc—, >CH—NHRc, >CH—NRc-(1–4C)alkyl, >CH—CH$_2$—NHRc, >CH—CH$_2$—NRc-(1–4C)alkyl [wherein a central —CH$_2$— chain link is optionally mono- or di-substituted by (1–4C)alkyl]; with the provisos that positions marked * are not replaced by —NH— in the ring containing the $A_4$ link when $A_4$ is a nitrogen atom or an $sp^2$ carbon atom, and that positions marked * are not replaced by —NH— in the three membered ring in (TDa1), (TDa4) and (TDa5); and (iii) the ring system is optionally (further) substituted on an available ring carbon atom by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–5C)alkoxycarbonyl, AR2-oxymethyl, AR2-thiomethyl, oxo (═O) (other than when the ring contains an >N—Rc and Rc is group (Rc2)) and also hydroxy or halo; wherein Rc has any of the values listed hereinbefore or hereinafter.

(TDb) When T is a 7-, 8- or 9-membered bicyclic ring system containing a bridge of 1, 2 or 3 carbon atoms as defined in (TDb), it is preferably selected from a group defined by the ring skeletons shown in formulae (TDb1) to (TDb14):—

7-membered ring skeletons

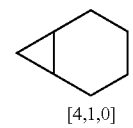

(TDb1)

[4,1,0]

-continued

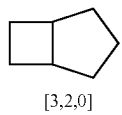
[3,2,0]

[3,1,1]

[2,2,1]

8-membered ring skeletons

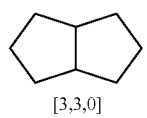
[3,3,0]

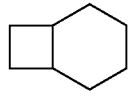
[4,2,0]

[4,1,1]

[3,2,1]

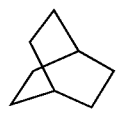
[2,2,2]

9-membered ring skeletons

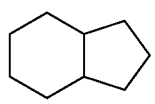
[4,3,0]

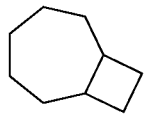
[5,2,0]

(TDb2)

(TDb3)

(TDb4)

(TDb5)

(TDb6)

(TDb7)

(TDb8)

(TDb9)

(TDb10)

(TDb11)

(TDb12)
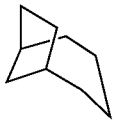
[4,2,1]

(TDb13)
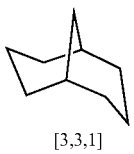
[3,3,1]

(TDb14)
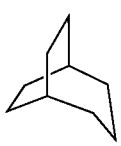
[3,2,2]

wherein;

(i) the ring system contains 0, 1 or 2 ring nitrogen atoms (and optionally a further O or S ring heteroatom), and when present the ring nitrogen, O or S heteroatom/s are at any position other than as part of the 3-membered ring in (TDb1);

(ii) the ring system is linked via a ring nitrogen atom or a ring sp$^3$ or sp$^2$ carbon atom (with the double bond, where appropriate, orientated in either direction) from any position in either ring [other than from a bridgehead position or from an sp$^2$ carbon atom in the 4-membered ring in (TDb2), (TDb6) and (TDb11)];

(iii) one of the ring carbon atoms at a position not adjacent to the linking position, is replaced (other than when the ring contains an O or S heteroatom) by one of the following groups —NRc-[not at a bridgehead position], >C(H)—NHRc, >C(H)—NRc-(1–4C)alkyl, >C(H)—CH$_2$—NHRc, >C(H)—CH$_2$—NRc-(1–4C)alkyl [wherein the hydrogen atom shown in brackets is not present when the replacement is made at a bridgehead position and wherein a central —CH$_2$— chain link is optionally mono- or di-substituted by (1–4C)alkyl]; with the proviso that when the ring system is linked via a ring nitrogen atom or an sp$^2$ carbon atom any replacement of a ring carbon atom by —NRc—, O or S is at least two carbon atoms away from the linking position; and (iv) the ring system is optionally (further) substituted on an available ring carbon atom as for the bicyclic spiro-ring systems described in (TDa); wherein Rc has any of the values listed hereinbefore or hereinafter.

It will be appreciated that unstable anti-Bredt compounds are not contemplated in this definition (i.e. compounds with stuctures (TDb3), (TDb4), (TDb7), (TDb8), (TDb9), (TDb12), (TDb13) and (TDb14) in which an sp$^2$ carbon atom is directed towards a bridgehead position).

Particularly preferred values of (TDb) are the following structures of formula (TDb4), (TDb8) and/or (TDb9); wherein Rc has any of the values listed hereinbefore or hereinafter. The above preferred values of (TDb) are particularly preferred when present in Q1 or Q2, especially Q1.

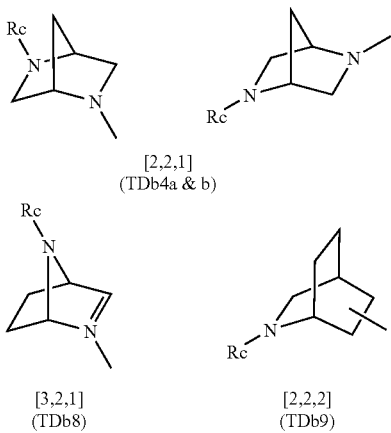

[2,2,1]
(TDb4a & b)

[3,2,1]
(TDb8)

[2,2,2]
(TDb9)

In another embodiment there is provided a compound of formula (I) as defined by formula (IP) below:

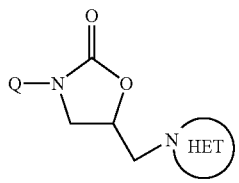

(IP)

wherein

HET is an N-linked 5-membered heteroaryl ring, containing either (i) 1 to 3 further nitrogen heteroatoms or (ii) a further heteroatom selected from O and S together with an optional further nitrogen heteroatom; which ring is optionally substituted on a C atom by an oxo or thioxo group; and/or the ring is optionally substituted on a C atom by 1 or 2 (1–4C)alkyl groups; and/or on an available nitrogen atom (provided that the ring is not thereby quaternised) by (1–4C) alkyl;

Q is

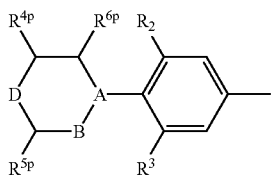

wherein:

$R^2$ and $R^3$ are independently hydrogen or fluoro;

$R^{6p}$ is hydrogen, (1–4C)alkyl, hydroxy, (1–4C)alkoxy or (2–4C)alkanoyloxy;

>A—B— is of the formula >C=C($R^a$)-, >CHCH$R^a$, >C(OH)CH$R^a$— or >N—CH$_2$-(>represents two single bonds) wherein $R^a$ is hydrogen or (1–4C)alkyl;

D is O, S, SO, SO$_2$ or $NR^{7p}$;

$R^{4p}$ and $R^{5p}$ are independently oxo (=O) [but not when $R^{7p}$ is group (PC) below], (1–4C)alkyl, (1–4C)alkanoylamino-(1–4C)alkyl, hydroxy-(1–4C)alkyl, carboxy, (1–4C)alkoxycarbonyl, ARp-oxymethyl, ARp-thiomethyl (wherein ARp is as defined hereinbelow) or independently as defined for $R^{7p}$ hereinbelow with the proviso that $R^{4p}$ and $R^{5p}$ are not phenyl, benzyl, ARp (as defined hereinbelow), a tetrazole ring system, cyclopentyl or cyclohexyl; and when D is O or S, $R^{4p}$ and $R^{5p}$ are additionally independently hydroxy or bromo; wherein $R^{7p}$ is selected from (PA) to (PE):—

(PA) hydrogen, cyano, 2-((1–4C)alkoxycarbonyl)ethenyl, 2-cyanoethenyl, 2-cyano-2-((1–4C)alkyl)ethenyl, 2-((1–4C) alkylaminocarbonyl)ethenyl;

(PB) phenyl, benzyl, ARp (as defined hereinbelow) or a tetrazole ring system [optionally mono-substituted in the 1- or 2- position of the tetrazole ring by (1–4C)alkyl, (2–4C) alkenyl, (2–4C)alkynyl or (1–4C)alkanoyl] wherein the tetrazole ring system is joined to the nitrogen in $NR^{7p}$ by a ring carbon atom;

(PC)$R^{10p}$CO—, $R^{10p}$SO$_2$— or $R^{10p}$CS— wherein $R^{10p}$ is selected from (PCa) to (PCf):—

(PCa) ARp (as defined hereinbelow);

(PCb) cyclopentyl or cyclohexyl or 1,3-dioxolan-4-yl or 1,4-dioxan-2-yl or 1,3-dioxan-4-yl [optionally mono- or disubstituted by substituents independently selected from (1–4C)alkyl (including geminal disubstitution), hydroxy (but excluding 1,3-dioxolan-4-yl, 1,4-dioxan-2-yl and 1,3-dioxan-4-yl substituted by hydroxy), (1–4C)alkoxy, (1–4C) alkylthio, acetamido, (1–4C)alkanoyl, cyano and trifluoromethyl];

(PCc) hydrogen, (1–4C)alkoxycarbonyl, trifluoromethyl, amino, (1–4C)alkylamino, di((1–4C)alkyl)amino, 2-(5- or 6-membered heteroaryl)ethenyl, 2-(5- or 6-membered (partially) hydrogenated heteroaryl)ethenyl, 2-phenylethenyl [wherein the heteroaryl or phenyl substituent is optionally substituted on an available carbon atom by up to three substituents independently selected from (1–4C)alkoxy, halo, cyano and (for the phenyl substituent only) (1–4C) alkylsulfonyl];

(PCd) (1–10C)alkyl [optionally substituted by one or more groups (including geminal disubstitution) each independently selected from hydroxy and amino, or optionally monosubstituted by cyano, halo, (1–10C)alkoxy, trifluoromethyl, (1–4C)alkoxy-(1–4C)alkoxy, (1–4C)alkoxy-(1–4C) alkoxy-(1–4C)alkoxy, (1–4C)alkanoyl, (1–4C)alkoxycarbonyl, (1–4C)alkylamino, di((1–4C)alkyl)amino, (1–6C) alkanoylamino, (1–4C)alkoxycarbonylamino, N-(1–4C) alkyl-N-(2–6C)alkanoylamino, (1–4C)alkylS (O)$_p$NH—, (1–4C)alkylS(O)$_p$((1–4C)alkyl)N—, fluoro(1–4C)alkylS (O)$_p$NH—, fluoro(1–4C)alkylS(O)$_p$((1–4C)alkyl)N—, phosphono, (1–4C)alkoxy(hydroxy)phosphoryl, di-(1–4C) alkoxyphosphoryl, (1–4C)alkylS(O)$_q$—, phenyl, naphthyl, phenoxy, naphthoxy, phenylamino, naphthylamino, phenylS (O)$_q$—, naphthylS(O)$_q$— [wherein said phenyl and naphthyl groups are optionally substituted by up to three substituents independently selected from (1–4C)alkoxy, halo and cyano], or CYp (as defined hereinbelow), wherein (where appropriate) p is 1 or 2 and q is 0, 1 or 2]; (PCe) $R^{11p}$C(O)O(1–6C) alkyl wherein $R^{11p}$ is an optionally substituted 5- or 6-membered heteroaryl, optionally substituted phenyl, (1–4C) alkylamino, benzyloxy-(1–4C)alkyl or optionally substituted (1–10C)alkyl;-

(PCf) $R^{12p}O$— wherein $R^{12p}$ is benzyl or optionally substituted (1–6C)alkyl;

(PD) $R^{10}C(Re)$=CH(C=O)—, R C(=O)C(=O)—, RgN=C(Rh)C(=O)— or $R^iNHC(R^j)$=CHC(=O)— wherein $R^d$ is (1–6C)alkyl, $R^e$ is hydrogen or (1–6C)alkyl, or $R^d$ and $R^e$ together form a (3–4C)alkylene chain, $R^h$ is hydrogen, (1–6C)alkyl, hydroxy(1–6C)alkyl, (1–6C)alkoxy (1–6C)alkyl, amino, (1–4C)alkylamino, di-(1–4C)alkylamino, (1–6C)alkoxy, (1–6C)alkoxy(1–6C)alkoxy, hydroxy (2–6C)alkoxy, (1–4C)alkylamino(2–6C)alkoxy, di-(1–4C)alkylamino(2–6C)alkoxy, $R^{13p}$ is (1–6C)alkyl, hydroxy or (1–6C)alkoxy, $R^h$ is hydrogen or (1–6C)alkyl, $R^i$ is hydrogen, (1–6C)alkyl, optionally substituted phenyl or an optionally substituted 5- or 6-membered heteroaryl [and (partially) hydrogenated versions thereof] and $R^j$ is hydrogen or (1–6C)alkyl;

(PE) $R^{14P}$ CH($R^{13p}$)(CH$_2$)$_m$— wherein m is 0 or 1, $R^{13p}$ is fluoro, cyano, (1–4C)alkoxy, (1–4C)alkylsulfonyl, (1–4C)alkoxycarbonyl or hydroxy, (provided that when m is 0, $R^{13p}$ is not fluoro or hydroxy) and $R^{14p}$ is hydrogen or (1–4C)alkyl;

wherein ARp is optionally substituted phenyl, optionally substituted phenyl(1–4C)alkyl, optionally substituted naphthyl, optionally substituted 5- or 6-membered heteroaryl;

wherein ARp is also an optionally substituted 5/6 or 6/6 bicyclic heteroaryl ring system, in which the bicyclic heteroaryl ring systems may be linked via an atom in either of the rings comprising the bicyclic system, and wherein both the mono- and bicyclic heteroaryl ring systems are linked via a ring carbon atom and may be (partially) hydrogenated; wherein CYp is selected from:—

(i) 4-, 5- or 6-membered cycloalkyl ring;

(ii) 5- or 6-membered cycloalkenyl ring;

(iii) 5- or 6-membered heteroaryl, 5- or 6-membered heteroaryloxy, 5- or 6-membered heteroaryl-S(O)$_q$—, 5- or 6-membered heteroarylamino [and (partially) hydrogenated versions thereof] and (iv) 5/6 or 6/6 bicyclic heteroaryl, 5/6 or 6/6 bicyclic heteroaryloxy, 5/6 or 6/6 bicyclic heteroaryl-S(O)$_q$—, 5/6 or 6/6 bicyclic heteroarylamino [and (partially) hydrogenated versions thereof];

wherein q is 0, 1 or 2 and any of the aforementioned ring systems in CYp may be optionally substituted by up to three substituents independently selected from halo, (1–4C)alkyl [including geminal disubstitution when CYp is a cycloalkyl or cycloalkenyl ring], acyl, oxo and nitro-(1–4C)alkyl; and pharmaceutically-acceptable salts thereof.

In this embodiment (IP) of the specification the term 'alkyl' includes straight chained and branched structures. For example, (1–6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1–4C)alkyl includes 1-bromoethyl and 2-bromoethyl.

In this embodiment (IP) of the specification a '5- or 6-membered heteroaryl' and 'heteroaryl (monocyclic) ring' means a 5- or 6-membered aryl ring wherein (unless stated otherwise) 1, 2 or 3 of the ring atoms are selected from nitrogen, oxygen and sulfur. Unless stated otherwise, such rings are fully aromatic. Particular examples of 5- or 6-membered heteroaryl ring systems are furan, pyrrole, pyrazole, imidazole, triazole, pyrimidine, pyridazine, pyridine, isoxazole, oxazole, isothiazole, thiazole and thiophene.

In this embodiment (IP) of the specification a '5/6 or 6/6 bicyclic heteroaryl ring system' and 'heteroaryl (bicyclic) ring' means an aromatic bicyclic ring system comprising a 6-membered ring fused to either a 5 membered ring or another 6 membered ring, the bicyclic ring system containing 1 to 4 heteroatoms selected from nitrogen, oxygen and sulfur. Unless stated otherwise, such rings are fully aromatic. Particular examples of 5/6 and 6/6 bicyclic ring systems are indole, benzofuran, benzoimidazole, benzothiophene, benzisotbiazole, benzoxazole, benzisoxazole, pyridoimidazole, pyrimidoimidazole, quinoline, quinoxaline, quinazoline, phthalazine, cinnoline and naphthyridine.

In this embodiment (IP) of the specification a '4-, 5- or 6-membered cycloalkyl ring' means a cyclobutyl, cyclopentyl or cyclohexyl ring; and a '5- or 6-membered cycloalkenyl ring' a means cyclopentenyl or cyclohexenyl ring.

Particular optional substituents for alkyl, phenyl (and phenyl containing moieties) and naphthyl groups and ring carbon atoms in heteroaryl (mono or bicyclic) rings in $R^{11p}$, $R^{12p}$, $R^i$ and ARp include halo, (1–4C)alkyl, hydroxy, nitro, carbamoyl, (1–4C)alkylcarbamoyl, di-((1–4C)alkyl)carbamoyl, cyano, trifluoromethyl, trifluoromethoxy, amino, (1–4C)alkylamino, di((1–4C)alkyl)amino, (1–4C)alkylS(O)$_q$—, (wherein q is 0, 1 or 2), carboxy, (1–4C)alkoxycarbonyl, (2–4C)alkenyl, (2–4C)alkynyl, (1–4C)alkanoyl, (1–4C)alkoxy, (1–4C)alkylS(O)$_2$amino, (1–4C)alkanoylamino, benzoylamino, benzoyl, phenyl (optionally substituted by up to three substituents selected from halo, (1–4C)alkoxy or cyano), furan, pyrrole, pyrazole, imidazole, triazole, pyrimidine, pyridazine, pyridine, isoxazole, oxazole, isothiazole, thiazole, thiophene, hydroxyimino (1–4C)alkyl, (1–4C)alkoxyimino(1–4C)alkyl, hydroxy-(1–4C)alkyl, halo-(1–4C)alkyl, nitro(1–4C)alkyl, amino (1–4C)alkyl, cyano(1–4C)alkyl, (1–4C)alkanesulfonamido, aminosulfonyl, (1–4C)alkylaminosulfonyl and di-((1–4C)alkyl)aminosulfonyl. The phenyl and naphthyl groups and heteroaryl (mono- or bicyclic) rings in $R^{11p}$, Ri and ARp may be mono- or disubstituted on ring carbon atoms with substituents independently selected from the above list of particular optional substituents.

For the avoidance of doubt, phosphono is —P(O)(OH)$_2$; (1–4C)alkoxy(hydroxy)-phosphoryl is a mono-(1–4C)alkoxy derivative of —O—P(O)(OH)$_2$; and di-(1–4C)alkoxyphosphoryl is a di-(1–4C)alkoxy derivative of —O—P(O)(OH)$_2$.

In this embodiment of formula (IP) a '5- or 6-membered heteroaryl' and 'heteroaryl (monocyclic) ring' means a 5- or 6-membered aryl ring wherein (unless stated otherwise) 1, 2 or 3 of the ring atoms are selected from nitrogen, oxygen and sulfur. Unless stated otherwise, such rings are fully aromatic. Particular examples of 5- or 6-membered heteroaryl ring systems are furan, pyrrole, pyrazole, imidazole, triazole, pyrimidine, pyridazine, pyridine, isoxazole, oxazole, isothiazole, thiazole and thiophene.

Particular examples of 5-membered heteroaryl rings containing 2 or 3 heteroatoms independently selected from N, O and S (with the proviso that there are no O—O, O—S or S—S bonds; and in an alternative embodiment, also no N—S bonds) are pyrazole, imidazole, 1,2,3-triazole, 1,2,4-triazole, oxazole, isoxazole, thiazole, 1,2,3-oxadiazole, 1,2,4-oxadiazole, 1,2,5-oxadiazole, 1,3,4-oxadiazole; and also in an alternative embodiment, isothiazole, 1,2,5-thiadiazole, 1,2,4-thiadiazole or 1,2,3-thiadiazole.

In this embodiment of formula (IP) a '5/6 or 6/6 bicyclic heteroaryl ring system' and 'heteroaryl (bicyclic) ring' means an aromatic bicyclic ring system comprising a 6-membered ring fused to either a 5 membered ring or another 6 membered ring, the bicyclic ring system containing 1 to 4 heteroatoms selected from nitrogen, oxygen and sulfur. Unless stated otherwise, such rings are fully aromatic. Particular examples of 5/6 and 6/6 bicyclic ring systems are indole, benzofuran, benzimidazole, benzothiophene, benzisothiazole, benzoxazole, benzisoxazole, pyridoimidazole, pyrimidoimidazole, quinoline, quinoxaline, quinazoline, phthalazine, cinnoline and naphthyridine.

Particular optional substituents for alkyl, phenyl (and phenyl containing moieties) and naphthyl groups and ring carbon atoms in heteroaryl (mono or bicyclic) rings in $R^{14p}$, $R^{15p}$, Ri and ARp include halo, (1–4C)alkyl, hydroxy, nitro, carbamoyl, (1–4C)alkylcarbamoyl, di-((1–4C)alkyl)carbamoyl, cyano, trifluoromethyl, trifluoromethoxy, amino, (1–4C)alkylamino, di((1–4C)alkyl)amino, (1–4C)alkyl S(O)$_q$ — (q is 0, 1 or 2), carboxy, (1–4C)alkoxycarbonyl, (2–4C)alkenyl, (2–4C)alkynyl, (1–4C)alkanoyl, (1–4C)alkoxy, (1–4C)alkylS(O)$_2$amino, (1–4C)alkanoylamino, benzoylamino, benzoyl, phenyl (optionally substituted by up to three substituents selected from halo, (1–4C)alkoxy or cyano), furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, hydroxy-(1–4C)alkyl, halo-(1–4C)alkyl, nitro(1–4C)alkyl, amino(1–4C)alkyl, cyano(1–4C)alkyl, (1–4C)alkanesulfonamido, aminosulfonyl, (1–4C)alkylaminosulfonyl and di-((1–4C)alkyl)aminosulfonyl. The phenyl and naphthyl groups and heteroaryl (mono- or bicyclic) rings in $R^{14p}$, R1 and ARp may be mono- or di-substituted on ring carbon atoms with substituents independently selected from the above list of particular optional substituents.

In this specification the term 'alkyl' includes straight chained and branched structures. For example, (1–6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1–4C) alkyl includes 1-bromoethyl and 2-bromoethyl.

There follow particular and suitable values for certain substituents and groups referred to in this specification. These values may be used where appropriate with any of the definitions and embodiments disclosed hereinbefore, or hereinafter.

Examples of (1–4C)alkyl and (1–5C)alkyl include methyl, ethyl, propyl, isopropyl and t-butyl; examples of (1–6C)alkyl include methyl, ethyl, propyl, isopropyl, t-butyl, pentyl and hexyl; examples of (1–10C)alkyl include methyl, ethyl, propyl, isopropyl, pentyl, hexyl, heptyl, octyl and nonyl; examples of (1–4C)alkanoylamino-(1–4C)alkyl include formamidomethyl, acetamidomethyl and acetamidoethyl; examples of hydroxy(1–4C)alkyl and hydroxy (1–6C)alkyl include hydroxymethyl, 1-hydroxyethyl, 2-hydroxyethyl and 3-hydroxypropyl; examples of (1–4C) alkoxycarbonyl include methoxycarbonyl, ethoxycarbonyl and propoxycarbonyl; examples of 2-((1–4C)alkoxycarbonyl)ethenyl include 2-(methoxycarbonyl)ethenyl and 2-(ethoxycarbonyl)ethenyl; examples of 2-cyano-2-((1–4C)alkyl)ethenyl include 2-cyano-2-methylethenyl and 2-cyano-2-ethylethenyl; examples of 2-nitro-2-((1–4C)alkyl)ethenyl include 2-nitro-2-methylethenyl and 2-nitro-2-ethylethenyl; examples of 2-((1–4C)alkylaminocarbonyl) ethenyl include 2-(methylaminocarbonyl)ethenyl and 2-(ethylaminocarbonyl)ethenyl; examples of (2–4C)alkenyl include allyl and vinyl; examples of (2–4C)alkynyl include ethynyl and 2-propynyl; examples of (1–4C)alkanoyl include formyl, acetyl and propionyl; examples of (1–4C) alkoxy include methoxy, ethoxy and propoxy; examples of (1–6C)alkoxy and (1–10C)alkoxy include methoxy, ethoxy, propoxy and pentoxy; examples of (1–4C)alkylthio include methylthio and ethylthio; examples of (1–4C)alkylamino include methylamino, ethylamino and propylamino; examples of di-((1–4C)alkyl)amino include dimethylamino, N-ethyl-N-methylamino, diethylamino, N-methyl-N-propylamino and dipropylamino; examples of halo groups include fluoro, chloro and bromo; examples of (1–4C)alkylsulfonyl include methylsulfonyl and ethylsulfonyl; examples of (1–4C)alkoxy-(1–4C)alkoxy and (1–6C)alkoxy-(1–6C) alkoxy include methoxymethoxy, 2-methoxyethoxy, 2-ethoxyethoxy and 3-methoxypropoxy; examples of (1–4C)alkoxy-(1–4C)alkoxy-(1–4C)alkoxy include 2-(methoxymethoxy)ethoxy, 2-(2-methoxyethoxy)ethoxy; 3-(2-methoxyethoxy)propoxy and 2-(2-ethoxyethoxy) ethoxy; examples of (1–4C)alkylS(O)$_2$amino include methylsulfonylamino and ethylsulfonylamino; examples of (1–4C)alkanoylamino and (1–6C)alkanoylamino include formamido, acetamido and propionylamino; examples of (1–4C)alkoxycarbonylamino include methoxycarbonylamino and ethoxycarbonylamino; examples of N-(1–4C) alkyl-N-(1–6C)alkanoylamino include N-methylacetamido, N-ethylacetamido and N-methylpropionamido; examples of (1–4C)alkylS(O)pNH— wherein p is 1 or 2 include methylsulfinylamino, methylsulfonylamino, ethylsulfinylamino and ethylsulfonylamino; examples of (1–4C)alkylS(O)$_p$ ((1–4C)alkyl)N— wherein p is 1 or 2 include methylsulfinylmethylamino, methylsulfonylmethylamino, 2-(ethylsulfinyl)ethylamino and 2-(ethylsulfonyl)ethylamino; examples of fluoro(1–4C)alkylS(O)$_p$NH— wherein p is 1 or 2 include trifluoromethylsulfinylamino and trifluoromethylsulfonylamino; examples of fluoro(1–4C)alkylS(O)$_p$ ((1–4C)alkyl)NH— wherein p is 1 or 2 include trifluoromethylsulfinylmethylamino and trifluoromethylsulfonylmethylamino examples of (1–4C) alkoxy(hydroxy)phosphoryl include methoxy(hydroxy) phosphoryl and ethoxy(hydroxy)phosphoryl; examples of di-(1–4C)alkoxyphosphoryl include di-methoxyphosphoryl, di-ethoxyphosphoryl and ethoxy(methoxy)phosphoryl; examples of (1–4C)alkylS(O)$_q$— wherein q is 0, 1 or 2 include methylthio, ethylthio, methylsulfinyl, ethylsulfinyl, methylsulfonyl and ethylsulfonyl; examples of phenylS(O)$_q$ and naphthylS(O)$_q$— wherein q is 0, 1 or 2 are phenylthio, phenylsulfinyl, phenylsulfonyl and naphthylthio, naphthylsulfinyl and naphthylsulfonyl respectively; examples of benzyloxy-(1–4C)alkyl include benzyloxymethyl and benzyloxyethyl; examples of a (3–4C)alkylene chain are trimethylene or tetramethylene; examples of (1–6C)alkoxy-(1–6C)alkyl include methoxymethyl, ethoxymethyl and 2-methoxyethyl; examples of hydroxy-(2–6C)alkoxy include 2-hydroxyethoxy and 3-hydroxypropoxy; examples of (1–4C)alkylamino-(2–6C)alkoxy include 2-methylaminoethoxy and 2-ethylaminoethoxy; examples of di-(1–4C) alkylamino-(2–6C)alkoxy include 2-dimethylaminoethoxy and 2-diethylaminoethoxy; examples of phenyl(1–4C)alkyl include benzyl and phenethyl; examples of (1–4C)alkylcarbamoyl include methylcarbamoyl and ethylcarbamoyl; examples of di((1–4C)alkyl)carbamoyl include di(methyl) carbamoyl and di(ethyl)carbamoyl; examples of hydroxyimino(1–4C)alkyl include hydroxyiminomethyl, 2-(hydroxyimino)ethyl and 1-(hydroxyimino)ethyl; examples of (1–4C)alkoxyimino-(1–4C)alkyl include methoxyiminomethyl, ethoxyiminomethyl, 1-(methoxyimino)ethyl and 2-(methoxyimino)ethyl; examples of halo(1–4C)alkyl include, halomethyl, 1-haloethyl, 2-haloethyl, and 3-halopropyl; examples of nitro(1–4C)alkyl include nitromethyl, 1-nitroethyl, 2-nitroethyl and 3-nitropropyl; examples of amino(1–4C)alkyl include aminomethyl, 1-aminoethyl, 2-aminoethyl and 3-aminopropyl; examples of cyano(1–4C)alkyl include cyanomethyl, 1-cyanoethyl, 2-cyanoethyl and 3-cyanopropyl; examples of (1–4C)alkanesulfonamido include methanesulfonamido and ethanesulfonamido; examples of (1–4C)alkylaminosulfonyl include methylaminosulfonyl and ethylaminosulfonyl; and examples of di-(1–4C)alkylaminosulfonyl include dimethylaminosulfonyl, diethylaminosulfonyl and N-methyl-N-ethylaminosulfonyl; examples of (1–4C)alkanesulfonyloxy include methylsulfonyloxy, ethylsulfonyloxy and propylsulfonyloxy; examples of (1–4C)alkanoyloxy include acetoxy; examples of (1–4C)alkylaminocarbonyl include methylaminocarbonyl and ethylaminocarbonyl; examples of di((1–4C)alkyl)aminocarbonyl include dimethylaminocarbonyl and diethylaminocarbonyl; examples of (3–8C)cycloalkyl include cyclopropyl, cyclobutyl, cyclopentyl and cyclohexyl; examples of (4–7C)cycloalkyl include cyclobutyl, cyclopentyl and cyclohexyl; examples of di(N-(1–4C)alkyl)aminomethylimino include dimethylaminomethylimino and iethylaminomethylimino.

Particular values for AR2 include, for example, for those AR2 containing one heteroatom, furan, pyrrole, thiophene; for those AR2 containing one to four N atoms, pyrazole, imidazole, pyridine, pyrimidine, pyrazine, pyridazine, 1,2,3- & 1,2,4-triazole and tetrazole; for those AR2 containing one N and one O atom, oxazole, isoxazole and oxazine; for those AR2 containing one N and one S atom, thiazole and isothiazole; for those AR2 containing two N atoms and one S atom, 1,2,4- and 1,3,4-thiadiazole.

Particular examples of AR2a include, for example, dihydropyrrole (especially 2,5-dihydropyrrol-4-yl) and tetrahydropyridine (especially 1,2,5,6-tetrahydropyrid-4-yl).

Particular examples of AR2b include, for example, tetrahydrofuran, pyrrolidine, morpholine (preferably morpholino), thiomorpholine (preferably thiomorpholino), piperazine (preferably piperazino), imidazoline and piperidine, 1,3-dioxolan-4-yl, 1,3-dioxan-4-yl, 1,3-dioxan-5-yl and 1,4-dioxan-2-yl.

Particular values for AR3 include, for example, bicyclic benzo-fused systems containing a 5- or 6-membered heteroaryl ring containing one nitrogen atom and optionally 1–3 further heteroatoms chosen from oxygen, sulfur and nitrogen. Specific examples of such ring systems include, for example, indole, benzofuran, benzothiophene, benzimidazole, benzothiazole, benzisothiazole, benzoxazole, benzisoxazole, quinoline, quinoxaline, quinazoline, phthalazine and cinnoline.

Other particular examples of AR3 include 5/5-, 5/6 and 6/6 bicyclic ring systems containing heteroatoms in both of the rings. Specific examples of such ring systems include, for example, purine and naphthyridine.

Further particular examples of AR3 include bicyclic heteroaryl ring systems with at least one bridgehead nitrogen and optionally a further 1–3 heteroatoms chosen from oxygen, sulfur and nitrogen. Specific examples of such ring systems include, for example, 3H-pyrrolo[1,2-a]pyrrole, pyrrolo[2,1-b]thiazole, 1H-imidazo[1,2-a]pyrrole, 1H-imidazo[1,2-a]imidazole, 1H,3H-pyrrolo[1,2-c]oxazole, 1H-imidazo[1,5-a]pyrrole, pyrrolo[1,2-b]isoxazole, imidazo[5,1-b]thiazole, imidazo[2,1-b]thiazole, indolizine, imidazo[1,2-a]pyridine, imidazo[1,5-a]pyridine, pyrazolo[1,5-a]pyridine, pyrrolo[1,2-b]pyridazine, pyrrolo[1,2-c]pyrimidine, pyrrolo[1,2-a]pyrazine, pyrrolo[1,2-a]pyrimidine, pyrido[2,1-c]-s-triazole, s-triazole[1,5-a]pyridine, imidazo[1,2-c]pyrimidine, imidazo[1,2-a]pyrazine, imidazo[1,2-a]pyrimidine, imidazo[1,5-a]pyrazine, imidazo[1,5-a]pyrimidine, imidazo[1,2-b]-pyridazine, s-triazolo[4,3-a]pyrimidine, imidazo[5,1-b]oxazole and imidazo[2,1-b]oxazole. Other specific examples of such ring systems include, for example, [1H]-pyrrolo[2,1-c]oxazine, [3H]-oxazolo[3,4-a]pyridine, [6H]-pyrrolo[2,1-c]oxazine and pyrido[2,1-c][1,4]oxazine. Other specific examples of 5/5- bicyclic ring systems are imidazooxazole or imidazothiazole, in particular imidazo[5,1-b]thiazole, imidazo[2,1-b]thiazole, imidazo[5,1-b]oxazole or imidazo[2,1-b]oxazole.

Particular examples of AR3a and AR3b include, for example, indoline, 1,3,4,6,9,9a-hexahydropyrido[2,1c][1,4] oxazin-8-yl, 1,2,3,5,8,8a-hexahydroimidazo[1,5a]pyridin-7-yl, 1,5,8,8a-tetrahydrooxazolo[3,4a]pyridin-7-yl, 1,5,6,7,8,8a-hexahydrooxazolo[3,4a]pyridin-7-yl, (7aS)[3H,5H]-1,7a-dihydropyrrolo[1,2c]oxazol-6-yl, (7aS)[5H]-1,2,3,7a-tetrahydropyrrolo[1,2c]imidazol-6-yl, (7aR)[3H,5H]-1,7a-dihydropyrrolo[1,2c]oxazol-6-yl, [3H,5H]-pyrrolo[1,2-c]oxazol-6-yl, [5H]-2,3-dihydropyrrolo[1,2-c]imidazol-6-yl, [3H,5H]-pyrrolo[1,2-c]thiazol-6-yl, [3H,5H]-1,7a-dihydropyrrolo[1,2-c]thiazol-6-yl, [5H]-pyrrolo[1,2-c]imidazol-6-yl, [1H]-3,4,8,8a-tetrahydropyrrolo[2,1-c]oxazin-7-yl, [3H]-1,5,8,8a-tetrahydrooxazolo[3,4-a]pyrid-7-yl, [3H]-5,8-dihydroxazolo[3,4-a]pyrid-7-yl and 5,8-dihydroimidazo[1,5-a]pyrid-7-yl.

Particular values for AR4 include, for example, pyrrolo[a]quinoline, 2,3-pyrroloisoquinoline, pyrrolo[a]isoquinoline, 1H-pyrrolo[1,2-a]benzimidazole, 9H-imidazo[1,2-a]indole, 5H-imidazo[2,1-a]isoindole, 1H-imidazo[3,4-a]indole, imidazo[1,2-a]quinoline, imidazo[2,1-a]isoquinoline, imidazo[1,5-a]quinoline and imidazo[5,1-a]isoquinoline.

Particular values of AR4a include partially hydrogenated version of those AR4 values listed immediately above.

The nomenclature used is that found in, for example, "Heterocyclic Compounds (Systems with bridgehead nitrogen), W. L. Mosby (Intercsience Publishers Inc., New York), 1961, Parts 1 and 2.

Where optional substituents are listed such substitution is preferably not geminal disubstitution unless stated otherwise. If not stated elsewhere suitable optional substituents for a particular group are those as stated for similar groups herein.

Suitable substituents on AR1, AR2, AR2a, AR2b, AR3, AR3a, AR3b, AR4, AR4a, CY1 and CY2 are (on an available carbon atom) up to three substituents independently selected from (1–4C)alkyl {optionally substituted by (preferably one) substituents selected independently from hydroxy, trifluoromethyl, (1–4C)alkyl S(O)$_q$— (q is 0, 1 or 2) (this last substituent preferably on AR1 only), (1–4C)alkoxy, (1–4C)alkoxycarbonyl, cyano, nitro, (1–4C)alkanoylamino, —CONRvRw or —NRvRw}, trifluoromethyl, hydroxy, halo, nitro, cyano, thiol, (1–4C)alkoxy, (1–4C)alkanoyloxy, dimethylaminomethyleneaminocarbonyl, di(N-(1–4C)alkyl)aminomethylimino, carboxy, (1–4C)alkoxycarbonyl, (1–4C)alkanoyl, (1–4C)alkylSO$_2$amino, (2–4C)alkenyl {optionally substituted by carboxy or (1–4C)alkoxycarbonyl}, (2–4C)alkynyl, (1–4C)alkanoylamino, oxo (=O), thioxo (=S), (1–4C)alkanoylamino {the (1–4C)alkanoyl group being optionally substituted by hydroxy}, (1–4C)alkyl S(O)$_q$— (q is 0, 1 or 2) {the (1–4C)alkyl group being optionally substituted by one or more groups independently selected from cyano, hydroxy and (1–4C)alkoxy}, —CONRvRw or —NRvRw [wherein Rv is hydrogen or (1–4C)alkyl; Rw is hydrogen or (1–4C)alkyl].

Further suitable substituents on AR1, AR2, AR2a, AR2b, AR3, AR3a, AR3b, AR4, AR4a, CY1 and CY2 (on an available carbon atom), and also on alkyl groups (unless indicated otherwise) are up to three substituents independently selected from trifluoromethoxy, benzoylamino, benzoyl, phenyl {optionally substituted by up to three substituents independently selected from halo, (1–4C)alkoxy or cyano}, furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, halo-(1–4C)alkyl, (1–4C)alkanesulfonamido, —SO$_2$NRvRw [wherein Rv is hydrogen or (1–4C)alkyl; Rw is hydrogen or (1–4C)alkyl].

Preferable optional substituents on Ar2b as 1,3-dioxolan-4-yl, 1,3-dioxan-4-yl, 1,3-dioxan-5-yl or 1,4-dioxan-2-yl are mono- or disubstitution by substituents independently selected from (1–4C)alkyl (including geminal disubstitution), (1–4C)alkoxy, (1–4C)alkylthio, acetamido, (1–4C)alkanoyl, cyano, trifluoromethyl and phenyl].

Preferable optional substituents on CY1 & CY2 are mono- or disubstitution by substituents independently selected from (1–4C)alkyl (including geminal disubstitution), hydroxy, (1–4C)alkoxy, (1–4C)alkylthio, acetamido, (1–4C)alkanoyl, cyano, and trifluoromethyl.

Suitable substituents on AR2, AR2a, AR2b, AR3, AR3a, AR3b, AR4 and AR4a are (on an available nitrogen atom, where such substitution does not result in quaternization) (1–4C)alkyl, (1–4C)alkanoyl {wherein the (1–4C)alkyl and (1–4C)alkanoyl groups are optionally substituted by (preferably one) substituents independently selected from cyano, hydroxy, nitro, trifluoromethyl, (1–4C)alkyl S(O)$_q$— (q is 0, 1 or 2), (1–4C)alkoxy, (1–4C)alkoxycarbonyl, (1–4C)alkanoylamino, —CONRvRw or —NRvRw [wherein Rv is hydrogen or (1–4C)alkyl; Rw is hydrogen or (1–4C)alkyl]}, (2–4C)alkenyl, (2–4C)alkynyl, (1–4C)alkoxycarbonyl or oxo (to form an N-oxide).

Suitable pharmaceutically-acceptable salts include acid addition salts such as methanesulfonate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the formula (I) or a pharmaceutically-acceptable salt thereof.

Various forms of prodrugs are known in the art, for examples see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984).

An in-vivo hydrolysable ester of a compound of the formula (I) or a pharmaceutically-acceptable salt thereof containing carboxy or hydroxy group is, for example, a pharmaceutically-acceptable ester which is hydrolysed in the human or animal body to produce the parent acid or alcohol. Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C)cycloalkoxycarbonyloxy(1–6C)alkyl esters for example 1-cyclohexylcarbonyloxyethyl; 1,3-dioxolan-2-onylmethyl esters for example 5-methyl-1,3-dioxolan-2-ylmethyl; and (1–6C) alkoxycarbonyloxyethyl esters for example 1-methoxycarbonyloxyethyl and may be formed at any carboxy group in the compounds of this invention.

An in-vivo hydrolysable ester of a compound of the formula (I) or a pharmaceutically-acceptable salt thereof containing a hydroxy group or groups includes inorganic esters such as phosphate esters (including phosphoramidic cyclic esters) and di-1–4C-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1–10C)alkanoyl, benzoyl, phenylacetyl and substituted benzoyl and phenylacetyl, (1–10C)alkoxycarbonyl (to give alkyl carbonate esters), di-(1–4C)alkylcarbamoyl and N-(di-(1–4C)alkylaminoethyl)-N-(1–4C)alkylcarbamoyl (to give carbamates), di-(1–4C)alkylaminoacetyl and carboxyacetyl. Examples of ring substituents on phenylacetyl and benzoyl include chloromethyl or aminomethyl, (1–4C)alkylaminomethyl and di-((1–4C)alkyl)aminomethyl, and morpholino or piperazino linked from a ring nitrogen atom via a methylene linking group to the 3- or 4-position of the benzoyl ring.

Certain suitable in-vivo hydrolysable esters of a compound of the formula (I) are described within the definitions listed in this specification, for example esters described by the definition (Rc2d), and some groups within (Rc2c). Suitable in-vivo hydrolysable esters of a compound of the formula (I) are described as follows. For example, a 1,2-diol may be cyclised to form a cyclic ester of formula (PD1) or a pyrophosphate of formula (PD2)

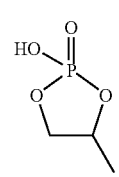

(PD1)

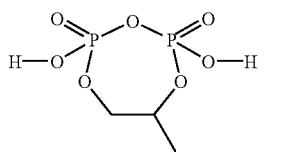

(PD2)

Particularly interesting are such cyclised pro-drugs when the 1,2-diol is on a (1–4C)alkyl chain linked to a carbonyl group in a substituent of formula Rc borne by a nitrogen atom in (TC4). Esters of compounds of formula (I) wherein the HO— function/s in (PD1) and (PD2) are protected by (1–4C)alkyl, phenyl or benzyl are useful intermediates for the preparation of such pro-drugs.

Further in-vivo hydrolysable esters include phosphoramidic esters, and also compounds of formula (I) in which any free hydroxy group independently forms a phosphoryl (npd is 1) or phosphiryl (npd is 0) ester of the formula (PD3):

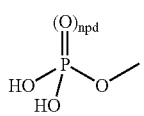

(PD3)

Useful intermediates for the preparation of such esters include compounds containing a group/s of formula (PD3) in which either or both of the —OH groups in (PD3) is independently protected by (1–4C)alkyl (such compounds also being interesting compounds in their own right), phenyl or phenyl-(1–4C)alkyl (such phenyl groups being optionally substituted by 1 or 2 groups independently selected from (1–4C)alkyl, nitro, halo and (1–4C)alkoxy).

Thus, prodrugs containing groups such as (PD1), (PD2) and (PD3) may be prepared by reaction of a compound of formula (I) containing suitable hydroxy group/s with a suitably protected phosphorylating agent (for example, containing a chloro or dialkylamino leaving group), followed by oxidation (if necessary) and deprotection.

When a compound of formula (I) contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities.

Other interesting in-vivo hydrolysable esters include, for example, those in which Rc is defined by, for example, $R^{14}C(O)O(1–6C)alkyl-CO$— (wherein $R^{14}$ is for example, benzyloxy-(1–4C)alkyl, or phenyl). Suitable substituents on a phenyl group in such esters include, for example, 4-(1–4C) piperazino-(1–4C)alkyl, piperazino-(1–4C)alkyl and morpholino-(1–4C)alkyl.

Where pharmaceutically-acceptable salts of an in-vivo hydrolysable ester may be formed this is achieved by conventional techniques. Thus, for example, compounds containing a group of formula (PD1), (PD2) and/or (PD3) may ionise (partially or fully) to form salts with an appropriate number of counter-ions. Thus, by way of example, if an in-vivo hydrolysable ester prodrug of a compound of formula (I) contains two (PD3) groups, there are four HO—P— functionalities present in the overall molecule, each of which may form an appropriate salt (i.e. the overall molecule may form, for example, a mono-, di-, tri- or tetra-sodium salt).

The compounds of the present invention have a chiral centre at the C-5 position of the oxazolidinone ring. The pharmaceutically active enantiomer is of the formula (IA):

(IA)

The present invention includes the pure enantiomer depicted above or mixtures of the 5R and 5S enantiomers, for example a racemic mixture. If a mixture of enantiomers is used, a larger amount (depending upon the ratio of the enantiomers) will be required to achieve the same effect as the same weight of the pharmaceutically active enantiomer. For the avoidance of doubt the enantiomer depicted above is generally the 5(R) enantiomer, although certain compounds (such as HET as pyrid-2-one) are the 5(S) enantiomer. Examples of 5(S) compounds are illustrated in the accompanying non-limiting Examples.

Furthermore, some compounds of the formula (I) may have other chiral centres. It is to be understood that the invention encompasses all such optical and diastereo-isomers, and racemic mixtures, that possess antibacterial activity. It is well known in the art how to prepare optically-active forms (for example by resolution of the racemic form by recrystallisation techniques, by chiral synthesis, by enzymatic resolution, by biotransformation or by chromatographic separation) and how to determine antibacterial activity as described hereinafter.

The invention relates to all tautomeric forms of the compounds of the formula (I) that possess antibacterial activity.

It is also to be understood that certain compounds of the formula (I) can exist in solvated as well as unsolvated forms such as, for example, hydrated forms. It is to be understood that the invention encompasses all such solvated forms which possess antibacterial activity.

It is also to be understood that certain compounds of the formula (I) may exhibit polymorphism, and that the invention encompasses all such forms which possess antibacterial activity.

As stated before, we have discovered a range of compounds that have good activity against a broad range of Gram-positive pathogens including organisms known to be resistant to most commonly used antibiotics. Physical and/or pharmacokinetic properties, for example increased stability to mammalian peptidase metabolism and a favourable toxicological profile are important features. The following compounds possess favourable physical and/or pharmacokinetic properties and are preferred.

Particularly preferred compounds of the invention comprise a compound of formula (I) or of formula (IP), or a pharmaceutically-acceptable salt or an in-vivo hydrolysable ester thereof, wherein the substituents Q, HET, T and other substituents mentioned above have values disclosed hereinbefore, or any of the following values (which may be used where appropriate with any of the definitions and embodiments disclosed hereinbefore or hereinafter):

Preferably Q is selected from Q1, Q2, Q4, Q6 and Q9; especially Q1, Q2 and Q9; more particularly Q1 and Q2; and most preferably Q is Q1.

Preferably T is selected from (TAf), (TDb) or (TC); especially groups (TAf2), (TCb) and (TCc); more particularly (TC2), (TC3) and (TC4); and most preferably (TC5), (TC7) or (TC9), and most particularly (TC9) and (TC5). Especially preferred is each of these values of T when present in Q1 and Q2, particularly in Q1.

Preferable values for other substituents (which may be used where appropriate with any of the definitions and embodiments disclosed hereinbefore or hereinafter) are:—

(a0) In one embodiment HET is a 6-membered heteroaryl ring as defined herein, and in another embodiment HET is a 5-membered heteroaryl ring as defined herein. Preferably HET is a 5-membered heteroaryl as defined herein.

In this specification it will be appreciated that when HET is a 5-membered heteroaryl ring, the ring must be aromatic and that when HET is a 6-membered heteroaryl ring, the ring system (which contains the optimum number of double bonds) can necessarily only be pseudoaromatic. It will also be appreciated that when HET as an N-linked 5-membered heteroaryl ring is optionally substituted on an available carbon atom by oxo or thioxo then, when HET contains 1 to 3 further nitrogen heteroatoms, one of the further nitrogen heteroatoms is present as NH or as N-(1–4C)alkyl. Similarly, when HET as an N-linked 5-membered heteroaryl ring is optionally substituted on an available nitrogen atom by (1–4C)alkyl then the ring is substituted on an available carbon atom by oxo or thioxo.

(a) When HET is a 6-membered heteroaryl as defined herein, preferably HET is pyridine or pyridazine; preferably with a 2-oxo substituent.

(b) When HET is a 5-membered heteroaryl as defined herein, preferably HET contains only nitrogen heteroatoms or is thiadiazole or thiazole.

(c) Yet more preferably HET is triazole, tetrazole or imidazole, especially triazole or tetrazole, and most especially triazole.

(d) Further preferred as HET is 1,2,3-triazole and 1,2,4-triazole, especially 1,2,3-triazole, and most especially 1,2,3-triazol-1-yl.

(e) Further preferred as HET is 1,2,3,4-tetrazole, especially 1,2,3,4-tetrazol-2-yl.

(f) Most preferred is HET as 1,2,3-triazol-1-yl.

(g) Preferably HET (when a 5-membered ring) is unsubstituted.

(h) Preferably $R^{6p}$ is hydrogen;

(i) Preferably $R^{4p}$ and $R^{5p}$ are independently selected from hydrogen, (1–4C)alkyl, carboxy, (1–4C)alkoxycarbonyl, hydroxymethyl, (1–4C)alkoxymethyl or carbamoyl;

(j) More preferably $R^{4p}$ and $R^{5p}$ are hydrogen;

(k) Preferably $R^2$ and $R^3$ are hydrogen or fluoro;

(l) In one aspect of the invention more preferably one of $R^2$ and $R^3$ is hydrogen and the other fluoro. In another aspect of the invention both $R^2$ and $R^3$ are fluoro;

(m) Preferably >A—B— is of the formula >C=CH— (i.e. $R^a$ is preferably hydrogen) or >N—CH$_2$—;

(n) Preferably D is O or NR$^{7p}$; (O) Preferably $R^{7p}$ is ARp, $R^{10p}CO$—, $R^{10p}SO_2$—, $R^{10p}CS$—;

(p) More preferably $R^{7p}$ is ARp (most preferably benzyl, pyrimidyl, pyridinyl, pyridazinyl or pyrazinyl) or $R^{10p}CO$—;

(q) Particularly $R^{7p}$ is $R^{10p}CO$—;

(q1) Especially preferred is $R^{10p}CO$— (or $R^{13}CO$—) wherein $R^{10p}$ (or $R^{13}$) is (1–10)alkyl optionally substituted by hydroxy or (1–4C)alkylS(O)$_q$— (wherein q is 0, 1 or 2), wherein the (1–4C)alkyl group is optionally substituted as defined herein for this particular substituent;

(r) Preferably ARp is 5- or 6-membered heteroaryl; more preferably ARp is 6-membered heteroaryl, such as pyridinyl;

(s) Preferred substituents for phenyl and carbon atoms in heteroaryl (mono- and bicyclic) ring systems in ARp, $R^{11p}$ and R include halo, (1–4C)alkyl, hydroxy, nitro, amino, cyano, (1–4C)alkylS(O)$_p$— and (1–4C)alkoxy;

(t) Preferably the optionally substituted ring systems in ARp, $R^{11p}$ and $R^i$ are unsubstituted;

(u) In another embodiment in the definition of $R^{10p}$ in (PC) of embodiment (IP), 1,3-dioxolan-4-yl and 1,4-dioxan-2-yl are excluded.

(v) In one aspect of the invention, preferably $R^{10p}$ is (1–4C)alkoxycarbonyl, hydroxy(1–4C)alkyl, (1–4C)alkyl (optionally substituted by one or two hydroxy groups, or by an (1–4C)alkanoyl group), (1–4C)alkylamino, dimethylamino (1–4C)alkyl, (1–4C)alkoxymethyl, (1–4C)alkanoylmethyl, (1–4C)alkanoyloxy(1–4C)alkyl, (1–5C)alkoxy or 2-cyanoethyl;

(w) In one aspect of the invention, more preferably $R^{10p}$ is 1,2-dihydroxyethyl, 1,3-dihydroxyprop-2-yl, 1,2,3-trihydroxyprop-1-yl, methoxycarbonyl, hydroxymethyl, methyl, methylamino, dimethylaminomethyl, methoxymethyl, acetoxymethyl, methoxy, methylthio, naphthyl, tert-butoxy or 2-cyanoethyl;

(x) In one aspect of the invention, particularly $R^{10p}$ is 1,2-dihydroxyethyl, 1,3-dihydroxyprop-2-yl or 1,2,3-trihydroxyprop-1-yl;

(y) In another aspect of the invention preferably $R^{10p}$ is hydrogen, (1–10C)alkyl [optionally substituted by one or more hydroxy] or $R^{11p}$ C(O)O(1–6C)alkyl.

(z) In another aspect of the invention, more preferably $R^{10p}$ is hydrogen, hydroxymethyl, 1,2-dihydroxyethyl or acteoxyacetyl; and/or Rc2c is (1–10C)alkyl optionally substituted by (1–4C)alkyl S(O)$_q$-(q is 0–2), optionally substituted as in claim 1.

(aa) Preferably $R^{11p}$ is (1–10C)alkyl;

(ab) Preferred optional substituents for (1–10C)alkyl in $R^{11p}$ are hydroxy, cyano, amino, (1–4C)alkylamino, di((1–4C)alkyl)amino, (1–4C)alkylS(O)p (wherein p is 1 or 2), carboxy, (1–4C)alkoxycarbonyl, (1–4C)alkoxy, piperazino or morpholino;

(ac) Preferred optional substituents for (1–6C)alkyl in $R^{12p}$ are hydroxy, (1–4C)alkoxy, cyano, amino, (1–4C)alkylamino, di((1–2C)alkyl)amino, (1–4C)alkylS(O)$_p$— (wherein p is 1 or 2);

(ad) Preferably 5- or 6-membered heteroaryl in $R^{11p}$ is pyridinyl or imidazol-1-yl;

(ae) Preferably $R^{12p}$ is (1–6C)alkyl; most preferably $R^{12p}$ is tert-butyl or methyl;

(af) Preferably $R^{13p}$ is cyano or fluoro;

(ag) Preferably $R^{14p}$ is hydrogen;

(ah) Preferably CYp is naphthoxy, especially naphth-1-oxy or naphth-2-oxy.

Where preferable values are given for substituents in a compound of formula (IP), the corresponding substituents in a compound of formula (I) have the same preferable values (thus, for example, Rc and $R^{13}$ in formula (I) correspond with $R^{7p}$ and $R^{10p}$ in formula (IP), and similarly for groups D and G). The preferred values of $R^{7p}$, for example, defined with reference to (IP) are also preferred values of Rc and may be used as preferred values of Rc in any compound of formula (I). For compounds of formula (I) preferred values for Rc are those in group (Rc2) when present in any of the definitions herein containing Rc—for example when present in compounds in which there is a (TC5) or (TC9) ring system. The preferred values for $R^{10p}$ listed above for compounds of formula (IP) are also preferred values for $R^{13}$ in compounds of formula (I). In the definition of (Rc2c) the AR2a, AR2b, AR3a and AR3b versions of AR2 and AR3 containing groups are preferably excluded.

Particularly, HET (when substituted) is selected from the following 7 rings (HET-P1 to HET-P7)

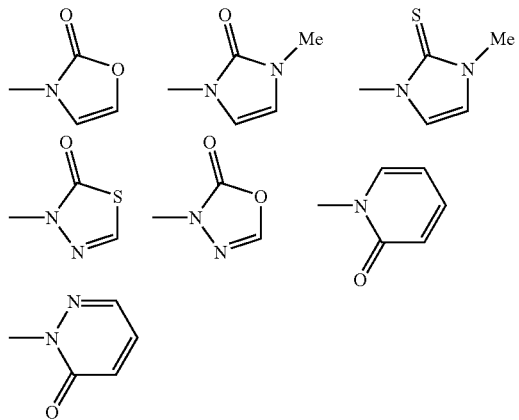

The above HET definitions are especially preferred in embodiment (IP).

Especially preferred compounds of the present invention are of the formula (IB):

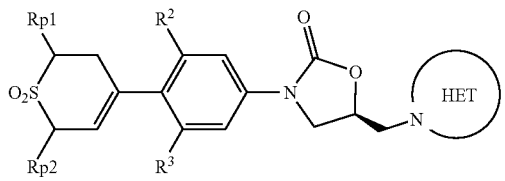

wherein HET is triazole or tetrazole, and most especially triazole; $R^2$ and $R^3$ are independently hydrogen or fluoro; and Rp1 and Rp2 are independently hydrogen, hydroxy, bromo, (1–4C)alkyl, carboxy, (1–4C)alkoxycarbonyl, hydroxymethyl, (1–4C)alkoxymethyl or carbamoyl; or pharmaceutically-acceptable salts thereof.

Further especially preferred compounds of the invention are of the formula (IB) wherein HET is wherein HET is triazole or tetrazole, and most especially triazole; $R^2$ and $R^3$ are independently hydrogen or fluoro; and Rp1 and Rp2 are independently hydrogen, AR-oxymethyl or AR-thiomethyl (wherein AR is phenyl, phenyl-(1–4C)alkyl, naphthyl, furan, pyrrole, pyrazole, imidazole, triazole, pyrimidine, pyridazine, pyridine, isoxazole, oxazole, isothiazole, thiazole or thiophene); or pharmaceutically-acceptable salts thereof.

Of the above especially preferred compounds of the invention of the formula (IB), particularly preferred compounds are those wherein Rp1 and Rp2 are hydrogen are particularly preferred.

Further especially preferred compounds of the present invention are of the formula (IB-1):

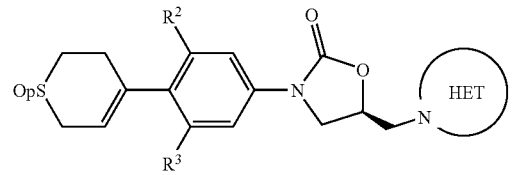

wherein HET is triazole or tetrazole, and most especially triazole (particularly 1,2,3-triazole, and especially 1,2,3-triazol-1-yl); $R^2$ and $R^3$ are independently hydrogen or fluoro and p is 1 or 2.

Further, especially preferred compounds of the invention are of the formula (IC):

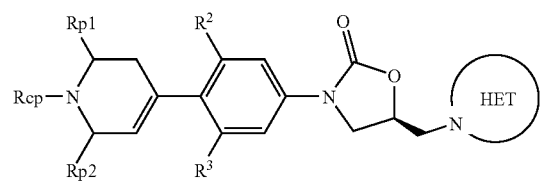

wherein HET is triazole or tetrazole, and most especially triazole; $R^2$ and $R^3$ are independently hydrogen or fluoro; Rp1 and Rp2 are independently hydrogen, AR-oxymethyl or AR-thiomethyl (wherein AR is phenyl, phenyl-(1–4C)alkyl, naphthyl, furan, pyrrole, pyrazole, imidazole, triazole, pyrimidine, pyridazine, pyridine, isoxazole, oxazole, isothiazole, thiazole or thiophene), (1–4C)alkyl, carboxy, (1–4C)alkoxycarbonyl, hydroxymethyl, (1–4C)alkoxymethyl or carbamoyl and Rcp is cyano, pyrimidin-2-yl, 2-cyanoethenyl, 2-cyano-2-((1–4C)alkyl)ethenyl or Rcp is of the formula $R^{10p}CO$—, $R^{10p}SO_2$— or $R^{10p}CS$— (wherein $R^{10p}$ is hydrogen, (1–5C)alkyl [optionally substituted by one or more groups each independently selected from hydroxy and amino, or optionally monosubstituted by (1–4C)alkoxy, (1–4C)alkylS(O)q—, (1–4C)alkylamino, (1–4C)alkanoyl, naphthoxy, (2–6C)alkanoylamino or (1–4C)alkylS(O) pNH— wherein p is 1 or 2 and q is 0, 1 or 2], imidazole, triazole, pyrimidine, pyridazine, pyridine, isoxazole, oxazole, isothiazole, thiazole, pyridoimidazole, pyrimidoimidazole, quinoxaline, quinazoline, phthalazine, cinnoline or naphthyridine, or $R^{10p}$ is of the formula $R^{11p}$ C(O)O(1–6C)alkyl wherein $R^{11p}$ is (1–6C)alkyl), or Rcp is of the formula RfC(=O)C(=O)— wherein Rf is (1–6C)alkoxy; or pharmaceutically-acceptable salts thereof.

Of the above especially preferred compounds of the invention of the formula (IC), those wherein HET is triazole or tetrazole, and most especially triazole; $R^2$ and $R^3$ are independently hydrogen or fluoro; Rp1 and Rp2 are independently hydrogen, AR-oxymethyl or AR-thiomethyl (wherein AR is phenyl, phenyl-(1–4C)alkyl, naphthyl, furan, pyrrole, pyrazole, imidazole, triazole, pyrimidine, pyridazine, pyridine, isoxazole, oxazole, isothiazole, thiazole or thiophene), (1–4C)alkyl, carboxy, (1–4C)alkoxycarbonyl, hydroxymethyl, (1–4C)alkoxymethyl or carbamoyl and Rcp is cyano, pyrimidin-2-yl, 2-cyanoethenyl, 2-cyano-2-((1–4C)alkyl)ethenyl or Rcp is of the formula $R^{10p}$CO—, $R^{10p}$SO$_2$— or $R^{10p}$CS— (wherein $R^{10p}$ is hydrogen, (1–5C) alkyl [optionally substituted by one or more groups each independently selected from hydroxy and amino, or optionally monosubstituted by (1–4C)alkoxy, (1–4C)alkylS(O)$_q$, (1–4C)alkylamino, (1–4C)alkanoyl, (2–6C)alkanoylamino or (1–4C)alkylS(O)pNH— wherein p is 1 or 2 and q is 0, 1 or 2], pyridine, or $R^{10p}$ is of the formula $R^{11p}$C(O)O(1–6C) alkyl wherein $R^{11p}$ is (1–6C)alkyl), or Rcp is of the formula RfC(=O)C(=O)— wherein Rf is (1–6C)alkoxy; or pharmaceutically-acceptable salts thereof are further preferred.

Of the above especially preferred compounds of the invention of the formula (IC), particularly preferred compounds are those wherein HET is triazole or tetrazole, and most especially triazole; $R^2$ and $R^3$ are independently hydrogen or fluoro; Rp1 and Rp2 are hydrogen, and Rcp is pyridin-2-yl (optionally substituted with cyano) or Rcp is of the formula $R^{10p}$CO— (wherein $R^{10p}$ is hydrogen, 1,3-dioxolan-4-yl (optionally disubstituted with (1–4C)alkyl) or (1–5C)alkyl [optionally substituted by one or more hydroxy groups] or $R^{10p}$ is of the formula $R^{11p}$C(O)O(1–6C)alkyl wherein $R^{11p}$ is (1–6C)alkyl)); or pharmaceutically-acceptable salts thereof.

Of the above especially preferred compounds of the invention of the formula (IC), particularly preferred compounds are those wherein Rcp is of the formula $R^{10p}$CO— (wherein $R^{10p}$ is hydrogen, 1,3-dioxolan-4-yl (optionally disubstituted with (1–4C)alkyl) or (1–5C)alkyl [substituted by two hydroxy groups, e.g. 2,3-dihydroxypropanoyl or by one hydroxy group, e.g. hydroxyacetyl]; or pharmaceutically-acceptable salts thereof.

In another aspect of the invention particularly preferred compounds of the invention are of the formula (IC) wherein HET is triazole or tetrazole, and most especially triazole; $R^2$ and $R^3$ are independently hydrogen or fluoro; Rp1 and Rp2 are hydrogen and Rcp is $R^{10p}$CO— (wherein $R^{10p}$ is hydrogen, (1–5C)alkyl [optionally substituted by one or two hydroxy groups], or $R^{10p}$ is of the formula $R^{11p}$ C(O)O (1–6C)alkyl (wherein $R^{11p}$ is (1–6C)alkyl)); and pharmaceutically-acceptable salts thereof.

In another aspect of the invention all of the compounds of formula (IB) or (IC) described above are further preferred when HET is triazole.

In yet another aspect the invention relates to all of the compounds of formula (IB) or (IC) described above wherein HET is 1,2,3-triazol-1-yl.

In another aspect of the invention there are provided preferred compounds of the formula (IP) wherein HET is triazole or tetrazole, and most especially triazole; >A—B— is >N—CH$_2$— and D is NR$^{7p}$ (or D is O) wherein Rcp is a 6-membered heteroaryl ring containing 1, 2 or 3 ring nitrogen atoms as the only ring heteroatoms, linked via a ring carbon atom and optionally substituted on a ring carbon atom by one, two or three substituents independently selected from (1–4C)alkyl, halo, trifluoromethyl, (1–4C)alkyl S(O)$_q$— (wherein q is 0, 1 or 2), (1–4C)alkylS(O)$_2$ amino, (1–4C)alkanoylamino, carboxy, hydroxy, amino, (1–4C)alkylamino, di-(1–4C)alkylamino, (1–4C)alkoxycarbonyl, carbamoyl, N-(1–4C)alkylcarbamoyl, di-(N-(1–4C)alkyl)carbamoyl, (1–4C)alkoxy, cyano or nitro; or pharmaceutically-acceptable salts thereof.

In yet another aspect the invention relates to all of the compounds of formula (IP) described immediately above wherein >A—B— is >N—CH$_2$— and D is NR$^{7p}$ and wherein HET is triazole or tetrazole, and most especially triazole.

In all of the above aspects and preferred compounds of formula (IB) or (IC), in-vivo hydrolysable esters are preferred where appropriate, especially phosphoryl esters (as defined by formula (PD3) with npd as 1).

In all of the above definitions the preferred compounds are as shown in formula (IA), i.e. the pharmaceutically active (5(R)) enantiomer.

Particular compounds of the present invention include the compounds of Examples 34b, 44a, 52, 54, 56, 58, 64 and 74 (wherein "a" refers to the first named compound, and "b" the second named compound in the Example title); or pharmaceutically-acceptable salts thereof. Particularly preferred salts are the sodium salts. In-vivo hydrolysable esters, or pharmaceutically-acceptable salts thereof, of Examples with hydroxy groups are also preferred, especially phosphoryl esters.

Process section:

In a further aspect the present invention provides a process for preparing a compound of formula (I) or a pharmaceutically-acceptable salt or an in-vivo hydrolysable ester thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide.

Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a 1-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

A compound of the formula (I), or a pharmaceutically-acceptable salt or an in vivo hydrolysable ester thereof, may be prepared by any process known to be applicable to the preparation of chemically-related compounds. Such processes, when used to prepare a compound of the formula (I), or a pharmaceutically-acceptable salt or an in vivo hydrolysable ester thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples (in which, for example, 3,5-difluorophenyl, 3-fluorophenyl and (des-fluoro)phenyl containing intermediates may all be prepared by analogous procedures; or by alternative procedures—for example, the preparation of (T group)-(fluoro)phenyl intermediates by reaction of a (fluoro)phenylstannane with, for example, a pyran or (tetrahydro)pyridine compound, may also be prepared by anion chemistry (see, for example, WO97/30995). Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the following Patent and Application Publications, the contents of the relevant process sections of which are hereby incorporated herein by reference: WO99/02525; WO98/54161; WO97/37980; WO97/30981 (& U.S. Pat. No. 5,736,545); WO97/21708 (& U.S. Pat. No. 5,719,154); WO97/10223; WO97/09328; WO96/35691; WO96/23788; WO96/15130; WO96/13502; WO95/25106 (& U.S. Pat. No. 5,668,286); WO95/14684 (& U.S. Pat. No. 5,652,238); WO95/07271 (& U.S. Pat. No. 5,688,792); WO94/13649; WO94/01110; WO93/23384 (& U.S. Pat. No. 5,547,950 & U.S. Pat. No. 5,700,799); WO93/09103 (& U.S. Pat. No. 5,565,571, U.S. Pat. No. 5,654,428, U.S. Pat. No. 5,654,435, U.S. Pat. No. 5,756,732 & U.S. Pat. No. 5,801,246); U.S. Pat. No. 5,231,188; U.S. Pat. No. 5,247,090; U.S. Pat. No. 5,523,403; WO97/27188; WO97/30995; WO97/31917; WO98/01447; WO98/01446; WO99/10342; WO99/10343; WO99/11642; WO99/64416; WO99/64417 and GB99/03299; European Patent Application Nos. 0,359,418 and 0,609,905; 0,693,491 A1 (& U.S. Pat. No. 5,698,574); 0,694,543 A1 (& AU 24985/95); 0,694,544 A1 (& CA 2,154,024); 0,697,412 A1 (& U.S. Pat. No. 5,529,998); 0,738,726 A1 (& AU 50735/96); 0,785,201 A1 (& AU 10123/97); German Patent Application Nos. DE 195 14 313 A1 (& U.S. Pat. No. 5,529,998); DE 196 01 264 A1 (& AU 10098/97); DE 196 01 265 A1 (& AU 10097/97); DE 196 04 223 A1 (& AU 12516/97); DE 196 49 095 A1 (& AU 12517/97).

The following Patent and Application Publications may also provide useful information and the contents of the relevant process sections are hereby incorporated herein by reference:

FR 2458547; FR 2500450(& GB 2094299, GB 2141716 & U.S. Pat. No. 4,476,136); DE 2923295 (& GB 2028306, GB 2054575, U.S. Pat. No. 4,287,351, U.S. Pat. No. 4,348,393, U.S. Pat. No. 4,413,001, U.S. Pat. No. 4,435,415 & U.S. Pat. No. 4,526,786); DE 3017499 (& GB 2053196, U.S. Pat. No. 4,346,102 & U.S. Pat. No. 4,372,967); U.S. Pat. No. 4,705,799; European Patent Application Nos. 0,312,000; 0,127,902; 0,184,170; 0,352,781; 0,316,594;

The skilled organic chemist will be able to use and adapt the information contained and referenced within the above references, and accompanying Examples therein and also the Examples herein, to obtain necessary starting materials, and products.

Thus, the present invention also provides that the compounds of the formulae (I) and pharmaceutically-acceptable salts and in vivo hydrolysable esters thereof, can be prepared by a process (a) to (d) as follows (wherein the variables are as defined above unless otherwise stated):

(wherein the variables are as defined above unless otherwise stated)

(a) by modifying a substituent in or introducing a substituent into another compound of formula (I);

(b) by reaction of a compound of formula (II):

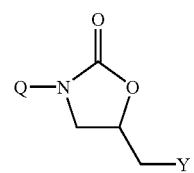

(II)

wherein Y is a displaceable group (which may be pre-formed, such as chloro or mesylate, or generated in-situ, for example under Mitsunobu conditions) with a compound of the formula (III):

HET    (III)

wherein HET is HET-H free-base form or HET- anion formed from the free base form; or (c) by reaction of a compound of the formula (IV):

wherein Z is an isocyanate, amine or urethane group with an epoxide of the formula (V)

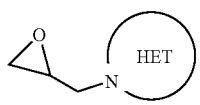

(d) For the 1,2,3-triazoles there is the additional possibility by cycloaddition via the azide (wherein Y in (II) is azide); and thereafter if necessary: (i) removing any protecting groups; (ii) forming a pharmaceutically-acceptable salt; (iii) forming an in-vivo hydrolysable ester.

The main synthetic routes are illustrated in the Scheme below (with Q as phenyl, and X, R and A defined with reference to analogous substituents defined elsewhere herein). The compounds of the invention may be prepared by analogous chemistry adapted from this Scheme. The Scheme also shows the preparation of 1,2,3-triazoles via the azide (prepared from the relevant hydroxy compound).

Deprotection, salt formation or in-vivo hydrolysable ester formation may each be provided as a specific final process step.

The N-linked hetereocycle can of course be prepared early in the overall synthesis, and then other functional groups changed.

Where Y is a displaceable group, suitable values for Y are for example, a halogeno or sulfonyloxy group, for example a chloro, bromo, methanesulfonyloxy or toluene-4-sulfonyloxy group.

General guidance on reaction conditions and reagents may be obtained in Advanced Organic Chemistry, 4$^{th}$ Edition, Jerry March (publisher: J. Wiley & Sons), 1992. Necessary starting materials may be obtained by standard procedures of organic chemistry, such as described in this process section, in the Examples section or by analogous procedures within the ordinary skill of an organic chemist. Certain references are also provided which describe the preparation of certain suitable starting materials, for example International Patent Application Publication No. WO 97/37980, the contents of which are incorporated here by reference. Processes analogous to those described in the references may also be used by the ordinary organic chemist to obtain necessary starting materials.

(a) Methods for converting substituents into other substituents are known in the art. For example an alkylthio

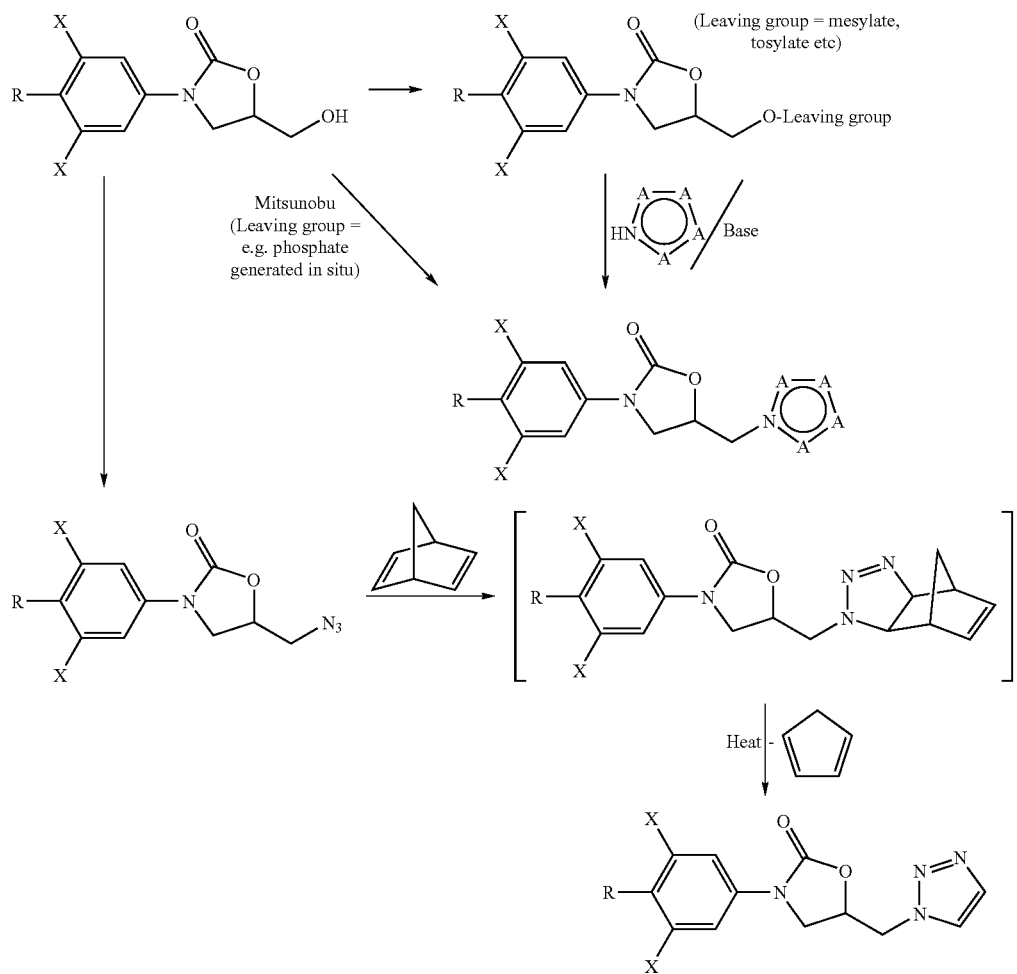

group may be oxidised to an alkylsulfinyl or alkysulfonyl group, a cyano group reduced to an amino group, a nitro group reduced to an amino group, a hydroxy group alkylated to a methoxy group, a hydroxy group thiomethylated to an arylthiomethyl or a heteroarylthiomethyl group (see, for example, Tet. Lett., 585, 1972), a carbonyl group converted to a thiocarbonyl group (eg. using Lawsson's reagent) or a bromo group converted to an alkylthio group. It is also possible to convert one Rc group into another Rc group as a final step in the preparation of a compound of the formula (I), for example, acylation of a group of formula (TC5) wherein Rc is hydrogen.

(b)(i) Reaction (b)(i) (in which Y is initially hydroxy) is performed under Mitsunobu conditions, for example, in the presence of tri-n-butylphosphine and diethyl azodicarboxylate (DEAD) in an organic solvent such as THF, and in the temperature range 0° C.–60° C., but preferably at ambient temperature. Details of Mitsunobu reactions are contained in Tet. Letts., 31, 699, (1990); The Mitsunobu Reaction, D. L. Hughes, Organic Reactions, 1992, Vol. 42, 335–656 and Progress in the Mitsunobu Reaction, D. L. Hughes, Organic Preparations and Procedures International, 1996, Vol. 28, 127–164.

Compounds of the formula (II) wherein Y is hydroxy may be obtained as described in the references cited herein (particularly in the section proceeding the discussion of protecting groups), for example, by reacting a compound of the formula (VI) with a compound of formula (VII):

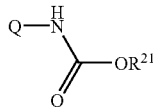

(VI)

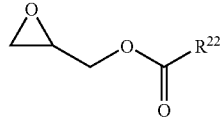

(VII)

wherein $R^{21}$ is (1–6C)alkyl or benzyl and $R^{22}$ is (1–4C)alkyl or —S(O)$_n$(1–4C)alkyl where n is 0, 1 or 2. Preferably $R^{22}$ is (1–4C)alkyl.

In particular, compounds of the formula (II), (VI) and (VII) may be prepared by the skilled man, for example as described in International Patent Application Publication Nos. WO95/07271, WO97/27188, WO 97/30995, WO 98/01446 and WO 98/01446, the contents of which are hereby incorporated by reference, and by analogous processes.

If not commercially available, compounds of the formula (III) may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl, Methoden der Organische Chemie, E8a, Pt.I (1993), 45–225, B. J. Wakefield.

(b)(ii) Reactions (b)(ii) are performed conveniently in the presence of a suitable base such as, for example, an alkali or alkaline earth metal carbonate, alkoxide or hydroxide, for example sodium carbonate or potassium carbonate, or, for example, an organic amine base such as, for example, pyridine, 2,6-lutidine, collidine, 4-dimethylaminopyridine, triethylamine, morpholine or diazabicyclo-[5.4.0]undec-7-ene, the reaction is also preferably carried out in a suitable inert solvent or diluent, for example methylene chloride, acetonitrile, tetrahydrofuran, 1,2-dimethoxyethane, N,N-dimethylformamide, N,N-dimethylacetamide, N-methylpyrrolidin-2-one or dimethylsulfoxide at and at a temperature in the range 25–60° C.

When Y is chloro, the compound of the formula (II) may be formed by reacting a compound of the formula (II) wherein Y is hydroxy (hydroxy compound) with a chlorinating agent. For example, by reacting the hydroxy compound with thionyl chloride, in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature. A compound of the formula (II) wherein Y is chloro or iodo may also be prepared from a compound of the formula (II) wherein Y is mesylate or tosylate, by reacting the latter compound with lithium chloride or lithium iodide and crown ether, in a suitable organic solvent such as THF, in a temperature range of ambient temperature to reflux When Y is (1–4C)alkanesulfonyloxy or tosylate the compound (II) may be prepared by reacting the hydroxy compound with (1–4C)alkanesulfonyl chloride or tosyl chloride in the presence of a mild base such as triethylamine or pyridine.

When Y is a phosphoryl ester (such as PhO$_2$—P(O)—O—) or Ph$_2$-P(O)—O— the compound (II) may be prepared from the hydroxy compound under standard conditions.

(c) Reaction (c) is performed under conditions analogous to those described in the following references which disclose how suitable and analogous starting materials may be obtained.

Reaction (c) is especially suitable for compounds in which HET is an electron deficient heteroaryl (such as, for example, thiadiazole or triazine).

Compounds of the formula Q—Z wherein Z is an isocyanate may be prepared by the skilled chemist, for example by analogous processes to those described in Walter A. Gregory et al in J. Med. Chem. 1990, 33, 2569–2578 and Chung-Ho Park et al in J. Med. Chem. 1992, 35, 1156–1165. Compounds of the formula Q-Z wherein Z is a urethane may be prepared by the skilled chemist, for example by analogous processes to those described in International Patent Application Publication Nos. WO 97/30995 and WO 97/37980.

A similar reaction to reaction (c) may be performed in which Q-Z wherein Z is a amine group is reacted with the epoxide (optionally in the presence of an organic base), and the product is reacted with, for example, phosgene to form the oxazolidinone ring. Such reactions and the preparation of starting materials in within the skill of the ordinary chemist with reference to the above-cited documents disclosing analogous reactions and preparations.

Epoxides of the formula (V) may be prepared from the corresponding compound of formula (VIII):

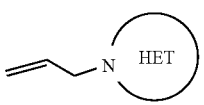

(VIII)

Certain such epoxide and alkene intermediates are novel and are provided as a further feature of the invention. Asymmetric epoxidation may be used to give the desired optical isomer.

(d) The cycloaddition reaction to form 1,2,3 triazoles from the corresponding azide is performed under conventional conditions.

Compounds of the formula (II) wherein Y is azide may be obtained as described in the references cited herein (particularly in the section proceeding the discussion of protecting groups), for example from the corresponding compounds in which Y is hydroxy or mesylate.

The removal of any protecting groups, the formation of a pharmaceutically-acceptable salt and/or the formation of an in vivo hydrolysable ester are within the skill of an ordinary organic chemist using standard techniques. Furthermore, details on the these steps, for example the preparation of in-vivo hydrolysable ester prodrugs has been provided in the section above on such esters, and in certain of the following non-limiting Examples.

When an optically active form of a compound of the formula (I) is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the formula (I) is required, it may be obtained by carrying out one of the above procedures using a pure regioisomer as a starting material, or by resolution of a mixture of the regioisomers or intermediates using a standard procedure.

According to a further feature of the invention there is provided a compound of the formula (I), or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The invention also provides a compound of the formula (I), or a pharmaceutically-acceptable salt, or in-vivo hydrolysable ester thereof, for use as a medicament; and the use of a compound of the formula (I) of the present invention, or a pharmaceutically-acceptable salt, or in-vivo hydrolysable ester thereof, in the manufacture of a medicament for use in the production of an antibacterial effect in a warm blooded animal, such as man.

In order to use a compound of the formula (I), an in-vivo hydrolysable ester or a pharmaceutically-acceptable salt thereof, including a pharmaceutically-acceptable salt of an in-vivo hydrolysable ester, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I), an in-vivo hydrolysable ester or a pharmaceutically-acceptable salt thereof, including a pharmaceutically-acceptable salt of an in-vivo hydrolysable ester, and a pharmaceutically-acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, aerosols (or sprays), drops and sterile injectable aqueous or oily solutions or suspensions.

In addition to the compounds of the present invention the pharmaceutical composition of this invention may also contain or be co-administered (simultaneously, sequentially or separately) with one or more known drugs selected from other clinically useful antibacterial agents (for example, β-lactams or aminoglycosides) and/or other anti-infective agents (for example, an antifungal triazole or amphotericin). These may include carbapenems, for example meropenem or imipenem, to broaden the therapeutic effectiveness. Compounds of this invention may also contain or be co-administered with bactericidal/permeability-increasing protein (BPI) products or efflux pump inhibitors to improve activity against gram negative bacteria and bacteria resistant to antimicrobial agents.

A suitable pharmaceutical composition of this invention is one suitable for oral administration in unit dosage form, for example a tablet or capsule which contains between 1 mg and 1 g of a compound of this invention, preferably between 100 mg and 1 g of a compound. Especially preferred is a tablet or capsule which contains between 50 mg and 800 mg of a compound of this invention, particularly in the range 100 mg to 500 mg.

In another aspect a pharmaceutical composition of the invention is one suitable for intravenous, subcutaneous or intramuscular injection, for example an injection which contains between 0.1% w/v and 50% w/v (between 1 mg/ml and 500 mg/ml) of a compound of this invention.

Each patient may receive, for example, a daily intravenous, subcutaneous or intramuscular dose of 0.5 mgkg-1 to 20 mgkg-1 of a compound of this invention, the composition being administered 1 to 4 times per day. In another embodiment a daily dose of 5 mgkg-1 to 20 mgkg-1 of a compound of this invention is administered. The intravenous, subcutaneous and intramuscular dose may be given by means of a bolus injection. Alternatively the intravenous dose may be given by continuous infusion over a period of time. Alternatively each patient may receive a daily oral dose which may be approximately equivalent to the daily parenteral dose, the composition being administered 1 to 4 times per day.

A pharmaceutical composition to be dosed intravenously may contain advantageously (for example to enhance stability) a suitable bactericide, antioxidant or reducing agent, or a suitable sequestering agent.

In the above other, pharmaceutical composition, process, method, use and medicament manufacture features, the alternative and preferred embodiments of the compounds of the invention described herein also apply.

Antibacterial Activity:

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of S.aureus and coagulase negative staphylococci, together with *haemophilus* and *moraxella* strains. The antibacterial spectrum and potency of a particular compound may be determined in a standard test system.

The (antibacterial) properties of the compounds of the invention may also be demonstrated and assessed in-vivo in conventional tests, for example by oral and/or intravenous dosing of a compound to a warm-blooded mammal using standard techniques.

The following results were obtained on a standard in-vitro test system. The activity is described in terms of the minimum inhibitory concentration (MIC) determined by the agar-dilution technique with an inoculum size of $10^4$ CFU/spot. Typically, compounds are active in the range 0.01 to 256 µg/ml.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours—blood is required for the growth of some of the test organisms. Fastidious Gram negative organisms were tested in Mueller-Hinton broth, supplemented with hemin and NAD, grown aerobically for 24 hours at 37° C., and with an innoculum of $5 \times 10^4$ CFU/well.

For example, the following results were obtained for the compound of Example 44a:

| Organism | MIC (µg/ml) |
|---|---|
| *Staphylococcus aureus*: | |
| Oxford | 0.125 |
| Novb. Res | 0.25 |
| MRQR | 0.25 |
| Coagulase Negative Staphylococci | |
| MS | 0.06 |
| MR | 0.13 |
| *Streptococcus pyogenes* C203 | 0.25 |
| *Enterococcus faecalis* | 0.25 |
| *Bacillus subtilis* | 0.25 |
| *Haemophilus influenzae* ARC446 | 2 |
| *Moraxella catarrhalis* ARC445 | 2 |

Novb. Res = Novobiocin resistant
MRQR = methicillin and quinolone resistant
MR = methicillin resistant
MS = methicillin sensitive Certain intermediates and/or Reference Examples described hereinafter within the scope of the invention may also possess useful activity, and are provided as a further feature of the invention.

The invention is now illustrated but not limited by the following Examples in which unless otherwise stated:—

(i) evaporations were carried out by rotary evaporation in vacuo and work-up procedures were carried out after removal of residual solids by filtration;

(ii) operations were carried out at ambient temperature, that is typically in the range 18–26° C. and in air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable;

(v) the structure of the end-products of the formula (I) were generally confirmed by NMR and mass spectral techniques [proton magnetic resonance spectra were generally determined in DMSO-$d_6$ unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ scale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected];

(vi) intermediates were not generally fully characterised and purity was in general assessed by thin layer chromatographic, infra-red (IR), mass spectral (MS) or NMR analysis; and (vii) in which the following abbreviations may be used:—
® is a Trademark; DMF is N,N-dimethylformamide; DMA is N,N-dimethylacetamide; TLC is thin layer chromatography; HPLC is high pressure liquid chromatography; MPLC is medium pressure liquid chromatography; DMSO is dimethylsulfoxide; CDCl$_3$ is deuterated chloroform; MS is mass spectroscopy; ESP is electrospray; EI is electron impact; CI is chemical ionisation; THF is tetrahydrofuran; TFA is trifluoroacetic acid; NMP is N-methylpyrrolidone; HOBT is 1-hydroxy-benzotriazole; EtOAc is ethyl acetate; MeOH is methanol; phosphoryl is (HO)$_2$—P(O)—O—; phosphiryl is (HO)$_2$—P—O—; EDC is 1-(3-dimethylaminopropyl)-3-ethylcarbodiimide (hydrochloride); PTSA is para-toluenesulfonic acid.

(viii) Temperatures are quoted as ° C.

EXAMPLE 1

(5R)-3-(4-(1,4-Dioxa-8-azaspiro[4,5]dec-8-yl)-3-fluorophenyl)-5-(1,2,3-triazol-1-ylmethyl)oxazolidin-2-one (5R)-3-(4-(1,4-Dioxa-8-azaspiro[4,5]decan-8-yl)-3-fluorophenyl)-5-azidomethyloxazolidin-2-one (2.44 g, 6.5 mM) was dissolved in dioxane (50 ml), treated with norbornadiene (2.98 g, 32.3 mM) and heated under reflux for 20 hours. After removal of the solvent, the residue was dissolved in dichloromethane (350 ml) washed with water (3×200 ml), and dried over magnesium sulfate. After filtration and evaporation the residue was purified by chromatography on a 20 g silica Mega Bond Elut® column, eluting with a gradient increasing in polarity from 0 to 2.5% methanol in dichloromethane. Relevant fractions were combined and evaporated to give the desired product (1.5 g).

MS (ESP): 404 (MH$^+$) for $C_{19}H_{22}FN_5O_4$

NMR (CDCl$_3$) δ: 1.79 (t, 4H); 3.04 (t, 4H); 3.80 (dd, 1H); 3.92 (s, 4H); 4.04 (t, 1H); 4.70 (m, 2H); 4.96 (m, 1H); 6.85 (overlapping m, 2H); 7.20 (t, 1H); 7.66 (d, 1H); 7.71 (d, 1H).

The intermediates for this compound were prepared as follows (see also WO 95-25106—Ex 3).

4-(1,4-Dioxa-8-azaspiro[4,5]dec-8-yl)-3-fluoronitrobenzene 3,4-Difluoronitrobenzene (15.53 g, 0.098 M) was dissolved in acetonitrile (150 ml), and treated with N,N-diisopropylethylamine (31.5 g, 0.244 M) and 1,4-dioxa-8-aza-spiro[4,5]decane (15.36 g, 0.107 M). The mixture was stirred and heated to reflux for 18 hours. After cooling, product precipitated as a yellow solid, and was filtered off (16.1 g); further product could be obtained by concentrating the residues (8.43 g).

MS (ESP): 283 (MH$^+$) for $C_{13}H_{15}FN_2O_4$

NMR (CDCl$_3$) δ: 1.86 (t, 4H); 3.41 (t, 4H); 4.00 (s, 4H); 6.91 (t, 1H); 7.89 (dd, 1H); 7.96 (dd, 1H).

5-Amino-2-(1,4-dioxa-8-azaspiro[4,5]dec-8-yl)fluorobenzene 4-(1,4-Dioxa-8-azaspiro[4,5]dec-8-yl)-3-fluoronitrobenzene (24.48 g, 0.087 M) was dissolved in ethyl acetate (500 ml) treated with palladium catalyst (10% on carbon, 5 g) and hydrogenated at atmospheric pressure until the theoretical uptake of gas. After filtration through celite and evaporation, the required product was obtained as a pink solid of sufficient quality for use without purification (19.3 g).

MS (ESP): 253 (MH$^+$) for $C_{13}H_{17}FN_2O_2$

NMR (DMSO-d$_6$) δ: 1.69 (t, 4H); 2.84 (t, 4H); 3.86 (s, 4H); 4.91 (s, 2H); 6.28 (m, 2H); 6.75 (t, 1H).

5-Ethoxycarbonylamino-2-(1,4-dioxa-8-azaspiro[4,5]dec-8-yl)fluorobenzene

5-Amino-2-(1,4-dioxa-8-azaspiro[4,5]dec-8-yl)fluorobenzene (19.26 g, 0.076 M), was dissolved in dry pyridine (75 ml) and cooled under nitrogen with stirring to 0°. Ethyl chloroformate (9.08, 0.084 M) was added dropwise, and the mixture stirred 30 minutes at the same temperature. Ice-water (300 ml) was added, and stirring continued for 1 hour. The resulting precipitate was collected, washed thoroughly with water, and dried, to give the desired product of sufficient quality for use without purification (20.5 g).

MS (ESP): 325 (MH$^+$) for $C_{16}H_{21}FN_2O_4$

NMR (DMSO-d$_6$) δ:1.21 (t, 3H); 1.71 (t, 4H); 2.96 (t, 4H); 3.88 (s, 4H); 4.09 (q, 2H); 6.95 (t, 1H); 7.09 (dd, 1H); 7.27 (dd, 1H); 9.54 (s, 1H).

(5R)-3-(4-(1,4-Dioxa-8-azaspiro[4,5]dec-8-yl)-3-fluorophenyl)-5-hydroxymethyloxazolidin-2-one 5-Ethoxycarbonylamino-2-(1,4-dioxa-8-azaspiro[4,5]dec-8-yl)fluorobenzene (22.9 g, 0.071 M) was dissolved in dry tetrahydrofuran (250 ml) under nitrogen, cooled to −70°, and treated dropwise over 30 minutes with a solution of lithium t-butoxide (1M in tetrahydrofuran, 77.6 ml), keeping the temperature below −70°. After stirring for 5 minutes, (R)-glycidylbutyrate (11.19 g, 0.077 M) was added, and stirring continued at −65° for 1 hour, before allowing the temperature to rise to ambient over 16 hours. The precipitate was collected and washed with tetrahydrofuran to give the desired product (17.8 g).

MS (ESP): 353 (MH$^+$) for $C_{17}H_{21}FN_2O_5$

NMR (DMSO-d$_6$) δ: 1.83 (t, 4H); 3.09 (t, 4H); 3.69 (dd, 1H); 3.82 (dd, 1H); 3.88 (dd, 1H); 3.96 (s, 4H); 4.07 (t, 1H); 4.72 (m, 1H); 4.92 (s, 1H); 7.05 (t, 1H); 7.15 (dd, 1H); 7.46 (dd, 1H).

(5R)-3-(4-(1,4-Dioxa-8-azaspiro[4,5]dec-8-yl)-3-fluorophenyl)-5-methanesulfonyloxymethyl-oxazolidin-2-one (5R)-3-(4-(1,4-Dioxa-8-azaspiro[4,5]dec-8-yl)-3-fluorophenyl)-5-hydroxymethyloxazolidin-2-one (4.024 g, 11.43 mM) was dissolved in dichloromethane (200 ml), and treated with triethylamine (1.45 g, 14.4 mM), then cooled under nitrogen to 0°. Methanesulfonyl chloride (1.32 g, 11.5 mM) was added dropwise, and the mixture stirred 18 hours allowing the temperature to rise to ambient. The mixture was washed with water (3×75 ml), concentrated, and purified by chromatography on a 90 g silica Biotage column, eluting with 1% methanol in dichloromethane. Relevant fractions were combined and evaporated to give the desired product (3.09 g).

MS (ESP): 431 (MH$^+$) for $C_{18}H_{23}FN_2O_7S$

NMR (DMSO-d$_6$) δ: 1.82 (t, 4H); 3.03 (s, 3H); 3.08 (t, 4H); 3.84 (dd, 1H); 3.92 (s, 4H); 4.04 (t, 1H); 4.33 (dd, 1H); 4.43 (dd, 1H); 4.84 (m, 1H); 6.91 (t, 1H); 7.02 (dd, 1H); 7.34 (dd, 1H).

(5R)-3-(4-(1,4-Dioxa-8-azaspiro[4,5]dec-8-yl)-3-fluorophenyl)-5-azidomethyloxazolidin-2-one (5R)-3-(4-(1,4-Dioxa-8-azaspiro[4,5]dec-8-yl)-3-fluorophenyl)-5-methanesulfonyloxymethyl-oxazolidin-2-one (3.03 g, 7.04 mM) was dissolved in N,N-dimethylformamide (50 ml), treated with sodium azide (732 mg, 11.3 mM), and heated with stirring at 50° for 4 hours. After cooling the mixture was diluted with water (250 ml), and extracted into ethyl acetate (3×100 ml). The combined organics were dried (magnesium sulfate), and evaporated to give product (2.44 g), of sufficient quality for use without purification.

MS (ESP): 378 (MH$^+$) for $C_{17}H_{20}FN_5O_4$

NMR (CDCl$_3$) δ: 1.73 (t, 4H); 3.02 (t, 4H); 3.66 (dd, 1H); 3.74 (m, 2H); 3.91 (s, 4H); 4.11 (t, 1H); 4.86 (m, 1H); 7.09 (t, 1H); 7.17 (dd, 1H); 7.48 (dd, 1H).

EXAMPLE 2

(5R)-3-(4-(4-Oxopiperidin-1-yl)-3-fluorophenyl)-5-(1,2,3-triazol-1-ylmethyl)oxazolidin-2-one (5R)-3-(4-(1,4-Dioxa-8-azaspiro[4,5]dec-8-yl)-3-fluorophenyl)-5-(1,2,3-triazol-1-ylmethyl)oxazolidin-2-one (1.47 g, 3.65 mM) was dissolved in a mixture of glacial acetic acid (30 ml) and water (30 ml), and heated at 50° for 18 hours. Solvent was evaporated, the residue azeotroped with toluene (50 ml), then partitioned between ethyl acetate (150 ml) and water (100 ml). The organic layer was washed with saturated aqueous sodium bicarbonate solution (2×100 ml), water (100 ml), dried (magnesium sulfate) and evaporated to give product (894 mg), of sufficient quality for use without purification.

MS (ESP): 360 (MH$^+$) for $C_{17}H_{18}FN_5O_3$

NMR (CDCl$_3$) δ: 2.53 (t, 4H); 3.29 (t, 4H); 3.84 (dd, 1H); 4.06 (t, 1H); 4.71 (d, 2H); 4.97 (m, 1H); 6.90 (overlapping m, 2H); 7.24 (dd, 1H); 7.67 (d, 1H); 7.72 (d, 1H).

EXAMPLE 3

(5R)-3-(4-(4-Aminopiperidin-1-yl)-3-fluorophenyl)-5-(1,2,3-triazol-1-ylmethyl)oxazolidin-2-one (5R)-3-(4-(4-Oxopiperidin-1-yl)-3-fluorophenyl)-5-(1,2,3-triazol-1-yl) methyl)oxazolidin-2-one (838 mg, 2.33 mM) was dissolved in methanol (25 ml), treated with ammonium acetate (1.8 g, 23.3 mM) and sodium cyanoborohydride (1.03 g, 16.3 mM) and refluxed 16 hours. The mixture was neutralised with 1 N hydrochloric acid, water (125 ml) added, extracted with dichloromethane (5×75 ml), and dried (magnesium sulfate). Evaporation gave the desired product (686 mg).

MS (ESP): 361 (MH$^+$) for $C_{17}H_{21}FN_6O_2$

NMR (DMSO-$d_6$) δ: 1.43 (m, 2H); 1.86 (dd, 2H); 2.71 (tm, 4H); 3.29 (m, 1H); 3.90 (dd, 1H); 4.25 (t, 1H); 4.87 (d, 2H); 5.15 (m, 1H); 7.08 (t, 1H); 7.12 (dd, 1H); 7.42 (dd, 1H); 7.81 (d, 1H); 8.21 (d, 1H); NH$_2$ exchanged, not seen.

EXAMPLE 4

(5R)-3-(4-(4-Methanesulfonamidopiperidin-1-yl)-3-fluorophenyl)-5-(1,2,3-triazol-1-ylmethyl)oxazolidin-2-one (5R)-3-(4-(4-Aminopiperidin-1-yl)-3-fluorophenyl)-5-(1,2,3-triazol-1-yl) methyl)oxazolidin-2-one (175 mg, 0.49 mM) in dichloromethane (10 ml) was treated with triethylamine (78 mg, 0.78 mM) and methanesulfonyl chloride (67 mg, 0.58 mM) and the mixture stirred for 18 hours at ambient temperature under nitrogen. The mixture was filtered, and solution purified directly by chromatography on a 10 g silica Mega Bond Elut® column, eluting with a gradient increasing in polarity from 0 to 2.5% methanol in dichloromethane. Relevant fractions were combined and evaporated to give the desired product (19 mg).

MS (ESP): 439 (MH$^+$) for $C_{18}H_{23}FN_6O_4S$

NMR (DMSO-$d_6$) δ: 1.66 (m, 2H); 1.98 (dd, 2H); 2.76 (tm, 4H); 3.00 (s, 3H); 3.89 (dd, 1H); 4.12 (dd, 1H); 4.25 (t, 1H); 4.87 (d, 2H); 5.17 (m, 1H); 7.08 (t, 1H); 7.14 (d, 1H); 7.19 (dd, 1H); 7.42 (dd, 1H); 7.81 (d, 1H); 8.21 (d, 1H).

EXAMPLE 5

(5R)-3-(4-(4-Methoxycarbonylaminopiperidin-1-yl)-3-fluorophenyl)-5-(1,2,3-triazol-1-ylmethyl)oxazolidin-2-one (5R)-3-(4-(4-Aminopiperidin-1-yl)-3-fluorophenyl)-5-(1,2,3-triazol-1-yl) methyl)oxazolidin-2-one (151 mg, 0.42 mM) in dichloromethane (20 ml) was cooled to 0° and treated with 5% sodium bicarbonate solution (4 ml). The resulting suspension was stirred vigorously, methyl chloroformate (245 mg, 2.6 mM) added, and stirring continued for 3 hours at ambient temperature. The dichloromethane was removed by evaporation, ethyl acetate (15 ml) added, and the organic layer was separated, washed with 2% sodium dihydrogen phosphate (2×15 ml), brine (15 ml), and dried (magnesium sulfate), to give the desired product (170 mg).

MS (ESP): 419 (MH$^+$) for $C_{19}H_{23}FN_6O_4$

NMR (DMSO-$d_6$) δ:1.53 (qm, 2H); 1.82 (dd, 2H); 2.68 (t, 2H); 3.24 (m, 2H); 3.39 (m, 1H); 3.52 (s, 3H); 3.83 (dd, 1H); 4.18 (t, 1H); 4.83 (d, 2H); 5.09 (m, 1H); 7.02 (t, 1H); 7.06 (dd, 1H); 7.15 (d, 1H); 7.36 (dd, 1H); 7.74 (d, 1H); 8.14 (d, 1H).

EXAMPLE 6

(5R)-3-(4-(4-Methylaminopiperidin-1-yl)-3-fluorophenyl)-5-(1,2,3-triazol-1-ylmethyl)oxazolidin-2-one (5R)-3-(4-(4-Oxopiperidin-1-yl)-3-fluorophenyl)-5-(1,2,3-triazol-1-ylmethyl)oxazolidin-2-one (250 mg, 0.70 mM) was dissolved in a mixture of anhydrous tetrahydrofuran (5 ml) and dichloromethane (5 ml) under nitrogen. Acetic acid (1 drop), methylamine (33% solution in methanol, 31 μL, 0.77 mM) and sodium acetoxyborohydride (222 mg, 1.05 mM) were added, and the mixture stirred at ambient temperature for 3 hours. The mixture was diluted with water (15 ml) and dichloromethane (15 ml), and the pH adjusted to 9 by addition of triethylamine. The organic phase was separated, washed with water (2×15 ml), brine (15 ml), and dried (magnesium sulfate). Evaporation gave the desired product (145 mg).

MS (ESP): 375 (MH$^+$) for $C_{18}H_{23}FN_6O_2$

NMR (DMSO-$d_6$) δ: 1.45 (m, 2H); 1.95 (dd, 2H); 2.36 (s, 3H); 2.48 (dd, 2H); 2.71 (t, 2H); 3.91 (dd, 1H); 4.25 (t, 1H); 4.87 (d, 2H); 5.16 (m, 1H); 7.10 (overlapping m, 2H); 7.45 (dd, 1H); 7.81 (d, 1H); 8.22 (d, 1H); NH exchanged, CH—N under H$_2$O, neither seen.

EXAMPLE 7

(5R)-3-(4-(4-N-Methyl-methanesulfonamidopiperidin-1-yl)-3-fluorophenyl)-5-(1,2,3-triazol-1-ylmethyl)oxazolidin-2-one (5R)-3-(4-(4-Methylaminopiperidin-1-yl)-3-fluorophenyl)-5-(1,2,3-triazol-1-yl) methyl)-oxazolidin-2-one (200 mg, 0.53 mM, Example 6), was treated essentially as Example 4 to give the title product after chromatography (53 mg).

MS (ESP): 453 (MH$^+$) for $C_{19}H_{25}FN_6O_4S$

NMR (DMSO-$d_6$) δ: 1.79 (d, 2H); 2.00 (ddd, 2H); 2.74 (t, 2H); 2.84 (s, 3H); 2.87 (s, 3H); 3.44 (d, 2H); 3.87 (m, 1H); 3.89 (dd, 1H); 4.12 (t, 1H); 4.77 (d, 2H); 5.04 (m, 1H); 6.89 (t, 1H); 6.95 (dd, 1H); 7.28 (dd, 1H); 7.74 (d, 1H); 7.79 (d, 1H).

EXAMPLE 8

(5R)-3-(4-(4-N-Methyl-methoxycarbonylaminopiperidin-1-yl)-3-fluorophenyl)-5-(1,2,3-triazol-1-ylmethyl)oxazolidin-2-one (5R)-3-(4-(4-Methylaminopiperidin-1-yl)-3-fluorophenyl)-5-(1,2,3-triazol-1-yl) methyl)-oxazolidin-2-one (200 mg, 0.53 mM, Example 6), was treated essentially as Example 4, except for the substitution of methyl chloroformate for methanesulfonyl chloride, to give the title product after chromatography (131 mg).

MS (ESP): 433 (MH$^+$) for $C_{20}H_{25}FN_6O_4$

NMR (DMSO-$d_6$) δ: 1.62 (d, 2H); 1.82 (ddd, 2H); 2.69 (t, 2H); 2.74 (s, 3H); 3.32 (d, 2H); 3.59 (s, 3H); 3.83 (dd, 1H); 3.92 (m, 1H); 4.18 (t, 1H); 4.81 (d, 2H); 5.10 (m, 1H); 7.03 (t, 1H); 7.08 (dd, 1H); 7.37 (dd, 1H); 7.73 (d, 1H); 8.13 (d, 1H).

EXAMPLE 9

(5R)-3-(4-(4-N-Methyl-(2-acetoxyacetyl)aminopiperidin-1-yl)-3-fluoro-phenyl)-5-(1,2,3-triazol-1-ylmethyl)oxazolidin-2-one (5R)-3-(4-(4-Methylaminopiperidin-1-yl)-3-fluorophenyl)-5-(1,2,3-triazol-1-ylmethyl)-oxazolidin-2-one (350 mg, 0.94 mM, Example 6), was treated essentially as Example 4, except for the substitution of acetoxyacetyl chloride for methanesulfonyl chloride, to give the title product after chromatography (207 mg).

MS (ESP): 475 (MH$^+$) for $C_{22}H_{27}FN_6O_5$

NMR (DMSO-d$_6$) δ: 1.75 (d, 2H); 1.87 (dd, 2H); 2.07 (s, 3H); 2.70 (t, 2H); 2.74 (s, 3H); 3.36 (d, 2H); 3.62 (m, 1H); 3.83 (dd, 1H); 4.18 (t, 1H); 4.53 (s, 2H); 4.82 (d, 2H); 5.11 (m, 1H); 7.10 (overlapping m, 2H); 7.49 (dd, 1H); 7.76 (d, 1H); 8.16 (d, 1H).

EXAMPLE 10

(5R)-3-(4-(4-N-Methyl-(2-hydroxyacetyl)aminopiperidin-1-yl)-3-fluorophenyl)-5-(1,2,3-triazol-1-ylmethyl)oxazolidin-2-one (5R)-3-(4-(4-N-Methyl-(2-acetoxyacetyl)aminopiperidin-1-yl)-3-fluorophenyl)-5-(1,2,3-triazol-1-ylmethyl)oxazolidin-2-one (186 mg, 0.39 mM) was dissolved in methanol (20 ml), treated with potassium carbonate (0.3 g, 2.1 mM) and stirred at ambient temperature for 30 minutes. After removal of the solvent, the residue was purified by chromatography on a 5 g silica Mega Bond Elut® column, eluting with a gradient increasing in polarity from 0 to 5% methanol in dichloromethane. Relevant fractions were combined and evaporated to give the desired product (30 mg).

MS (ESP): 433 (MH$^+$) for $C_{20}H_{25}FN_6O_4$

NMR (DMSO-d$_6$) δ: 1.73 (d, 2H); 1.93 (ddd, 2H); 2.74 (t, 2H); 2.79 (s, 3H); 3.45 (d, 2H); 3.68 (s, 1H); 3.89 (dd, 1H); 4.11 (t, 1H); 4.16 (s, 2H); 4.58 (m, 1H); 4.79 (d, 2H); 5.04 (m, 1H); 6.91 (t, 1H); 6.95 (dd, 1H); 7.29 (dd, 1H); 7.73 (d, 1H); 7.79 (d, 1H).

EXAMPLE 11

(5R)-3-(4-(4-(2S)-2,3-Dihydroxypropionyl)piperazin-1-yl)-3-fluorophenyl)-5-(1,2,3-triazol-1-ylmethyl)oxazolidin-2-one (5R)-3-(4-(4-((4S)-2,2-Dimethyl-1,3-dioxolane-4-carbonyl)piperazin-1-yl)-3-fluorophenyl)-5-(1,2,3-triazol-1-ylmethyl)oxazolidin-2-one (278 mg, 0.59 mM) was dissolved in tetrahydrofuran (20 ml), treated with 1M aqueous hydrochloric acid (2 ml), and stirred at ambient temperature for 72 hours. After dilution with tetrahydrofuran (30 ml), solid potassium carbonate (2 g) was added, the mixture stirred 5 minutes, filtered, and evaporated to dryness. The residue was purified by chromatography on a 5 g silica Mega Bond Elut® column, eluting with a gradient increasing in polarity from 5 to 10% methanol in dichloromethane. Relevant fractions were combined, evaporated, and triturated with diethyl ether to give the desired product (89 mg).

MS (ESP): 435 (MH$^+$) for $C_{19}H_{23}FN_6O_5$

NMR(DMSO-d$_6$) δ: 2.91 (br m, 4H); 3.45 (m, 1H); 3.51 (m, 1H); 3.63 (br m, 4H); 3.82 (m, 1H); 4.18 (t, 1H); 4.34 (dd, 1H); 4.66 (t, 1H); 4.80 (d, 2H); 4.91 (t, 1H); 5.11 (m, 1H); 7.04 (t, 1H); 7.11 (dd, 1H); 7.39 (dd, 1H); 7.74 (d, 1H); 8.13 (d, 1H).

The intermediates for this compound were prepared as follows:

(5R)-3-(4-(4-t-Butoxycarbonylpiperazin-1-yl)-3-fluorophenyl)-5-(1,2,3-triazol-1-ylmethyl)oxazolidin-2-one (5R)-3-(4-(4-t-Butoxycarbonylpiperazin-1-yl)-3-fluorophenyl)-5-azidomethyl)oxazolidin-2-one (2.52 g, 6 mM) and norbornadiene (4.2 g, 45.6 mM) were dissolved in dioxane (50 ml) and heated under reflux for 6 hours. After evaporation of solvent, the residue was purified by recrystallisation from isopropanol (50 ml) to give the desired product (2.29 g).

MS (ESP): 447 (MH$^+$) for $C_{21}H_{27}FN_6O_4$

NMR (DMSO-d$_6$) δ: 1.40 (s, 9H); 2.81 (t, 4H); 3.45 (t, 4H); 3.83 (dd, 1H); 4.18 (t, 1H); 4.79 (d, 2H); 5.10 (m, 1H); 7.06 (t, 1H); 7.11 (dd, 1H); 7.38 (dd, 1H); 7.73 (d, 1H); 8.13 (d, 1H).

(Intermediate oxazolidinone described in Upjohn WO 93-23384)

(5R)-3-(4-(piperazin-1-yl)-3-fluorophenyl)-5-(1,2,3-triazol-1-ylmethyl)oxazolidin-2-one (5R)-3-(4-(4-t-Butoxycarbonylpiperazin-1-yl)-3-fluorophenyl)-5-(1,2,3-triazol-1-ylmethyl)oxazolidin-2-one (2.0 g, 4.48 mM), was suspended in ethanol (20 ml), and treated with a solution of hydrogen chloride in ethanol (3.8M, 15 ml). After stirring 18 hours at ambient temperature, the solution was evaporated to dryness, and the residue recrystallised from ethanol and diethyl ether, with charcoal treatment to give the product as its dihydrochloride salt (0.72 g).

MS (ESP): 347 (MH$^+$) for $C_{16}H_{19}FN_6O_2$

Microanalysis: Found, C 46.2; H 5.1; N 18.8%. $C_{16}H_{19}FN_6O_2.2HCl$ requires C, 45.8; H, 5.0; N 20.0%

(5R)-3-(4-(4-((4S)-2,2-Dimethyl-1,3-dioxolane-4-carbonyl)piperazin-1-yl)-3-fluorophenyl)-5-(1,2,3-triazol-1-ylmethyl)oxazolidin-2-one The lithium salt of (4S)-2,2-dimethyl-1,3-dioxolan-4-carboxylic acid (342 mg, 2.25 mM) in dichloromethane (10 ml) under nitrogen was cooled with stirring to 0°, treated with thionyl chloride (321 mg, 2.7 mM), then stirred at the same temperature for 3 hours. After filtration, the residue was evaporated to dryness, and redissolved in dichloromethane (10 ml), then added to a stirred suspension of (5R)-3-(4-piperazin-1-yl-3-fluorophenyl)-5-(1,2,3-triazol-1-ylmethyl) oxazolidin-2-one dihydrochloride (630 mg, 1.5 mM) in dichloromethane (30 ml) containing pyridine (370 mg, 4.9 mM) and triethylamine (500 mg, 4.9 mM). The mixture was stirred for 18 hours, allowing the temperature to rise to ambient. After dilution with dichloromethane (30 ml), the organic layer was separated, washed with water (3×30 ml), brine (50 ml), and dried (magnesium sulfate). The residue after evaporation was purified by chromatography on a 10 g silica Mega Bond Elut® column, eluting with a gradient increasing in polarity from 0 to 5% methanol in dichloromethane. Relevant fractions were combined and evaporated to give the desired product (278 mg).

MS (ESP): 475 (MH$^+$) for $C_{22}H_{27}FN_6O_5$

NMR (DMS-d$_6$) δ: 1.32 (s, 6H); 2.95 (br m, 4H); 3.63 (m, 4H); 3.86 (dd, 1H); 4.08 (t, 1H); 4.21 (m, 2H); 4.83 (d, 2H); 4.89 (t, 1H); 5.12 (m, 1H); 7.07 (t, 1H); 7.12 (dd, 1H); 7.42 (dd, 1H); 7.77 (d, 1H); 8.17 (d, 1H).

EXAMPLES 12–16

(5R)-3-(4-(4-(2-Chloroacetyl)piperazin-1-yl)-3-fluorophenyl)-5-(1,2,3-triazol-1-ylmethyl)oxazolidin-2-one (422 mg, 1 mM) and the appropriate amine (3 mM) were dissolved in a mixture of dichloromethane (10 ml) and ethanol (1 ml) and stirred at ambient temperature for 18 hours. Solvent was evaporated and the residue purified by chromatography on a 10 g silica Mega Bond Elut® column, eluting with an appropriate increasing gradient of methanol in dichloromethane. Relevant fractions were combined and evaporated to give the desired products.

MS (ESP): 462 (MH$^+$) for $C_{21}H_{28}FN_7O_4$

NMR (DMSO-d$_6$) δ: 2.87 (d, 3H); 2.99 (br m, 4H); 3.19 (br m, 1H); 3.28 (br m, 1H); 3.49 (br, 2H); 3.64 (br, 2H); 3.76 (t, 2H); 3.85 (dd, 1H); 4.18 (t, 1H); 4.34 (dd, 1H); 4.46 (dd, 1H); 4.81 (d, 2H); 5.11 (m, 1H); 7.04 (t, 1H); 7.13 (dd, 1H); 7.40 (dd, 1H); 7.74 (d, 1H); 8.16 (d, 1H); 9.58 (br, 1H); OH missing under solvent; +1H for HCl salt 3 Little reaction in ethanol at ambient temperature; solvent replaced by isopropanol (10 ml), and refluxed 18 hours before work up as above. Sample after chromatography dissolved in the minimum volume of ethanol, treated with a

| Example | Product | Amine | Yield (mg) | Notes |
|---|---|---|---|---|
| 12 | [structure with morpholine] | [morpholine] | 289 | 1 |
| 13 | [structure with MeN(CH2CH2OH)] | [HOCH2CH2NHMe] | 159 | 2 |
| 14 | [structure with acetamidoethylamino] | [MeC(O)NHCH2CH2NH2] | 120 | 3 |
| 15 | [structure with MeN(CH2CH2OMe)] | [MeOCH2CH2NHMe] | 245 | 4 |
| 16 | [structure with NHCH2CH2OMe] | [MeOCH2CH2NH2] | 143 | 5 |

Notes

1 MS (ESP): 474 (MH$^+$) for $C_{22}H_{28}FN_7O_4$

NMR (DMSO-d$_6$) δ: 2.40 (br, 4H); 2.90 (br, 2H); 2.96 (br, 2H); 3.19 (br, 2H); 3.56 (br, 6H); 3.65 (br, 2H); 3.84 (dd, 1H); 4.20 (t, 1H); 4.83 (d, 2H); 5.12 (m, 1H); 7.06 (t, 1H); 7.11 (dd, 1H); 7.41 (dd, 1H); 7.75 (d, 1H); 8.17 (d, 1H).

2 Sample after chromatography dissolved in the minimum volume of ethanol, treated with a solution of hydrogen chloride in ethanol (3.8M, 1 ml), then excess diethyl ether to precipitate the hydrochloride salt.

solution of hydrogen chloride in ethanol (3.8M, 1 ml), then excess diethyl ether to precipitate the hydrochloride salt.

MS (ESP): 489 (MH$^+$) for $C_{22}H_{29}FN_8O_4$

NMR (DMSO-d$_6$) δ: 1.83 (s, 3H); 2.97 (br, 6H); 3.33 (br m, 2H); 3.51 (br, 2H); 3.64 (br, 2H); 3.85 (dd, 1H); 4.10 (br t, 2H); 4.18 (t, 1H); 4.81 (d, 2H); 5.11 (m, 1H); 7.050 (t, 1H); 7.13 (dd, 1H); 7.41 (dd, 1H); 7.74 (d, 1H); 8.16 (d, 1H); 8.27 (br t, 1H); 9.07 (br, 2H); +1H for HCl salt.

4 Sample after chromatography dissolved in the minimum volume of ethanol, treated with a solution of hydrogen chloride in ethanol (3.8M, 1 ml), then excess diethyl ether to precipitate the hydrochloride salt.

MS (ESP): 476 (MH$^+$) for $C_{22}H_{30}FN_7O_4$

NMR (DMSO-d$_6$) δ: 2.87 (d, 3H); 2.99 (m, 4H); 3.28 (s, 3H); 3.33 (m, 1H); 3.42 (m overlapped by solvent, 1H); 3.52 (br, 2H); 3.69 (t overlapping br, 4H); 3.86 (dd, 1H); 4.20 (t, 1H); 4.33 (dd, 1H); 4.43 (dd, 1H); 4.84 (d, 2H); 5.13 (m, 1H); 7.05 (t, 1H); 7.13 (dd, 1H); 7.42 (dd, 1H); 7.75 (d, 1H); 8.18 (d, 1H); 9.78 (br, 1H); +1H for HCl salt.

Sample after chromatography dissolved in the minimum volume of ethanol, treated with a solution of hydrogen chloride in ethanol (3.8M, 1 ml), then excess diethyl ether to precipitate the hydrochloride salt.

MS (ESP): 462 (MH$^+$) for $C_{21}H_{28}FN_7O_4$

NMR (DMSO-d$_6$) δ: 2.72 (t, 2H); 2.93 (t, 4H); 3.25 (s, 3H); 3.39 (t, 2H); 3.52 (s, 2H); 3.54 (br, 2H); 3.63 (br, 2H); 3.84 (dd, 1H); 4.18 (t, 1H); 4.80 (d, 2H); 5.11 (m, 1H); 7.03 (t, 1H); 7.12 (dd, 1H); 7.41 (dd, 1H); 7.76 (d, 1H); 8.16 (d, 1H); NH missing under solvent.

The intermediate for these compounds was prepared as follows:

(5R)-3-(4-(4-(2-Chloroacetyl)piperazin-1-yl)-3-fluorophenyl)-5-(1,2,3-triazol-1-ylmethyl)oxazolidin-2-one (5R)-3-(4-(piperazin-1-yl)-3-fluorophenyl)-5-(1,2,3-triazol-1-ylmethyl)oxazolidin-2-one dihydrochloride (4.19 g, 10 mM) was suspended in dry dichloromethane (100 ml) under nitrogen and treated with triethylamine (3.03 g, 30 mM) to give a solution. After cooling to 4°, chloroacetyl chloride (1.14 g, 10 mM) was added and the mixture stirred for 15 minutes. The volume was reduced to 20 ml, and the solution chromatographed on silica, eluting with dichloromethane (30 ml). Relevant fractions were combined, washed with water (50 ml) and dried (magnesium sulfate). Evaporation gave the desired product (2.86 g).

MS (ESP): 423 (MH$^+$) for $C_{18}H_{20}ClFN_6O_3$

NMR (DMSO-d$_6$) δ:2.93 (br, 2H); 2.98 (br, 2H); 3.60 (br, 4H); 3.84 (dd, 1H); 4.18 (t, 1H); 4.41 (s, 2H); 4.81 (d, 2H); 5.11 (m, 1H); 7.06 (t, 1H); 7.13 (dd, 1H); 7.42 (dd, 1H); 7.76 (d, 1H); 8.16 (d, 1H).

EXAMPLE 17

(5R)-3-(4-((3R)-3-(t-Butoxycarbonyl)aminopyrrolidin-1-yl)-3-fluoro-phenyl)-5-(1,2,3-triazol-1-ylmethyl)oxazolidin-2-one (5R)-3-(4-((3R)-3-(t-Butoxycarbonyl)aminopyrrolidin-1-yl)-3-fluorophenyl)-5-azidomethyl-oxazolidin-2-one (695 mg, 1.65 mM) was dissolved in dioxane (30 ml), treated with norbornadiene (760 mg, 8.25 mM) and heated under reflux for 6 hours. After removal of the solvent, the residue was dissolved in the minimum of dichloromethane and purified by chromatography on a 20 g silica Mega Bond Elut® column, eluting with a gradient increasing in polarity from 0 to 2.5% methanol in dichloromethane. Relevant fractions were combined and evaporated to give the desired product (544 mg).

MS (ESP): 447 (MH$^+$) for $C_{21}H_{27}FN_6O_4$

NMR (CDCl$_3$) δ: 1.44 (s, 9H); 1.86 (m, 1H); 2.24 (m, 1H); 3.22 (d, 1H); 3.31 (t, 1H); 3.52 (m, 2H); 3.84 (dd, 1H); 4.04 (t, 1H); 4.28 (br, 1H); 4.74 (m, 3H); 5.01 (m, 1H); 6.58 (t, 1H); 6.87 (dd, 1H); 7.18 (dd, 1H); 7.73 (d, 1H); 7.78 (d, 1H).

The intermediates for this compound were prepared as follows:

3-Fluoro-4-((3R)-3-(t-butoxycarbonyl)aminoppyrrolidin-1-yl)nitrobenzene 3,4-Difluoronitrobenzene (16.03 g, 0.101 M) was dissolved in acetonitrile (300 ml), and treated with N,N-diisopropylethylamine (32.63 g, 0.253 M) and (3R)-3-(t-butoxycarbonyl)-aminopyrrolidine (20.65 g, 0.111 M). The mixture was stirred and heated to reflux for 18 hours. Solvent was evaporated, and the residue treated with ethyl acetate (300 ml) and water (200 ml). The organic layer was washed with water (150 ml), citric acid solution (10% in water, 2×150 ml), and dried (magnesium sulfate). Evaporation gave the desired product as a yellow solid (32.7 g), of sufficient quality for use without purification.

MS (ESP): 326 (MH$^+$) for $C_{15}H_{20}FN_3O_4$

NMR (CDCl$_3$): 1.43 (s, 9H); 1.85 (m, 1H); 2.25 (m, 1H); 3.44 (dt, 1H); 3.65 (overlapping m, 2H); 3.84 (dm, 1H); 4.34 (br m, 1H); 4.69 (br, 1H); 6.53 (t, 1H); 7.87 (dd, 1H); 7.92 (dd, 1H).

5-Amino-2-((3R)-3-(t-butoxycarbonyl)aminopyrrolidin-1-yl)fluorobenzene

3-Fluoro-4-((3R)-3-(t-butoxycarbonyl)aminopyrrolidin-1-yl)nitrobenzene (32.7 g, 0.101 M) was dissolved in ethyl acetate (500 ml) treated with palladium catalyst (10% on carbon, 7.5 g) and hydrogenated at atmospheric pressure until the theoretical uptake of gas. After filtration through celite and evaporation, the required product was obtained as a red gum of sufficient quality for use without purification (29.85 g). MS (ESP): 296 (MH$^+$) for $C_{15}H_{22}FN_3O_2$ NMR (CDCl$_3$) δ: 1.44 (s, 9H); 1.82 (m, 1H); 2.27 (m, 1H); 3.11 (m, 2H); 3.37 (m, 2H); 3.43 (br, 2H); 4.27 (br m, 1H); 4.82 (br, 1H); 6.38 (dd, 1H); 6.44 (dd, 1H); 6.57 (t, 1H).

5-Ethoxycarbonylamino-2-((3R)-3-(t-butoxycarbonyl)aminopyrrolidin-1-yl)fluorobenzene 5-Amino-2-((3R)-3-(t-butoxycarbonyl)aminopyrrolidin-1-yl)fluorobenzene (27.33 g, 0.093 M) was dissolved in dry pyridine (150 ml) and cooled under nitrogen with stirring to 0°. Ethyl chloroformate (11.01, 0.102 M) was added dropwise, and the mixture stirred 30 minutes at the same temperature. Ice-water (250 ml) was added, and stirring continued for 1 hour. The resulting precipitate was collected, washed thoroughly with water, and dried, to give the desired product of sufficient quality for use without purification (33.6 g).

MS (ESP): 368 (MH$^+$) for $C_{18}H_{26}FN_3O_4$

NMR (DMSO-d$_6$) δ: 1.21 (t, 3H); 1.36 (s, 9H); 1.90 (m, 1H); 2.05 (m, 1H); 3.04 (m, 1H); 3.20 (m, 1H); 3.32 (m, 1H); 3.40 (m, 1H); 4.02 (br, 1H); 4.05 (q, 2H); 6.62 (t, 1H); 7.02 (d, 1H); 7.08 (d, 1H); 7.22 (d, 1H); 9.38 (br, 1H).

(5R)-3-(3-Fluoro-4-((3R)-3-(t-butoxycarbonyl)aminopyrrolidin-1-yl)-5-hydroxymethyl-oxazolidin-2-one 5-Ethoxycarbonylamino-2-((3R)-3-(t-butoxycarbonyl) aminopyrrolidin-1-yl)fluorobenzene (33.6 g, 0.092 M) was dissolved in dry tetrahydrofuran (300 ml) under nitrogen, cooled to −70°, and treated dropwise over 30 minutes with a solution of lithium t-butoxide (1M in tetrahydrofuran, 100.7 ml), keeping the temperature below −65°. After stirring for 5 minutes, (R)-glycidylbutyrate (14.52 g, 0.101 M) was added, and stirring continued at −65° for 1 hour, before allowing the temperature to rise to ambient over 16 hours. The mixture was treated with methanol (50 ml), stirred at ambient temperature for 1 hour, and the precipitate collected and washed well with tetrahydrofuran to give the desired product (21.8 g).

MS (ESP): 396 (MH$^+$) for $C_{19}H_{26}FN_3O_5$

NMR (DMSO-d$_6$) δ: 1.36 (s, 9H); 1.80 (m, 1H); 2.07 (m, 1H); 3.09 (m, 1H); 3.26 (t, 1H); 3.35 (m, 1H); 3.49 (m, 2H); 3.62 (m, 1H); 3.73 (dd, 1H); 3.98 (t, 1H); 4.04 (m, 1H); 4.63 (m, 1H); 5.15 (t, 1H); 6.70 (t, 1H); 7.09 (dd overlapping br, 2H); 7.39 (dd, 1H).

(5R)-3-(4-((3R)-3-(i-butoxycarbonyl)aminoppyrrolidin-1-yl)-3-fluorophenyl)-5-methanesulfonyloxymethyloxazolidin-2-one (5R)-3-(4-((3R)-3-(t-butoxycarbonyl)aminopyrrolidin-1-yl)-3-fluorophenyl)-5-hydroxymethyloxazolidin-2-one (3.99 g, 10.1 mM) was suspended in dichloromethane (50 ml), and treated with triethylamine (1.53 g, 15.2 mM), then cooled under nitrogen to 0°. Methanesulfonyl chloride (1.39 g, 12.12 mM) was added dropwise, and the mixture stirred 18 hours allowing the temperature to rise to ambient. Precipitated hydrochloride was filtered, the filtrate washed with saturated sodium bicarbonate (75 ml) and water (3×75 ml), concentrated, and purified by chromatography on a 90 g silica Biotage column, eluting with dichloromethane. Relevant fractions were combined and evaporated to give desired product (1.25 g).

MS (ESP): 474 (MH$^+$) for $C_{20}H_{28}FN_3O_7S$

NMR (CDC$_3$) δ: 1.37 (s, 9H); 1.82 (m, 1H); 2.17 (m, 1H); 3.03 (s, 3H); 3.17 (d, 1H); 3.26 (t, 1H); 3.48 (m, 2H); 3.82 (dd, 1H); 4.03 (t, 1H); 4.24 (br, 1H); 4.33 (dd, 1H); 4.41 (dd, 1H); 4.72 (br, 1H); 4.83 (m, 1H); 6.57 (t, 1H); 6.96 (dd, 1H); 7.27 (dd, 1H).

(5R)-3-(4-((3R)-3-(t-butoxycarbonyl)aminopyrrolidin-1-yl)-3-fluorophenyl)-5-azidomethyl-oxazolidin-2-one (5R)-3-(4-((3R)-3-(t-butoxycarbonyl)aminopyrrolidin-1-yl)-3-fluorophenyl)-5-methane-sulfonyloxymethyloxazolidin-2-one (1.25 g, 2.64 mM) was dissolved in N,N-dimethyl-formamide (20 ml), treated with sodium azide (275 mg, 4.23 mM), and heated with stirring at 50° for 5 hours. After cooling the mixture was diluted with water (100 ml), and extracted into ethyl acetate (3×75 ml). The combined organics were dried (magnesium sulfate), and evaporated to give a yellow solid, which 5:19 PM was recrystallised from isopropanol to give the required product (715 mg).

MS (ESP): 421 (MH$^+$) for $C_{19}H_{25}FN_6O_4$

NMR (CDCl$_3$) δ:1.37 (s, 9H); 1.82 (m, 1H); 2.17 (m, 1H); 3.17 (d, 1H); 3.25 (t, 1H); 3.51 (dd overlapping m, 3H); 3.61 (dd, 1H); 3.71 (dd, 1H); 3.95 (t, 1H); 4.25 (br, 1H); 4.78 (m, 2H); 6.57 (t, 1H); 6.98 (dd, 1H); 7.28 (dd, 1H).

EXAMPLE 18

(5R)-3-(4-((3R)-3-Aminopyrrolidin-1-yl)-3-fluorophenyl)-5-(1,2,3-triazol-1-ylmethyl)oxazolidin-2-one (5R)-3-(4-((3R)-3-(t-Butoxycarbonyl)aminopyrrolidin-1-yl)-3-fluorophenyl)-5-(1,2,3-triazol-1-ylmethyl)oxazolidin-2-one (532 mg, 1.2 mM), was dissolved in dichloromethane (10 ml), and treated with a solution of hydrogen chloride in ethanol (3.8M, 2 ml). After stirring 4 hours at ambient temperature, the precipitated hydrochloride of the product (230 mg) was filtered, and the filtrate diluted with diethyl ether to deposit more product (218 mg).

MS (ESP): 347 (MH$^+$) for $C_{16}H_{19}FN_6O_2$

NMR (DMSO-d$_6$) δ: 2.03 (m, 1H); 2.25 (m, 1H); 3.25 (dd, 1H); 3.41 (m, 1H); 3.51 (m, 2H); 3.82 (overlapping m, 2H); 4.17 (t, 1H); 4.81 (d, 2H); 5.08 (m, 1H); 6.74 (t overlapped by H$_2$O, ~1H); 7.05 (dd, 1H); 7.32 (dd, 1H); 7.74 (d, 1H); 8.15 (d, 1H); 8.43 (br, ~2H).

EXAMPLE 19

(5R)-3-(4-((3R)-3-Methoxycarbonylaminopyrrolidin-1-yl)-3-fluorophenyl)-5-(1,2,3-triazol-1-ylmethyl)oxazolidin-2-one (5R)-3-(4-((3R)-3-Aminopyrrolidin-1-yl)-3-fluorophenyl)-5-(1,2,3-triazol-1-ylmethyl)oxazolidin-2-one hydrochloride (200 mg, 0.5 mM) in dichloromethane (20 ml) was cooled to 0° and treated with 5% sodium bicarbonate solution (5 ml). The resulting suspension was stirred vigorously, methyl chloroformate (245 mg, 2.6 mM) added, and stirring continued for 3 hours at ambient temperature. The organic layer was separated, washed with 2% sodium dihydrogen phosphate (2×10 ml), brine (10 ml), and dried (magnesium sulfate), to give the desired product (143 mg).

MS (ESP): 405 (MH$^+$) for $C_{18}H_{21}FN_6O_4$

NMR (DMSO-d$_6$) δ: 1.82 (m, 1H); 2.11 (m, 1H); 3.13 (m, 1H); 3.27 (dd, 1H); 3.37 (dd, 1H); 3.53 (s overlapping m, 4H); 3.81 (dd, 1H); 4.09 (m, 1H); 4.15 (t, 1H); 4.80 (d, 2H); 5.08 (m, 1H); 6.69 (t, 1H); 7.01 (dd, 1H); 7.28 (dd, 1H); 7.42 (br, 1H); 7.75 (d, 1H); 8.13 (d, 1H).

EXAMPLE 20

(5R)-3-(4-((3R)-3-((4S)-2,2-dimethyl-1,3-dioxolan-4-ylmethoxy-carbonylamino)pyrrolidin-1-yl)-3-fluorophenyl)-5-(1,2,3-triazol-1-ylmethyl)oxazolidin-2-one (5R)-3-(4-((3R)-3-Aminopyrrolidin-1-yl)-3-fluorophenyl)-5-(1,2,3-triazol-1-ylmethyl)-oxazolidin-2-one hydrochloride (400 mg, 1.05 mM) was suspended in tetrahydrofuran (10 ml) and treated with diisopropylethylamine (176 mg, 1.36 mM) and (4S)-2,2-dimethyl-1,3-dioxolan-4-ylmethyl 4-nitrophenyl carbonate (429 mg, 1.44 mM) dissolved in dichloromethane (5 ml). The mixture was stirred vigorously at ambient temperature for 18 hours, with the addition of two further portions of diisopropylethylamine (137 mg, 1.06 mM). Solvent was evaporated, the residue redissolved in ethyl acetate (20 ml), washed with water (3×20 ml), and dried (magnesium sulfate). After removal of the solvent, the residue was purified by chromatography on a 10 g silica Mega Bond Elut® column, eluting with a gradient increasing in polarity from 0 to 5% methanol in dichloromethane. Relevant fractions were combined and evaporated to give the desired product (273 mg).

MS (ESP): 505 (MH$^+$) for $C_{23}H_{29}FN_6O_6$

NMR(DMSO-d$_6$) δ: 1.25 (s, 3H); 1.31 (s, 3H); 1.84 (m, 1H); 2.10 (m, 1H); 3.15 (m, 1H); 3.38 (dd, 1H); 3.50 (t, 1H); 3.63 (t, 1H); 3.81 (dd, 1H); 3.91 (m, 1H); 3.95–4.25 (overlapping m, 6H); 4.79 (d, 2H); 5.08 (m, 1H); 6.69 (t, 1H); 7.01 (dd, 1H); 7.28 (dd, 1H); 7.57 (br, 1H); 7.75 (d, 1H); 8.14 (d, 1H).

The reagent for this compound was prepared as follows:

(4S)-2,2-Dimethyl-1,3-dioxolan-4-ylmethyl 4-nitrophenyl carbonate (4S)-2,2-Dimethyl-1,3-dioxolan-4-ylmethanol (362 mg, 2.74 mM) was dissolved in pyridine (9 ml), stirred at ambient temperature, and treated in portions with 4-nitrophenyl chloroformate (552 mg, 2.74 mM). After 6 hours, solvent was evaporated, the residue redissolved in ethyl acetate (15 ml), washed with water (15 ml), sodium bicarbonate solution (15 ml), brine (15 ml), and dried (magnesium sulfate). Removal of the solvent gave the product as an oil sufficiently pure for further use (858 mg).

MS (ESP): 298 (MH$^+$) for $C_{13}H_{15}NO_7$

NMR (DMSO-d$_6$) δ: 1.28 (s, 3H); 1.34 (s, 3H); 3.74 (dd, 1H); 4.05 (t, 1H); 4.20 (dd, 1H); 4.25 (dd, 2H); 7.54 (d, 2H); 8.29 (d, 2H).

EXAMPLE 21

(5R)-3-(4-((3R)-3-((2S)-2,3-Dihydroxypropyloxycarbonylamino)pyrrolidin-1-yl)-3-fluorophenyl)-5-(1,2,3-triazol-1-ylmethyl)oxazolidin-2-one (5R)-3-(4-((3R)-3-((4S)-2,2-Dimethyl-1,3-dioxolan-4-ylmethoxycarbonylamino)pyrrolidin-1-yl)-3-fluorophenyl)-5-(1,2,3-triazol-1-ylmethyl)oxazolidin-2-one (240 mg, 0.48 mM) in tetrahydrofuran (5 ml) was treated with hydrochloric acid (2M, 2 ml) and stirred at ambient temperature for 18 hours. Solid potassium carbonate was added to neutralise, and the mixture filtered, and the filtrate evaporated to dryness. The residue was purified by chromatography on a 10 g silica Mega Bond Elut® column, eluting with a gradient increasing in polarity from 0 to 10% methanol in dichloromethane. Relevant fractions were combined and evaporated to give the desired product (170 mg).

MS (ESP): 465 (MH$^+$) for $C_{20}H_{25}FN_6O_6$

NMR(DMSO-d$_6$) δ: 1.83 (hextet, 1H); 2.10 (hextet, 1H); 3.15 (s, 1H); 3.17 (s, 1H); 3.33 (t, 2H); 3.50 (t, 1H); 3.60 (dd, 1H); 3.80 (dd, 1H); 3.84 (dd, 1H); 3.97 (dd, 1H); 4.05 (dd, 1H); 4.09 (d, 1H); 4.15 (t, 1H); 4.54 (t, 1H); 4.73 (d, 1H); 4.80 (d, 2H); 5.08 (m, 1H); 6.69 (t, 1H); 7.00 (dd, 1H); 7.27 (dd, 1H); 7.43 (d, 1H); 7.74 (d, 1H); 8.13 (d, 1H).

EXAMPLE 22

(5R)-3-(4-((3R)-3-(2-Methoxyethoxycarbonylamino)pyrrolidin-1-yl)-3-fluorophenyl)-5-(1,2,3-triazol-1-ylmethyl)oxazolidin-2-one (5R)-3-(4-((3R)-3-Aminopyrrolidin-1-yl)-3-fluorophenyl)-5-(1,2,3-triazol-1-ylmethyl)-oxazolidin-2-one hydrochloride (200 mg, 0.52 mM) was suspended by stirring in dichloromethane (10 ml) at 0° and sodium bicarbonate solution (5 ml) added. 2-Methoxyethyl chloroformate (340 mg, 2.46 mM) was added, and the mixture stirred 4 hours, allowing the temperature to rise to ambient. The organic layer was separated, washed with sodium dihydrogen phosphate (2%, 2×15 ml), water (15 ml) and dried (magnesium sulfate). Filtration and evaporation gave the desired product (183 mg).

MS (ESP): 449 (MH$^+$) for $C_{20}H_{25}FN_6O_5$

NMR (DMSO-d$_6$) δ: 1.82 (hextet, 1H); 2.10 (hextet, 1H); 3.13 (m, 1H); 3.24 (s, 3H); 3.36 (t, 1H); 3.48 (m, 4H); 3.79 (dd, 1H); 4.05 (m, 3H); 4.16 (t, 1H); 4.79 (d, 2H); 5.08 (m, 1H); 6.69 (t, 1H); 7.01 (dd, 1H); 7.28 (dd, 1H); 7.51 (d, 1H); 7.74 (d, 1H); 8.13 (d, 1H).

EXAMPLE 23

(5R)-3-(4-((3R)-3-(2-Hydroxyethoxycarbonylamino)pyrrolidin-1-yl)-3-fluorophenyl)-5-(1,2,3-triazol-1-ylmethyl)oxazolidin-2-one The resin bearing the title compound bound via its terminal hydroxy group (200 mg, nominal 0.118 mM) was swelled in dichloromethane (2 ml) for 30 minutes. Excess solvent was drained, and a solution of trifluoroacetic acid (1% in dichloromethane, 1 ml) was added, and the mixture agitated at ambient temperature for 2 hours. The resin was washed repeatedly with dichloromethane (5×5 ml), and the combined washings concentrated. The gum so obtained was azeotroped with isohexane/dichloromethane (20 ml) to give the desired product (40 mg).

MS (ESP): 435 (MH$^+$) for $C_{19}H_{23}FN_6O_5$

NMR (DMSO-d$_6$) δ:1.85 (hextet, 1H); 2.10 (hextet, 1H); 3.17 (m, 1H); 3.28 (dd, 1H); 3.41 (dd, 1H); 3.51 (m, 2H); 3.82 (dd, 1H); 3.97 (t, 1H); 4.12 (m, 1H); 4.17 (t, 1H); 4.29 (m, 1H); 4.55 (m, 1H); 4.81 (d, 2H); 5.10 (m, 1H); 6.69 (t, 1H); 7.01 (dd, 1H); 7.27 (dd, 1H); 7.46 (d, 1H); 7.75 (d, 1H); 8.15 (d, 1H); 1×OH exchanging, not seen.

The intermediates for this compound were prepared as follows:

A polystyrene resin derivatised with 2-hydroxyethoxy-2'-chlorotrityl functionality (Novabiochem, 0.59 mM/g, 250 mg, 0.148 mM) was swelled in base-washed dichloromethane (3 ml) for 30 minutes, then excess dichloromethane drained. A solution of 4-nitrophenyl chloroformate (149 mg, 0.738 mM) and pyridine (175 mg, 2.22 mM) in base-washed dichloromethane was added, and the mixture shaken gently for 18 hours at ambient temperature. Solvent was then drained, and the resin washed with several portions of dichloromethane, then diethyl ether and dried in a desiccator.

IR: 1768; 1596; 1264 cm$^{-1}$.

The above resin (200 mg, nominally 0.118 mM) was swelled in N,N-dimethylacetamide (3 ml) for 30 minutes, solvent drained, and a pre-mixed solution of (5R)-3-(4-((3R)-3-aminopyrrolidin-1-yl)-3-fluorophenyl)-5-(1,2,3-triazol-1-ylmethyl)oxazolidin-2-one hydrochloride (226 mg, 0.59 mM) and diisopropylethylamine (228 mg, 1.77 mM) in N,N-dimethylacetamide (3 ml) added. The mixture was shaken gently for 4 hours at ambient temperature. Solvent was then drained, and the resin washed with N,N-dimethylacetamide (3×4 ml), then dichloromethane (3×4 ml), and dried in a desiccator. IR: 3409; 1758; 1725 compound$^{-1}$.

EXAMPLE 24

(5R)-3-(4-((3S)-3-(t-Butoxycarbonyl)aminopyrrolidin-1-yl)-3-fluoro-phenyl)-5-(1,2,3-triazol-1-ylmethyl)oxazolidin-2-one (5R)-3-(4-((3S)-3-(t-Butoxycarbonyl)aminopyrrolidin-1-yl)-3-fluorophenyl)-5-azidomethyl-oxazolidin-2-one (3.2 g, 7.61 mM) was reacted by essentially the technique of Example 17 and purified by chromatography on a 60 g silica Biotage column, eluting with a gradient increasing in polarity from 0 to 7% methanol in dichloromethane. Relevant fractions were combined and evaporated to give the desired product (1.66 g).

MS (ESP): 447 (MH$^+$) for $C_{21}H_{27}FN_6O_4$

NMR (DMSO-d$_6$) δ: 1.39 (s, 9H); 1.84 (m, 1H); 2.10 (m, 1H); 3.12 (m, 1H); 3.27 (t, 1H); 3.38 (m, 1H); 3.50 (t, 1H); 3.83 (dd, 1H); 4.06 (m, 1H); 4.18 (t, 1H); 4.82 (d, 2H); 5.11 (m, 1H); 6.71 (t, 1H); 7.03 (dd, 1H); 7.13 (br, 1H); 7.30 (dd, 1H); 7.77 (d, 1H); 8.16 (d, 1H).

The intermediates for this compound were prepared as follows:

3-Fluoro-4-((3S)-3-(t-butoxycarbonyl)aminopyrrolidin-1-yl)nitrobenzene

Using essentially the technique for the equivalent intermediate in Example 17, but starting from (3S)-3-(t-butoxycarbonyl)aminopyrrolidine (20 g, 0.108 M), gave the desired product as a yellow solid (33.5 g), of sufficient quality for use without purification.

MS (ESP): 326 (MH$^+$) for $C_{15}H_{20}FN_3O_4$

NMR (DMSO-d$_6$) δ: 1.36 (s, 9H); 1.87 (m, 1H); 2.08 (m, 1H); 3.36 (m, 1H); 3.54 (m, 1H); 3.62 (tm, 1H); 3.73 (m, 1H); 4.09 (m, 1H); 6.72 (t, 1H); 7.19 (d, 1H); 7.88 (overlapping m, 2H).

5-Amino-2-((3S)-3-(t-butoxycarbonyl)aminoppyrrolidin-1-yl)fluorobenzene

Using essentially the technique for the equivalent intermediate in Example 17, but starting from 3-fluoro-4-((3S)-3-(t-butoxycarbonyl)aminopyrrolidin-1-yl)nitrobenzene (33.5 g, 0.103 M), gave the desired product as an oil of sufficient quality for use without purification (~30 g).

MS (ESP): 296 (MH$^+$) for $C_{15}H_{22}FN_3O_2$

NMR (DMSO-d$_6$) δ: 1.35 (s, 9H); 1.71 (m, 1H); 2.06 (m, 1H); 2.87 (dd, 1H); 3.05 (m, 1H); 3.11 (m, 1H); 3.26 (m overlapping H$_2$O, 1H); 3.97 (m, 1H); 4.68 (s, 2H); 6.25 (dd, 1H); 6.31 (dd, 1H); 6.51 (t, 1H); 7.03 (d, 1H).

5-Ethoxycarbonylamino-2-((3S)-3-(t-butoxycarbonyl)aminopyrrolidin-1-yl)fluorobenzene Using essentially the technique for the equivalent intermediate in Example 17, but starting from 5-amino-2-((3S)-3-(t-butoxycarbonyl)aminopyrrolidin-1-yl)fluorobenzene (30.4 g, 0.103 M), gave crude product after precipitation. This was purified by dissolving in toluene (500 ml), azeotroping until product began to precipitate, then cooling and adding isohexane (500 ml) to complete precipitation. Filtration gave the desired product (35.3 g).

MS (ESP): 368 (MH$^+$) for $C_{18}H_{26}FN_3O_4$

NMR (DMSO-d$_6$) δ: 1.21 (t, 3H); 1.37 (s, 9H); 1.77 (m, 1H); 2.06 (m, 1H); 3.04 (m, 1H); 3.20 (dd, 1H); 3.30 (m overlapping H$_2$O, 1H); 3.42 (tm, 1H); 4.02 (br, 1H); 4.08 (q, 2H); 6.63 (t, 1H); 7.02 (d, 1H); 7.08 (br, 1H); 7.22 (d, 1H); 9.38 (s, 1H).

(5R)-3-(3-Fluoro-4-((3S)-3-(t-butoxycarbonyl)aminopyrrolidin-1-yl)-5-hydroxymethyl-oxazolidin-2-one 5-Ethoxycarbonylamino-2-((3S)-3-(t-butoxycarbonyl)aminopyrrolidin-1-yl)fluorobenzene (35.2 g, 0.096 M) was dissolved in dry tetrahydrofuran (400 ml) under nitrogen, cooled to −70°, and treated dropwise over 20 minutes with a solution of lithium t-butoxide, prepared from t-butanol (9.3 g, 123 mM) in dry tetrahydrofuran (70 ml) and n-butyl lithium (66 ml, 1.6M in hexane). After stirring for 20 minutes, (R)-glycidylbutyrate (15.2 g, 0.102 M) in tetrahydrofuran (20 ml) was added over 10 minutes, and the temperature allowed to rise to ambient over 16 hours. The mixture was treated with methanol (10 ml), stirred at ambient temperature for 10 minutes, then treated with a mixture of 5% aqueous sodium bicarbonate (250 ml) and ethyl acetate (500 ml). The precipitate was collected and washed well with ethyl acetate and water to give the desired product (19.5 g). The filtrate was separated into an organic layer, which was dried (magnesium sulfate) and evaporated. The residue was refluxed briefly with ethyl acetate (100 ml), cooled, and filtered to give further product (16.6 g)

MS (ESP): 396 (MH$^+$) for $C_{19}H_{26}FN_3O_5$

NMR (DMSO-d$_6$) δ: 1.37 (s, 9H); 1.79 (m, 1H); 2.07 (m, 1H); 3.08 (m, 1H); 3.24 (m overlapping H$_2$O, ~1H); 3.36 (m, 1H); 3.48 (tm, 1H); 3.53 (d, 1H); 3.63 (d, 1H); 3.74 (dd, 1H); 3.99 (t, 1H); 4.04 (m, 1H); 4.63 (m, 1H); 5.15 (s, 1H); 6.71 (t, 1H); 7.08 (dd over-lapping br, 2H); 7.39 (dd, 1H).

(5R)-3-(4-((3S)-3-(t-Butoxycarbonyl)aminoppyrrolidin-1-yl)-3-fluorophenyl)-5-methane-sulfonyloxymethyloxazolidin-2-one (5R)-3-(4-((3S)-3-(t-Butoxycarbonyl)aminopyrrolidin-1-yl)-3-fluorophenyl)-5-hydroxy-methyloxazolidin-2-one (3.04 g, 7.7 mM) was suspended in a mixture of dichloromethane (25 ml) and pyridine (20 ml), cooled under nitrogen to 0°, and treated with triethylamine (1.15 g, 11.4 mM). Methanesulfonyl chloride (1.04 g, 9.1 mM) in dichloromethane (5 ml) was added dropwise, and the mixture stirred 45 minutes at the same temperature. The mixture was concentrated to dryness, and the residue dissolved in ethyl acetate (70 ml), then washed with 5% sodium bicarbonate (70 ml), water (2×70 ml), brine (70 ml), and dried (magnesium sulfate). After evaporation and azeotroping with toluene (20 ml), product of sufficient quality was obtained for use without further purification (3.64 g).

MS (ESP): 474 (MH$^+$) for $C_{20}H_{20}FN_3O_7S$

NMR (DMSO-d$_6$) δ: 1.37 (s, 9H); 1.81 (m, 1H); 2.08 (m, 1H); 3.11 (m, 1H); 3.26 (s, 3H); 3.28 (m, 1H); 3.38 (m, 1H); 3.49 (tm, 1H); 3.76 (dd, 1H); 4.05 (m, 1H); 4.11 (t, 1H); 4.43 (dd, 1H); 4.50 (dd, 1H); 4.96 (m, 1H); 6.72 (t, 1H); 7.10 (dd, 1H); 7.16 (d, 1H); 7.49 (dd, 1H).

(5R)-3-(4-((3S)-3-(t-Butoxycarbonyl)aminoppyrrolidin-1-yl)-3-fluorophenyl)-5-azidomethyl-oxazolidin-2-one (5R)-3-(4-((3S)-3-(t-Butoxycarbonyl)aminopyrrolidin-1-yl)-3-fluorophenyl)-5-methane-sulfonyloxymethyloxazolidin-2-one (3.6 g, 7.61 mM) was dissolved in N,N-dimethylformamide (40 ml), treated with sodium azide (0.99 g, 15.2 mM), and heated with stirring at 80° for 3.5 hours. After cooling the mixture was diluted with water (400 ml), and extracted into ethyl acetate (400 ml). The combined organics were washed with water (2×400 ml) and brine (200 ml), dried (magnesium sulfate), and evaporated to give the required product (3.2 g).

MS (ESP): 421 (MH$^+$) for $C_{19}H_{25}FN_6O_4$

EXAMPLE 25

(5R)-3-(4-((3S)-3-Aminopyrrolidin-1-yl)-3-fluorophenyl)-5-(1,2,3-triazol-1-ylmethyl)oxazolidin-2-one (5R)-3-(4-((3S)-3-(t-Butoxycarbonyl)aminopyrrolidin-1-yl)-3-fluorophenyl)-5-(1,2,3-triazol-1-ylmethyl)oxazolidin- 2-one (1.55 g, 3.47 mM), was dissolved in dichloromethane (8 ml), and treated with a solution of hydrogen chloride in ethanol (3.8M, 40 ml). After stirring 2 hours at ambient temperature, the mixture was evaporated to dryness to give product as a hydrochloride of sufficient quality to require no purification (1.64 g).

MS (ESP): 347 (MH$^+$) for $C_{16}H_{19}FN_6O_2$

NMR (DMSO-d$_6$) δ: 2.00 (m, 1H); 2.25 (m, 1H); 3.24 (dd, 1H); 3.41 (m, 1H); 3.52 (m, 2H); 3.82 (overlapping m, 2H); 4.17 (t, 1H); 4.81 (d, 2H); 5.10 (m, 1H); 6.78 (t, 1H); 7.06 (dd, 1H); 7.33 (dd, 1H); 7.76 (d, 1H); 8.17 (d, 1H); 8.36 (br, ~2H).

EXAMPLE 26

(5R)-3-(4-((3S)-3-Acetamidopyrrolidin-1-yl)-3-fluorophenyl)-5-(1,2,3-triazol-1-ylmethyl)oxazolidin-2-one Using essentially the technique of Example 19, but starting from (5R)-3-(4-((3S)-3-aminopyrrolidin-1-yl)-3-fluorophenyl)-5-(1,2,3-triazol-1-ylmethyl)oxazolidin-2-one hydrochloride (250 mg, 0.65 mM), and replacing the methyl chloroformate with acetic anhydride gave the desired product (150 mg).

MS (ESP): 405 (MH$^+$) for $C_{18}H_{21}FN_6O_3$

NMR (DMSO-d$_6$) δ: 1.87 (s overlapping m, 4H); 2.16 (m, 1H); 3.18 (m, 1H); 3.33 (dd, 1H); 3.46 (t, 1H); 3.56 (tm, 1H); 3.88 (dd, 1H); 4.24 (t, 1H); 4.35 (m, 1H); 4.88 (d, 2H); 5.15 (m, 1H); 6.89 (t, 1H); 7.08 (dd, 1H); 7.37 (dd, 1H); 7.84 (d, 1H); 8.19 (d, 1H); 8.23 (d, 1H).

EXAMPLE 27

(5R)-3-(4-((3S)-3-Methoxycarbonylaminopyrrolidin-1-yl)-3-fluorophenyl)-5-(1,2,3-triazol-1-ylmethyl) oxazolidin-2-one Using essentially the technique of Example 19, but starting from (5R)-3-(4-((3S)-3-aminopyrrolidin-1-yl)-3-fluorophenyl)-5-(1,2,3-triazol-1-ylmethyl)oxazolidin-2-one hydrochloride (250 mg, 0.65 mM) gave the desired product (192 mg).

MS (ESP): 405 (MH$^+$) for $C_{18}H_{21}FN_6O_4$

NMR (DMSO-d$_6$) δ: 1.82 (m, 1H); 2.11 (m, 1H); 3.13 (m, 1H); 3.31 (m overlapping H$_2$O, ~2H); 3.51 (s overlapping m, 4H); 3.81 (dd, 1H); 4.07 (m, 1H); 4.17 (t, 1H); 4.80 (d, 2H); 5.08 (m, 1H); 6.71 (t, 1H); 7.02 (dd, 1H); 7.27 (dd, 1H); 7.47 (d, 1H); 7.76 (d, 1H); 8.15 (d, 1H).

EXAMPLE 28

(5R)-3-(4-((3S)-3-Methanesulfonamidopyrrolidin-1-yl)-3-fluorophenyl)-5-(1,2,3-triazol-1-ylmethyl)oxazolidin-2-one (5R)-3-(4-((3S)-3-Aminopyrrolidin-1-yl)-3-fluorophenyl)-5-(1,2,3-triazol-1-ylmethyl)-oxazolidin-2-one hydrochloride (250 mg, 0.65 mM), in dichloromethane (20 ml) was cooled to 0° and treated with 5% sodium bicarbonate solution (10 ml). The resulting suspension was stirred vigorously, methanesulfonyl chloride (290 mg, 2.5 mM) added, and stirring continued for 18 hours at ambient temperature. Dichloromethane (10 ml) was added, the organic layer separated, and diluted with isohexane (30 ml). The precipitate was filtered, triturated with 2% sodium dihydrogen phosphate, and purified by chromatography on a 2 g silica Mega Bond Elut® column, eluting with a gradient increasing in polarity from 0 to 8% methanol in dichloromethane. Relevant fractions were combined and evaporated to give the desired product (28 mg).

MS (ESP): 425 (MH$^+$) for $C_{17}H_{21}FN_6O_4S$

NMR (DMSO-d$_6$) δ: 1.84 (m, 1H); 2.18 (m, 1H); 2.93 (s, 3H); 3.18 (m, 1H); 3.34 (m overlapping H$_2$O, ~2H); 3.54 (t, 1H); 3.80 (dd, 1H); 3.96 (dd, 1H); 4.15 (t, 1H); 4.49 (d, 2H); 5.08 (m, 1H); 6.71 (t, 1H); 7.01 (dd, 1H); 7.28 (dd, 1H); 7.34 (d, 1H); 7.74 (d, 1H); 8.13 (d, 1H).

EXAMPLE 29

(5R)-3-(4-Imidazol-1-yl-3-fluorophenyl)-5-(1,2,3-triazol-1-ylmethyl)-oxazolidin-2-one (5R)-3-(4-Imidazol-1-yl-3-fluorophenyl)-5-azidomethyloxazolidin-2-one (755 mg, 1.35 mM) was dissolved in dioxane (40 ml), treated with norbornadiene (115 g, 12.5 mM) and heated under reflux for 16 hours. After removal of the solvent, the residue was dissolved in the minimum of dichloromethane and purified by chromatography on a 20 g silica Mega Bond Elut® column, eluting with a gradient increasing in polarity from 0 to 10% methanol in dichloromethane. Relevant fractions were combined and evaporated to give the desired product (660 mg).

MS (ESP): 329 (MH$^+$) for $C_{15}H_{13}FN_6O_2$

NMR (DMSO-d$_6$) δ: 3.95 (dd, 1H); 4.29 (t, 1H); 4.85 (d, 2H); 5.16 (m, 1H); 7.11 (d, 1H); 7.39 (dd, 1H); 7.54 (overlapping m, 2H); 7.66 (d, 1H); 7.77 (d, 1H); 7.98 (m, 1H); 8.18 (d, 1H).

(Intermediate oxazolidinone described in Upjohn WO 96-23788)

EXAMPLE 30

(5R)-3-(4-Imidazol-1-yl-3-fluorophenyl)-5-(1-pyrazolyl)methyl)oxazolidin-2-one

Sodium hydride (60% in oil, 32 mg, 0.8 mM) was stirred under nitrogen in N,N-dimethylformamide (2 ml), pyrazole (68 mg, 1 mM) added, and stirring continued for 10 minutes. (5R)-3-(4-Imidazol-1-yl-3-fluorophenyl)-5-methanesulfonyloxymethyloxazolidin-2-one (142 mg, 0.4 mM) was dissolved in N,N-dimethylformamide (1 ml), added to the above, and the mixture stirred 18 hours at ambient temperature. After diluting with 5% aqueous sodium bicarbonate (30 ml), the mixture was extracted with ethyl acetate (50 ml), the extract washed with water (2×30 ml), brine (25 ml), dried (magnesium sulfate) and evaporated. The residue was dissolved in the minimum of dichloromethane and purified by chromatography on a 10 g silica Mega Bond Elut® column, eluting with a gradient increasing in polarity from 0 to 15% isopropanol in dichloromethane. Relevant fractions were combined and evaporated, then dissolved in dichloromethane (5 ml) and stirred for 18 hours with PS-Isocyanate resin (Argonaut Technologies, 500 mg) to remove ring opened impurities. Filtration and evaporation gave the desired product (34 mg).

MS (ESP): 328 (MH$^+$) for $C_{16}H_{14}FN_5O_2$

NMR (DMSO-d$_6$) δ: 3.89 (dd, 1H); 4.17 (t, 1H); 4.46 (d, 2H); 5.04 (m, 1H); 6.21 (t, 1H); 7.08 (m, 1H); 7.32 (dd, 1H); 7.39 (d, 1H); 7.50 (m, 1H); 7.58 (t, 1H); 7.60 (dd, 1H); 7.72 (d, 1H); 8.00 (m, 1H).

(Intermediate described in WO 96-23788)

EXAMPLE 31

(5R)-3-(4-Imidazol-1-yl-3-fluorophenyl)-5-tetrazol-1-ylmethyloxazolidin-2-one and (5R)-3-(4-Imidazol-1-yl-3-fluorophenyl)-5-tetrazol-2-ylmethyloxazolidin-2-one (5R)-3-(4-Imidazol-1-yl-3-fluorophenyl)-5-methanesulfonyloxymethyloxazolidin-2-one (249 mg, 0.7 mM) was dissolved in N,N-dimethylformamide (2 ml), treated with 1H-tetrazole (123 mg, 1.75 mM) and potassium carbonate (241 mg, 1.75 mM), and heated at 95° for 3 hours. After cooling, the mixture was diluted with water (30 ml), extracted with ethyl acetate (50 ml), the extract washed with water (2×30 ml), brine (25 ml), dried (magnesium sulfate) and evaporated. The residue was dissolved in the minimum of dichloromethane and purified by chromatography on a 10 g silica Mega Bond Elut®(column, eluting with a gradient increasing in polarity from 0 to 10% isopropanol in dichloromethane, then 0 to 20% methanol in dichloromethane. Relevant fractions were combined and evaporated, the first eluting product being the 2-isomer (80 mg).

MS (ESP): 330 (MH$^+$) for $C_{14}H_{12}FN_7O_2$

NMR (DMSO-$d_6$) δ: 3.96 (dd, 1H); 4.34 (t, 1H); 5.26 (overlapping m, 3H); 7.12 (m, 1H); 7.40 (dd, 1H); 7.55 (d, 1H); 7.66 (t overlapping dd, 2H); 8.00 (m, 1H); 9.05 (s, 1H).

The second eluting product was the 1-isomer (51 mg).

MS (ESP): 330 (MH$^+$) for $C_{14}H_{12}FN_7O_2$

NMR (DMSO-$d_6$) δ: 3.98 (dd, 1H); 4.31 (t, 1H); 4.95 (m, 2H); 5.21 (m, 1H); 7.12 (m, 1H); 7.43 (dd, 1H); 7.55 (d, 1H); 7.67 (t overlapping dd, 2H); 8.01 (m, 1H); 9.49 (s, 1H). Intermediate described in WO 96-23788.

EXAMPLE 32

(5R)-3-(4-(4-Hydroxymethylimidazol-1-yl)-3-fluorophenyl)-5-tetrazol-1-ylmethyloxazolidin-2-one and (5R)-3-(4-(4-Hydroxymethylimidazol-1-yl)-3-fluorophenyl)-5-tetrazol-2-ylmethyloxazolidin-2-one (5R)-3-(4-(4-t-Butyldimethylsilyloxymethylimidazol-1-yl)-3-fluorophenyl)-5-hydroxy-methyloxazolidin-2-one (421 mg, 1 mM), 1H-tetrazole (105 mg, 1.5 mM), and triphenyl-phosphine (393 mg, 1.5 mM) were dissolved by stirring in dry tetrahydrofuran (5 ml) under nitrogen in an ice-bath. Diisopropylazodicarboxylate (303 mg, 1.5 mM) was added dropwise, and the mixture stirred 2 hours, allowing the temperature to rise to ambient. The mixture was cooled to 0°, treated with trifluoroacetic acid (5 ml), and stirred 30 minutes at ambient temperature. The mixture was diluted with ethyl acetate (100 ml), and extracted with aqueous hydrochloric acid (1 M, 100 ml). The acid extract was washed with ethyl acetate (100 ml), then made basic with concentrated aqueous ammonia, and reextracted with dichloromethane. After drying (magnesium sulfate), the residue was purified by chromatography on a 10 g silica Mega Bond Elut® column, eluting with a gradient increasing in polarity from 0 to 10% methanol in dichloromethane. Relevant fractions were combined to give the less polar tetrazol-2-yl isomer (105 mg).

MS (ESP): 360 (MH$^+$) for $C_{15}H_{14}FN_7O_3$

NMR (DMSO-$d_6$) δ: 3.96 (dd, 1H); 4.32 (t, 1H); 4.39 (d, 2H); 4.96 (t, 1H); 5.16 (dd, 1H); 5.25 (dd, 1H); 5.31 (m, 1H); 7.32 (d, 1H); 7.38 (dd, 1H); 7.63 (t, 1H); 7.66 (dd, 1H); 7.90 (d, 1H); 9.02 (s, 1H).

The aqueous ammonia liquors were cooled to 4° overnight, to precipitate crystals of the more polar tetrazol-1-yl isomer (6 mg).

MS (ESP): 360 (MH$^+$) for $C_{14}H_{12}FN_7O_2$

The oxazolidinone intermediate is described in WO 97-31917.

EXAMPLE 33

(5R)-3-(4-(2-Methylimidazol-1-yl)-3-fluorophenyl)-5-tetrazol-1-yl-methyloxazolidin-2-one and (5R)-3-(4-(2-Methylimidazol-1-yl)-3-fluorophenyl)-5-tetrazol-2-ylmethyloxazolidin-2-one Essentially the technique of Example 17 was used, but starting from (5R)-3-(4-(2-methylimidazol-1-yl)-3-fluorophenyl)-5-hydroxymethyloxazolidin-2-one (582 mg, 2 mM). Crude material from the acid extract was purified by chromatography on a 20 g silica Mega Bond Elut® column, eluting with a gradient increasing in polarity from 0 to 20% methanol in dichloromethane. Relevant fractions of the first eluting product were combined to give the less polar tetrazol-2-yl isomer (246 mg).

MS (ESP): 344 (MH$^+$) for $C_{15}H_{14}FN_7O_2$

NMR (DMSO-$d_6$) δ: 2.14 (s, 3H); 3.97 (dd, 1H); 4.34 (t, 1H); 5.16 (dd, 1H); 5.26 (dd, 1H); 5.32 (m, 1H); 6.91 (d, 1H); 7.20 (d, 1H); 7.40 (dd, 1H); 7.54 (t, 1H); 7.66 (dd, 1H); 9.02 (s, 1H).

The second eluting product was the 1-isomer (210 mg).

MS (ESP): 344 (MH$^+$) for $C_{15}H_{14}FN_7O_2$

NMR (DMSO-$d_6$) δ: 2.13 (s, 3H); 3.97 (dd, 1H); 4.31 (t, 1H); 4.94 (d, 2H); 5.21 (m, 1H); 6.91 (d, 1H); 7.20 (d, 1H); 7.42 (dd, 1H); 7.55 (t, 1H); 7.67 (dd, 1H); 9.47 (s, 1H).

The intermediates for these compounds were prepared as follows:

3-Fluoro-4-(2-methylimidazol-1-yl)nitrobenzene

2-Methylimidazole (9.02 g, 0.11 M) and N,N-diisopropylethylamine (32.2 g, 0.25 M) were dissolved in acetonitrile (160 ml), and 3,4-difluoronitrobenzene (15.9 g, 0.1 M) added. The mixture was stirred and heated to reflux under nitrogen for 24 hours. Solvent was evaporated, the residue dissolved in ethyl acetate (300 ml), washed with water (150 ml), brine (150 ml), and dried (magnesium sulfate). The residue was recrystallised from a mixture of ethyl acetate (25 ml) and cyclohexane (150 ml) with the addition of charcoal to give the title compound (11.5 g), mp 106–107°.

MS (ESP): 222 (MH$^+$) for $C_{10}H_8FN_3O_2$

NMR (DMSO-$d_6$) δ: 2.25 (s, 3H); 7.00 (d, 1H); 7.35 (t, 1H); 7.87 (t, 1H); 8.23 (dd, 1H); 8.43 (dd, 1H).

5-Amino-2-(2-methylimidazol-1-yl)fluorobenzene

3-Fluoro-4-(2-methylimidazol-1-yl)nitrobenzene (40 g, 0.181 M) was dissolved in a mixture of methanol (200 ml) and tetrahydrofuran (800 ml), cooled to 0° under nitrogen, and treated with ammonium formate (57 g, 0.905 M) followed by palladium on charcoal (10%, 2 g). The mixture was stirred at ambient temperature for 18 hours, filtered through celite, celite washed with methanol (100 ml), and filtrate evaporated to dryness. The residue was partitioned between ethyl acetate (800 ml) and 10% aqueous sodium bicarbonate (250 ml). The organic layer was separated, washed with brine (250 ml), dried (magnesium sulfate) and evaporated to give title compound (34.6 g).

MS (ESP): 192 (MH$^+$) for $C_{10}H_{10}FN_3$
NMR (DMSO-d$_6$) δ: 2.08 (s, 3H); 5.68 (s, 2H); 6.45 (overlapping m, 2H); 6.84 (d, 1H); 7.03 (overlapping m, 2H).

5-Benzyloxycarbonylamino-2-(2-methylimidazol-1-yl)fluorobenzene

5-Amino-2-(2-methylimidazol-1-yl)fluorobenzene (34.25 g, 0.179 M) was dissolved in dry dichloromethane (600 ml) under nitrogen, and cooled to −5°. Pyridine (17.7 g, 0.224 M) was added, followed by benzyl chloroformate (33.7 g, 0.197 M) over 20 minutes. The mixture was stirred and the temperature allowed to rise to ambient over 16 hours. Aqueous sodium bicarbonate (5%, 250 ml) was added, the organic layer separated, the aqueous layer re-extracted with dichloromethane (2×300 ml), and combined extracts dried (magnesium sulfate). After filtration and evaporation, the residue was recrystallised from toluene (400 ml) to give title product (54.5 g).
MS (ESP): 326 (MH$^+$) for $C_{18}H_{16}FN_3O_2$
NMR (DMSO-d$_6$) δ: 2.13 (s, 3H); 5.18 (s, 2H); 6.89 (s, 1H); 7.17 (s, 1H); 7.41 (overlapping m, 7H); 7.73 (dd, 1H); 10.21 (br, 1H).

(5R)-3-(3-Fluoro-4-(2-methylimidazol-1-yl)phenyl)-5-hydroxymethyloxazolidin-2-one 5-Benzyloxycarbonylamino-2-(2-methylimidazol-1-yl) fluorobenzene (54 g, 0.166 M) was dissolved in a mixture of dry tetrahydrofuran (600 ml) and 1,3-dimethyl-tetrahydropyrimidin-2-one (100 ml) under nitrogen, cooled to −70°, and treated with a solution of n-butyllithium (1.6M in isohexane, 114 ml), over 30 minutes. After stirring for 30 minutes at −70°, a solution of (R)-glycidylbutyrate (26.35 g, 0.183 M) in dry tetrahydrofuran (50 ml) was added over 15 minutes. Stirring was continued for 16 hours allowing the temperature to rise to ambient. The mixture was treated with aqueous sodium bicarbonate (5%, 500 ml) and ethyl acetate (800 ml), the organic layer separated, and the aqueous extracted with further ethyl acetate (3×750 ml). The combined extracts were dried (magnesium sulfate) and evaporated, and the resulting oil triturated with diethyl ether. The resulting solid was recrystallisd from isopropanol to give the title compound (21.5 g).
MS (ESP): 292 (MH$^+$) for $C_{14}H_{14}FN_3O_3$
NMR (DMSO-d$_6$) δ: 2.16 (s, 3H); 3.56 (dt, 1H); 3.69 (dt, 1H); 3.88 (dd, 1H); 4.15 (t, 1H); 4.74 (m, 1H); 5.24 (t, 1H); 6.92 (s, 1H); 7.20 (s, 1H); 7.48 (dd, 1H); 7.53 (t, 1H); 7.74 (dd, 1H).

EXAMPLE 34

(5R)-3-(4-(4-Methylimidazol-1-yl)-3-fluorophenyl)-5-tetrazol-1-yl-methyloxazolidin-2-one and (5R)-3-(4-(4-Methylimidazol-1-yl)-3-fluorophenyl)-5-tetrazol-2-ylmethyloxazolidin-2-one Sodium hydride (50% in oil, 108 mg, 2.25 mM) was stirred in N,N-dimethylformamide (3 ml) under nitrogen, and 1H-tetrazole (158 mg, 2.25 mM), dissolved in N,N-dimethylformamide (4 ml) added. After stirring for 10 minutes, (5R)-3-(4-methylimidazol-1-yl-3-fluorophenyl)-5-methanesulfonyloxymethyloxazolidin-2-one (553 mg, 1.5 mM) was added, the mixture heated to 80° for 4 hours. The mixture was diluted with aqueous sodium bicarbonate (30 ml), extracted with ethyl acetate (3×20 ml), and the extract washed with water (2×20 ml), and brine (20 ml). After drying (magnesium sulfate) and evaporation, the residue was purified by chromatography on a 20 g silica Mega Bond Elut® column, eluting with a gradient increasing in polarity from 0 to 20% methanol in dichloromethane. Relevant fractions of the first eluting product were combined to give the less polar tetrazol-2-yl isomer (269 mg).
MS (ESP): 344 (MH$^+$) for $C_{15}H_{14}FN_7O_2$
NMR (DMSO-d$_6$) δ: 2.15 (s, 3H); 3.96 (dd, 1H); 4.34 (t, 1H); 5.17 (dd, 1H); 5.27 (dd, 1H); 5.33 (m, 1H); 7.21 (d, 1H); 7.37 (dd, 1H); 7.63 (t, 1H); 7.66 (dd, 1H); 7.87 (d, 1H); 9.04 (s, 1H).

The second eluting product was the 1-isomer (166 mg).
MS (ESP): 344 (MH$^+$) for $C_{15}H_{14}FN_7O_2$
NMR (DMSO-d$_6$) δ: 2.16 (s, 3H); 3.97 (dd, 1H); 4.31 (t, 1H); 4.96 (d, 2H); 5.21 (m, 1H); 7.21 (d, 1H); 7.39 (dd, 1H); 7.62 (t, 1H); 7.66 (dd, 1H); 7.87 (dd, 1H); 9.48 (s, 1H).

The intermediates for these compounds were prepared as follows:

3-Fluoro-4-(4-methylimidazol-1-yl)nitrobenzene

4-Methylimidazole (45.1 g, 0.55 M) and N,N-diisopropylethylamine (161 g, 1.25 M) were dissolved in acetonitrile (800 ml), and 3,4-difluoronitrobenzene (79.5 g, 0.5 M) added. The mixture was stirred and heated to reflux under nitrogen for 24 hours. Solvent was evaporated, the residue dissolved in ethyl acetate (800 ml), washed with water (400 ml), brine (200 ml), and dried (magnesium sulfate). The residue was dissolved in toluene (250 ml), treated with charcoal, filtered, and diluted with hot cyclohexane (75 ml) to crystallise 3-fluoro-4-(4-methylimidazol-1-yl)nitrobenzene (64.7 g).
MS (ESP): 222 (MH$^+$) for $C_{10}H_8FN_3O_2$
NMR (DMSO-d$_6$) δ: 2.18 (s, 3H); 7.29 (s, 1H); 7.92 (t, 1H); 8.07 (s, 1H); 8.18 (dd, 1H); 8.38 (dd, 1H).

5-Amino-2-(4-methylimidazol-1-yl)fluorobenzene

3-Fluoro-4-(4-methylimidazol-1-yl)nitrobenzene (64.7 g, 0.293 M) was dissolved in a mixture of methanol (200 ml) and tetrahydrofuran (800 ml), cooled to 0° under nitrogen, and treated with ammonium formate (99.3 g, 1.46 M) followed by palladium on charcoal (10%, 2.5 g). The mixture was stirred at ambient temperature for 48 hours, filtered through celite, celite washed with methanol (200 ml), and filtrate evaporated to dryness. The residue was partitioned between ethyl acetate (800 ml) and 10% aqueous sodium bicarbonate (250 ml). The organic layer was separated, washed with brine (250 ml), dried (magnesium sulfate) and evaporated to give title compound (50.6 g).
MS (ESP): 192 (MH$^+$) for $C_{10}H_{10}FN_3$
NMR (DMSO-d$_6$) δ: 2.12 (s, 3H); 5.60 (br s, 2H); 6.42 (dd, 1H); 6.47 (dd, 1H); 6.98 (s, 1H); 7.11 (t, 1H); 7.60 (s, 1H).

5-Benzyloxycarbonylamino-2-(4-methylimidazol-1-yl)fluorobenzene

5-Amino-2-(4-methylimidazol-1-yl)fluorobenzene (50.6 g, 0.265 M) was dissolved in dry dichloromethane (800 ml) under nitrogen, and cooled to −5°. Pyridine (26.1 g, 0.33 M) was added, followed by benzyl chloroformate (49.9 g, 0.292 M) over 30 minutes. The mixture was stirred and the temperature allowed to rise to ambient over 16 hours. Aqueous sodium bicarbonate (5%, 350 ml) was added, the organic layer separated, and the aqueous layer re-extracted with dichloromethane (2×200 ml), and combined organics dried (magnesium sulfate). After filtration and evaporation, the residue was recrystallised from toluene (300 ml) to give title product (80 g).

MS (ESP): 326 (MH$^+$) for $C_{18}H_{16}FN_3O_2$

NMR (DMSO-$d_6$) δ: 2.15 (s, 3H); 5.16 (s, 2H); 7.13 (s, 1H); 7.31 (dd, 1H); 7.41 (m, 5H); 7.48 (t, 1H); 7.57 (dd, 1H); 7.78 (s, 1H); 10.15 (br s, 1H).

(5R)-3-(3-Fluoro-4-(4-methylimidazol-1-yl)phenyl)-5-hydroxymethyloxazolidin-2-one 5-Benzyloxycarbonylamino-2-(4-methylimidazol-1-yl) fluorobenzene (54 g, 0.166 M) was dissolved in a mixture of dry tetrahydrofuran (600 ml) and 1,3-dimethyl-tetrahydro-pyrimidin-2-one (100 ml) under nitrogen, cooled to −70°, and treated with a solution of n-butyllithium (1.6M in isohexane, 114 ml), over 30 minutes. After stirring for 30 minutes at −70°, a solution of (R)-glycidylbutyrate (26.35 g, 0.183 M) in dry tetrahydrofuran (50 ml) was added over 15 minutes. Stirring was continued for 16 hours allowing the temperature to rise to ambient. The mixture was treated with aqueous sodium bicarbonate (5%, 500 ml) and ethyl acetate (800 ml), and undissolved solid was removed and washed well with diethyl ether to give title product (16.3 g).

The aqueous layer was further extracted with ethyl acetate (2×750 ml), the combined extracts dried (magnesium sulfate) and evaporated, and the residue triturated with diethyl ether. The resulting solid was recrystallised from ethanol to give more product (10.9 g).

MS (ESP): 292 (MH$^+$) for $C_{14}H_{14}FN_3O_3$

NMR (DMSO-$d_6$) δ: 2.13 (s, 3H); 3.56 (dd, 1H); 3.68 (dd, 1H); 3.86 (dd, 1H); 4.11 (t, 1H); 4.73 (m, 1H); 5.21 (br, 1H); 7.18 (s, 1H); 7.45 (dd, 1H); 7.60 (t, 1H); 7.73 (dd, 1H); 7.83 (s, 1H).

(5R)-3-(3-Fluoro-4-(4-methylimidazol-1-yl)phenyl)-5-methanesulfonyloxymethyloxazolidin-2-one (5R)-3-(3-Fluoro-4-(4-methylimidazol-1-yl)phenyl)-5-hydroxymethyloxazolidin-2-one (11.8 g, 40.5 mM) was stirred in a mixture of pyridine (200 ml) and triethylamine (4.86 g, 48.2 mM) under nitrogen in an ice-bath. Methanesulfonyl chloride (5.16 g, 45 mM) was added dropwise, and the mixture stirred for 2 hours, allowing the temperature to rise to ambient. Solvent was evaporated, and the residue stirred vigorously with a mixture of aqueous sodium bicarbonate (5%, 200 ml) and isohexane (200 ml). The precipitate was filtered, washed with water then isohexane, and dried. The residue was recrystallised from hot acetone (200 ml) by dilution with isohexane (300 ml) to give the title product (11.7 g), mp 151–153°.

MS (EI): 369 (M$^+$) for $C_{15}H_{16}FN_3O_5S$

NMR (DMSO-$d_6$) δ: 2.16 (s, 3H); 3.27 (s, 3H); 3.88 (dd, 1H); 4.24 (t, 1H); 4.47 (dd, 1H); 4.54 (dd, 1H); 5.04 (m, 1H); 7.20 (d, 1H); 7.45 (dd, 1H); 7.63 (t, 1H); 7.73 (dd, 1H); 7.85 (t, 1H).

EXAMPLE 35

(5R)-3-(4-(1-Benzyl-1,2,5,6-tetrahydropyridin-4-yl)-3,5-difluorophenyl)-5-(2-oxo-3H-1,3,4-oxadiazol-3-ylmethyl)oxazolidin-2-one (5R)-3-(4-(1-Benzyl-1,2,5,6-tetrahydropyridin-4-yl)-3,5-difluorophenyl)-5-hydroxy-methyloxazolidin-2-one (4.67 g, 11.6 mM), 3H-1,3,4-oxadiazol-2-one (1 g, 11.6 mM, J. Het. Chem., 1995, 32, 123), and triphenylphosphine (4.58 g, 17.5 mM) were treated with toluene (50 ml) and evaporated to dryness at 50° to remove water traces. The residue was dissolved in dry tetrahydrofuran (100 ml) by stirring under nitrogen in an ice-bath. Diisopropylazo-dicarboxylate (3.53 g, 17.5 mM) was added dropwise, and the mixture stirred 2 hours, allowing the temperature to rise to ambient. Solvent was evaporated and the residue purified by chromatography on a 90 g silica Biotage column, eluting with a gradient increasing in polarity from 0 to 100% ethyl acetate in dichloromethane. Relevant fractions were combined to give the impure product (6.2 g), contaminated with triphenylphosphine oxide. A portion (2 g) of this material was applied in dichloromethane to a 10 g Isolute strong acid SCX column, and eluted with a gradient increasing in polarity from 0 to 50% methanol in dichloromethane to remove neutral impurities, and finally with a mix of dichloromethane:methanol:concentrated aqueous ammonia 80:16:4. Solvent was evaporated from appropriate fractions, the residue taken up in 10% aqueous phosphoric acid, and reprecipitated with ammonia to give the title product (275 mg).

MS (ESP): 469 (MH$^+$) for $C_{24}H_{22}F_2N_4O_4$

NMR (DMSO-$d_6$) δ: 2.29 (br, 2H); 2.62 (t, 2H); 3.03 (m, 2H); 3.57 (s, 2H); 3.86 (dd, 1H); 4.01 (dd, 1H); 4.11 (dd, 1H); 4.18 (t, 1H); 5.00 (m, 1H); 5.78 (s, 1H); 7.27 (d, 2H); 7.33 (m, 5H); 8.45 (s, 1H).

EXAMPLE 36

(5R)-3-(4-(1-Benzyl-1,2,5,6-tetrahydropyridin-4-yl)-3,5-difluorophenyl)-5-(2-oxo-3H-1,3,4-thiadiazol-3-ylmethyl)oxazolidin-2-one Essentially the procedure of Example 35 was used, but starting with (5R)-3-(4-(1-benzyl-1,2,5,6-tetrahydropyridin-4-yl)-3,5-difluorophenyl)-5-hydroxymethyloxazolidin-2-one (800 mg, 2 mM), and 3H-1,3,4-thiadiazol-2-one (214 mg, 2.2 mM, Helv. Chim. Acta, 1982, 65, 2606), and stirring the reaction for 18 hours. After elution from the SCX column, the gum after evaporation was triturated with diethyl ether to give the desired product (291 mg).

MS (ESP): 485 (MH$^+$) for $C_{24}H_{22}F_2N_4O_3S$

NMR (DMSO-$d_6$) δ: 2.29 (br, 2H); 2.60 (t, 2H); 3.03 (m, 2H); 3.57 (s, 2H); 3.85 (dd, 1H); 4.18 (overlapping m, 2H); 4.29 (dd, 1H); 5.03 (m, 1H); 5.76 (s, 1H); 7.26 (d, 2H); 7.32 (m, 5H); 8.56 (s, 1H).

EXAMPLE 37

(5S)-3-(4-(3,6-Dihydro-2H-pyran-4-yl)-3-fluorophenyl)-5-(3-methyl-2-oxo-2,3-dihydroimidazol-1-ylmethyl)oxazolidin-2-one A solution of 1-methylimidazolidin-2-one (80 mg, 0.82 mM, Heterocycles, 1987, 26, 3153) in dimethylsulfoxide (1 ml) was treated with sodium hydride (55% in oil, 40 mg, 0.92 mM) at ambient temperature under nitrogen. After stirring for 20 minutes, (5R)-3-(4-(3,6-dihydro-2H-pyran-4-yl)-3-fluorophenyl)-5-methanesulfonyloxymethyloxazolidin-2-one (300 mg, 0.81 mM; WO 97-09328) in dimethylsulfoxide (1.5 ml) was added and stirring continued for 1.5 hours. The temperature was then progressively raised to 85°, and heated at this temperature for 24 hours. After cooling and dilution with water (50 ml), the mixture was extracted with ethyl acetate (3×30 ml), and combined extracts washed with brine (20 ml). After drying (magnesium sulfate) and evaporation, the residue was purified by chromatography on a 10 g silica Mega Bond Elut® column, eluting with a gradient increasing in polarity from 0 to 6% methanol in dichloromethane. Relevant fractions were combined to give the title product (60 mg).

MS (ESP): 374 (MH$^+$) for $C_{19}H_{20}FN_3O_4$

NMR (DMSO-d$_6$) δ: 2.41 (s, 2H); 3.08 (s, 3H); 3.76–3.95 (overlapping m, 5H); 4.15 (t, 1H); 4.20 (m, 2H); 4.92 (m, 1H); 6.08 (s, 1H); 6.50 (m, 2H); 7.25 (d, 1H); 7.40 (m, 2H).

EXAMPLE 38

(5R)-3-(4-(3,6-Dihydro-2H-pyran-4-yl)-3-fluorophenyl)-5-(3-methyl-2-thioxo-2,3-dihydroimidazol-1-ylmethyl)oxazolidin-2-one Essentially the procedure of Example 37 was used, but starting with (5R)-3-(4-(3,6-dihydro-2H-pyran-4-yl)-3-fluorophenyl)-5-methanesulfonyloxymethyloxazolidin-2-one (300 mg, 0.81 mM), and 1-methylimidazolidin-2-thione (100 mg, 0.88 mM) and heating the reaction at 60° for 1.5 hours. Chromatography on two columns gave the desired product (29 mg).

MS (ESP): 390 (MH$^+$) for $C_{19}H_{20}FN_3O_3S$

NMR (DMSO-d$_6$) δ: 2.42 (br s, 2H); 3.46 (s, 3H); 3.80 (t, 2H); 4.02 (dd, 1H); 4.20 (overlapping m, 3H); 4.27–4.47 (m, 2H); 5.09 (m, 1H); 6.09 (br s, 1H); 7.17 (m, 2H); 7.29 (dd, 1H); 7.38 (d, 1H); 7.45 (dd, 1H).

EXAMPLE 39

(5R)-3-(4-Methylthiophenyl)-5-(1,2,3-triazol-1-ylmethyl)oxazolidin-2-one (5R)-3-(4-Methylthiophenyl)-5-azidomethyloxazolidin-2-one (1.62 g, 6.14 mM) was dissolved in dioxane (30 ml), treated with norbornadiene (2.98 g, 31.5 mM) and heated under reflux for 6 hours. After removal of the solvent, the residue was dissolved in the minimum of hot ethyl acetate, filtered, cooled, then diluted with isohexane to precipitate the desired product (600 mg).

MS (CI): 291 (MH$^+$) for $C_{13}H_{14}N_4O_2S$

NMR (270 MHz, CDCl$_3$) δ: 2.46 (s, 3H); 3.92 (dd, 1H); 4.15 (t, 1H); 4.79 (m, 2H); 5.04 (m, 1H); 7.23 (d, 2H); 7.31 (d, 2H); 7.74 (d, 1H); 7.80 (d, 1H).

The starting material is described by W A Gregory et al, J. Med. Chem., 1989, 32, 1673.

EXAMPLE 40

(5R)-3-(4-Methylsulfonylphenyl)-5-(1,2,3-triazol-1-ylmethyl)oxazolidin-2-one (5R)-3-(4-Methylthiophenyl)-5-(1,2,3-triazol-1-ylmethyl)oxazolidin-2-one (500 mg, 1.72 mM) was dissolved in dichloromethane (15 ml), treated with 3-chloroperoxy-benzoic acid (50%, 1.24 g, 3.59 mM), and stirred at ambient temperature for 3 hours. After removal of the solvent, the residue was triturated with diethyl ether and filtered, to give the desired product (350 mg).

MS (CI): 323 (MH$^+$) for $C_{13}H_{14}N_4O_4S$

NMR (270 MHz, CDCl$_3$+DMSO-d$_6$) δ: 2.57 (s, 3H); 3.52 (dd, 1H); 3.78 (t, 1H); 4.36 (m, 2H); 4.67 (m, 2H); 7.18 (d, 2H); 7.26 (d, 1H); 7.38 (d, 2H); 7.47 (d, 1H).

EXAMPLE 41

(5R)-3-(4-t-Butylphenyl)-5-(1,2,3-triazol-1-ylmethyl)oxazolidin-2-one (5R)-3-(4-t-Butylphenyl)-5-azidomethyloxazolidin-2-one (400 mg, 1.46 mM) was dissolved in dioxane (8 ml), treated with norbornadiene (1.3 g, 14.1 mM) and heated under reflux for 6 hours. After removal of the solvent, the residue was dissolved ethyl acetate, and purified by flash chromatography on silica, eluting with the same solvent. Relevant fractions were combined to give the desired product (260 mg, mp 140–142°). MS (EI): 300 (M$^+$) for $C_{16}H_{20}N_4O_2$ NMR (270 MHz, CDCl$_3$) δ: 1.26 (s, 9H); 3.90 (dd, 1H); 4.15 (t, 1H); 4.77 (m, 2H); 5.03 (m, 1H); 7.30 (d, 2H); 7.36 (d, 2H); 7.72 (d, 1H); 7.79 (d, 1H).

(5R)-3-(4-t-Butylphenyl)-5-azidomethyloxazolidin-2-one may be prepared by the routes described in WA Gregory et al, J. Med. Chem., 1990, 33, 2569.

EXAMPLE 42

(5R)-3-(4-Methylsulfonylphenyl)-5-(imidazol-1-ylmethyl)oxazolidin-2-one (5S)-3-(4-Methylthiophenyl)-5-(imidazol-1-ylmethyl)oxazolidin-2-one (100 mg, 0.35 mM) was dissolved in dichloromethane (5 ml), treated with 3-chloroperoxybenzoic acid (50%, 262 mg, 0.76 mM), and stirred at ambient temperature for 3 hours. The mixture was washed with dilute aqueous sodium bicarbonate solution (10 ml), and dried (magnesium sulfate). After removal of the solvent, the residue was triturated with diethyl ether plus ethyl acetate and filtered, to give the desired product (82 mg). MS (CI): 322 (MH$^+$) for $C_{14}H_{15}N_3O_4S$ NMR (270 MHz, CDCl$_3$+DMSO-d$_6$) δ: 3.10 (s, 3H); 3.87 (dd, 1H); 4.25 (t, 1H); 4.44 (m, 2H); 5.05 (m, 1H); 6.98 (br s, 1H); 7.17 (br s, 1H); 7.67 (br s, 1H); 7.73 (d, 2H); 7.90 (d, 2H).

The intermediate for this compound was prepared as follows:

(5S)-3-(4-Methylthiophenyl)-5-(imidazol-1-ylmethyl)oxazolidin-2-one

Sodium hydride (80% in oil, 23 mg, 0.77 mM) was stirred under nitrogen in N,N-dimethylformamide (5 ml), imidazole (52 mg, 0.77 mM) added, and stirring continued for 10 minutes. (5R)-3-(4-Methylthiophenyl)-5-methanesulfonyloxymethyloxazolidin-2-one (200 mg, 0.63 mM) was dissolved in N,N-dimethylformamide (5 ml), added to the above, and the mixture stirred 18 hours at ambient temperature. After diluting with water (30 ml), the mixture was extracted with ethyl acetate (30 ml), the extract washed with brine (25 ml), dried (magnesium sulfate) and evaporated. The residue was triturated with diethyl ether, and filtered to give the desired product (129 mg, mp 129–131°).

MS (CI): 290 (MH$^+$) for $C_{14}H_{15}N_3O_2S$

NMR (270 MHz, CDCl$_3$) δ: 2.48 (s, 3H); 3.66 (dd, 1H); 4.11 (t, 1H); 4.28 (dd, 1H); 4.37 (dd, 1H); 4.91 (m, 1H); 7.11 (br s, 2H); 7.25 (d, 2H); 7.35 (d, 2H); 7.58 (br s, 1H).

(5R)-3-(4-Methylthiophenyl)-5-methanesulfonyloxymethyloxazolidin-2-one may be prepared from the corresponding 5-hydroxymethyl compound (described by W A Gregory et al, J. Med. Chem., 1989, 32, 1673) by a route analogous to that used for the methanesulfonyl intermediate of Example 1.

EXAMPLE 43

(5R)-3-(4-Methylthiophenyl)-5-(pyrazol-1-ylmethyl)oxazolidin-2-one

Sodium hydride (80% in oil, 63 mg, 2.1 mM) was stirred under nitrogen in N,N-dimethylformamide (2 ml), (5R)-3-(4-methylthiophenyl)-5-methanesulfonyloxymethyl-oxazolidin-2-one (630 mg, 2 mM) dissolved in N,N-dimethylformamide (10 ml) added, followed by pyrazole (140 mg, 2 mM) dissolved in N,N-dimethylformamide (2 ml). Stirring was continued for 1.5 hours at ambient temperature. After diluting with water (30 ml) and stirring for 1 hour, the precipitate was filtered to give the desired product (190 mg, mp 72–73°).

MS (EI): 289 (MH$^+$) for $C_{14}H_{15}N_3O_2S$

NMR (270 MHz, CDCl$_3$) δ: 2.47 (s, 3H); 3.96–4.10 (m, 2H); 4.50 (d, 2H); 4.99 (m, 1H); 6.29 (m, 1H); 7.26 (d, 2H); 7.36 (d, 2H); 7.53 (m, 2H).

EXAMPLE 44

(5R)-3-(3,5-Difluoro-4-(3,6-dihydro-1,1-dioxo-2H-thiopyran-4-yl)phenyl)-5-(1,2,3-triazol-1-ylmethyl)oxazolidin-2-one and (5R)-3-(3,5-Difluoro-4-(3,6-dihydro-1,1-dioxo-2H-thiopyran-4-yl)phenyl)-5-(1,2,3-triazol-2-ylmethyl)oxazolidin-2-one Sodium hydride (50% in oil, 72 mg, 1.5 mM) was stirred under nitrogen in N,N-dimethylformamide (3 ml), and a solution of 1,2,3-triazole (104 mg, 1.5 mM) in N,N-dimethylformamide (4 ml) added, and stirring continued for 10 minutes. (5R)-3-(3,5-Difluoro-4-(2,6-dihydro-1,1-dioxo-2H-thiopyran-4-yl)phenyl)-5-methanesulfonyl-oxymethyloxazolidin-2-one (437 mg, 1 mM) was added as solid, and the reaction heated at 75° for 1.5 hours. The mixture was diluted with aqueous 5% sodium bicarbonate (25 ml), extracted into ethyl acetate (2×20 ml), washed with water and brine (20 ml of each), dried (magnesium sulfate) and evaporated. The residue was purified by chromatography on a 10 g silica Mega Bond Elut® column, eluting with a gradient increasing in polarity from 0 to 100% ethyl acetate in dichloromethane. Relevant fractions were combined to give the 2-triazole as the less polar product (250 mg) and the 1-triazole as the more polar product (100 mg).

2-Triazole:

MS (ESP): 411 (MH$^+$) for $C_{17}H_{16}F_2N_4O_4S$

NMR (DMSO-d$_6$) δ: 2.82 (m, 2H); 3.32 (m overlapped by H$_2$O, ~2H); 3.90 (dd overlapped by m, 3H); 4.23 (t, 1H); 4.86 (m, 2H); 5.22 (m, 1H); 5.74 (t, 1H); 7.28 (d, 2H); 7.83 (s, 2H).

1-Triazole:

MS (ESP): 411 (MH$^+$) for $C_{17}H_{16}F_2N_4O_4S$

NMR (DMSO-d$_6$) δ: 2.82 (m, 2H); 3.32 (m overlapped by H$_2$O, 2H); 3.90 (dd overlapped by m, 3H); 4.21 (t, 1H); 4.82 (m, 2H); 5.16 (m, 1H); 5.75 (t, 1H); 7.30 (d, 2H); 7.87 (d, 1H); 8.18 (d, 1H).

The intermediates for this compound were prepared as follows:

4-(4-Amino-2,6-difluoro-phenyl)-tetrahydro-thiopyran-4-ol 3,5-Difluoroaniline (12.9 g, 0.1 M) in dry tetrahydrofuran (400 ml) was stirred and cooled under nitrogen to –78°. n-Butyllithium (1.6M in hexanes, 131 ml, 0.21 M) was run in slowly over 15 minutes, maintaining the temperature below –65°. Stirring was continued at the same temperature for 30 minutes, then trimethylsilyl chloride (22.8 g, 0.21 M) in tetrahydrofuran (100 ml) was added dropwise over 15 minutes. The temperature was then allowed to rise to ambient, and the mixture stirred overnight. After recooling to –78°, further n-butyllithium (1.6M in hexanes, 68.8 ml, 0.11 M) was added dropwise below –70°, and stirring continued for 5 hours to form anion. A solution of tetrahydrothiopyran-4-one (12.5 g, 0.107 M) in tetrahydrofuran (80 ml) was added dropwise, keeping the temperature below –70°, and the temperature allowed to warm to ambient overnight. The mixture was cooled in an ice-bath and acidified to pH<1 by slow addition of hydrochloric acid (1M, ~500 ml). After stirring 15 minutes, diethyl ether (1 L) was added, and the phases separated. The organic layer was washed with hydrochloric acid (1M, 200 ml), and the combined aqueous layers made basic with concentrated ammonia solution, then extracted with diethyl ether (600 ml). The extract was washed with water (100 ml), brine (100 ml), dried (magnesium sulfate) and evaporated. After dissolving the residue in dichloromethane, the desired product was precipitated by the addition of isohexane (17.4 g). MS (Negative ES): 244 (M—H—) for $C_{11}H_{13}F_2NOS$ NMR (CDCl$_3$) δ: 2.27 (d, 2H); 2.40 (t, 4H); 2.65 (t, 1H); 3.27 (t, 2H); 3.82 (br s, 2H); 6.17 (d, 2H).

4-(4-Amino-2,6-difluorophenyl)-5,6-dihydro-2H-thiopyran 4-(4-Amino-2,6-difluoro-phenyl)-tetrahydro-thiopyran-4-ol (16.7 g, 68 mM) was suspended in a mixture of concentrated hydrochloric acid (200 ml), water (50 ml) and acetic acid (200 ml), BHT (50 mg) added, and the whole stirred under nitrogen at 800 for 18 hours. After cooling, the mixture was made basic by cautious addition of concentrated ammonia, and ice-water. The mixture was then extracted with diethyl ether (2×300 ml), the extracts washed with water (100 ml), brine (200 ml) and dried (magnesium sulfate). Evaporation gave the desired product as a cream solid (15.2 g).

MS (ESP): 244 (MH$^+$) for $C_{11}H_{11}F_2NS$

NMR (CDCl$_3$) δ: 2.48 (m, 2H); 2.82 (t, 2H); 3.30 (m, 2H); 3.80 (br s, 2H); 5.87 (s, 1H); 6.17 (d, 2H).

4-(4-Benzyloxycarbonylamino-2,6-difluorophenyl)-5,6-dihydro-2H-thiopyran 4-(4-Amino-2,6-difluorophenyl)-5,6-dihydro-2H-thiopyran (15.0 g, 66 mM) was dissolved in dry dichloromethane (250 ml), pyridine (9.45 g, 113 mM) added, and the whole stirred under nitrogen at –20°. Benzyl chloroformate (17.1 g, 100 mM) in dry dichloromethane (25 ml) was added dropwise, and the mixture allowed to warm to ambient over 18 hours. The mixture was washed with hydrochloric acid (1M, 2×200 ml), then brine (200 ml) and dried (magnesium sulfate). Evaporation to a small volume and dilution with isohexane gave the desired product as a white solid (22.5 g).

MS (ESP): 362 (MH$^+$) for $C_{19}H_{17}F_2NO_2S$

NMR (DMSO-d$_6$) δ: 2.38 (m, 2H); 2.78 (t, 2H); 3.24 (m, 2H); 5.15 (s, 2H); 5.89 (s, 1H); 7.17 (d, 2H); 7.38 (m, 5H); 10.18 (s, 1H).

(5R)-3-(3,5-Difluoro-4-(2,6-dihydro-2H-thiopyran-4-yl)phenyl-5-hydroxymethyloxazolidin-2-one 4-(4-Benzyloxycarbonylamino-2,6-difluorophenyl)-5,6-dihydro-2H-thiopyran (22 g, 61 mM) was dissolved in dry tetrahydrofuran (235 ml), stirred under nitrogen, and cooled to –78°. n-Butyllithium (1.6M in hexanes, 38.2 ml, 0.61 mM) was run in slowly over 20 minutes, maintaining the temperature below −65°. Stirring was continued at the same temperature for 10 minutes, then (R)-glycidyl butyrate (8.8 g, 61 mM) in tetrahydrofuran (15 ml) was added dropwise over 10 minutes, maintaining the temperature below −60°. The temperature was then allowed to rise to ambient, and the mixture stirred overnight. Methanol (25 ml) was added, and stirring continued for 10 minute, before the addition of aqueous sodium bicarbonate (5%, 200 ml) and extraction with ethyl acetate (400 ml). After washing with sodium bicarbonate (5%, 100 ml), then brine (100 ml) and drying (magnesium sulfate), the solution was evaporated, the residue redissolved in dichloromethane, and product precipitated with isohexane. Recrystallisation from isopropanol gave the desired product (16.2 g).

MS (ESP): 328 (MH$^+$) for $C_{15}H_{15}F_2NO_3S$

NMR (DMSO-d$_6$) δ: 2.39 (m, 2H); 2.80 (t, 2H); 3.27 (m, 2H); 3.53 (m, 1H); 3.66 (m, 1H); 3.81 (dd, 1H); 4.07 (t, 1H); 4.69 (m, 1H); 5.21 (t, 1H); 5.93 (s, 1H); 7.33 (d, 2H).

(5R)-3-(3,5-Difluoro-4-(2,6-dihydro-1,1-dioxo-2H-thiopyran-4-yl)phenyl)-5-hydroxymethyl-oxazolidin-2-one (5R)-3-(3,5-Difluoro-4-(2,6-dihydro-2H-thiopyran-4-yl)phenyl)-5-hydroxymethyloxazolidin-2-one (6.54 g, 20 mM) was dissolved in dichloromethane (250 ml), and stirred at ambient temperature. 3-Chloroperoxy-benzoic acid (80%, 10 g, 46 mM) dissolved in dichloromethane (90 ml) was added dropwise, and stirring continued for 1 hour. Excess aqueous sodium metabisulfite was added, and stirring continued for 10 minutes. Excess dichloromethane (~1.5 L) was added to dissolve all organics, and the organic phase separated. After washing with aqueous sodium bicarbonate (200 ml) and drying (magnesium sulfate), the filtrate was evaporated to a small volume, and the desired product filtered (6.5 g).

MS (ESP): 360 (MH$^+$) for $C_{15}H_{15}F_2NO_5S$

NMR (DMSO-d$_6$) δ: 2.82 (m, 2H); 3.34 (m overlapped by H$_2$O, 2H); 3.52 (m, 1H); 3.67 (m, 1H); 3.83 (dd, 1H); 3.91 (m, 2H); 4.08 (t, 1H); 4.82 (m, 1H); 5.22 (t, 1H); 5.83 (t, 1H); 7.38 (d, 2H).

(5R)-3-(3,5-Difluoro-4-(2,6-dihydro-1,1-dioxo-2H-thiopyran-4-yl)phenyl)-5-methane-sulfonyloxymethyloxazolidin-2-one (5R)-3-(3,5-Difluoro-4-(2,6-dihydro-1,1-dioxo-2H-thiopyran-4-yl)phenyl)-5-hydroxymethyl-oxazolidin-2-one (6.1 g, 17 mM) was dissolved in dry tetrahydrofuran (400 ml), and stirred under nitrogen in an ice-bath. Triethylamine (2.4 g, 23.7 mM) was added, followed by dropwise addition of methanesulfonyl chloride (2.33 g, 20.3 mM). After stirring for 2 hours at 0°, the mixture was diluted with aqueous sodium bicarbonate (400 ml) and tetrahydrofuran evaporated from the mixture. The residue was extracted with dichloromethane (2×500 ml), the extract dried (magnesium sulfate). After evaporation of the filtrate to a small volume, it was diluted with isohexane to precipitate the desired product filtered (8.0 g).

MS (ESP): 438 (MH$^+$) for $C_{16}H_{17}F_2NO_7S_2$

NMR (DMSO-d$_6$) δ: 2.82 (m, 2H); 3.25 (s, 3H); 3.33 (m overlapped by H$_2$O, ~2H); 3.84 (dd, 1H); 3.93 (m, 2H); 4.19 (t, 1H); 4.48 (m, 2H); 5.03 (m, 1H); 5.85 (s, 1H); 7.38 (d, 2H).

EXAMPLE 45

(5R)-3-(4-(1-Benzyl-1,2,5,6-tetrahydropyridin-4-yl)-3-fluorophenyl)-5-(1,2,3-triazol-1-ylmethyl)oxazolidin-2-one (5R)-3-(4-(1-Benzyl-1,2,5,6-tetrahydropyridin-4-yl)-3-fluorophenyl)-5-azidomethyl-oxazolidin-2-one (4.55 g, 11.2 mM) and norbornadiene (5.15 g, 56 mM) were dissolved in dioxan (50 ml) and heated under reflux for 4 hours. The reaction mixture was evaporated and the product isolated by MPLC on silica, eluting with 5% methanol in dichloromethane. Relevant fractions were combined and evaporated to give the desired product as a gum which crystallised on trituration with diethyl ether (2.9 g).

MS (ESP): 434 (MH$^+$) for $C_{24}H_{24}FN_5O_2$

NMR (DMSO-d$_6$) δ: 2.43 (s, 2H); 2.63 (t, 2H); 3.04 (d, 2H); 3.69 (s, 2H); 3.89 (dd, 1H); 4.24 (t, 1H); 4.84 (d, 2H); 5.14 (m, 1H); 5.98 (s, 1H); 7.32 (m, 8H); 7.75 (s, 1H); 8.15 (s, 1H).

The intermediates for this compound were prepared as follows:

(5R)-3-(4-(1-Benzyl-1,2,5,6-tetrahydropyridin-4-yl)-3-fluorophenyl)-5-methanesulfonyl-oxymethyloxazolidin-2-one (5R)-3-(4-(1-Benzyl-1,2,5,6-tetrahydropyridin-4-yl)-3-fluorophenyl)-5-hydroxymethyl-oxazolidin-2-one (4.97 g, 13 mM; WO 97-30995) was reacted by essentially the technique of the related intermediate of Example 1, to give the desired product without chromatography after trituration with diethyl ether (5.78 g).

MS (ESP): 461 (MH$^+$) for $C_{23}H_{25}FN_2O_5S$

NMR (DMSO-d$_6$)δ: 2.43 (s, 2H); 2.62 (t, 2H); 3.03 (d, 2H); 3.25 (s, 3H); 3.58 (s, 2H); 3.84 (dd, 1H); 4.18 (t, 1H); 4.47 (m, 2H); 5.02 (m, 1H); 5.98 (s, 1H); 7.32 (m, 8H).

(5R)-3-(4-(1-Benzyl-1,2,5,6-tetrahydropyridin-4-yl)-3-fluorophenyl)-5-azidomethyl-oxazolidin-2-one (5R)-3-(4-(1-Benzyl-1,2,5,6-tetrahydropyridin-4-yl)-3-fluorophenyl)-5-methanesulfonyl-oxymethyloxazolidin-2-one (5.61 g, 12.2 mM) was reacted by essentially the technique of the related intermediate of Example 1, except that dimethylsulfoxide was used as solvent, to give the desired product (4.66 g).

MS (ESP): 408 (MH$^+$) for $C_{22}H_{22}FN_5O_2$

NMR (DMSO-d$_6$) δ: 2.45 (s, 2H); 2.62 (t, 2H); 3.05 (d, 2H); 3.56 (s, 2H); 3.71 (m, 3H); 4.15 (t, 1H); 4.88 (m, 1H); 5.95 (s, 1H); 7.31 (m, 8H).

EXAMPLE 46

(5R)-3-(4-(1,2,5,6-tetrahydropyridin-4-yl)-3-fluorophenyl)-5-(1,2,3-triazol-1-ylmethyl)oxazolidin-2-one (5R)-3-(4-(1-Benzyl-1,2,5,6-tetrahydropyridin-4-yl)-3-fluorophenyl)-5-(1,2,3-triazol-1-ylmethyl)oxazolidin-2-one (2.75 g, 6.35 mM) and N,N-diisopropylethylamine (165 mg, 1.27 mM) in dichloromethane (30 ml) at 0–4° under nitrogen were treated dropwise with 1-chloroethyl chloroformate (1.09 g, 7.62 mM). The solution was stirred for 30 minutes, then evaporated. The residue was purified by MPLC on silica, eluting with a gradient from 0–20% acetonitrile in ethyl acetate, to give the intermediate carbamate as a crystalline solid. This was heated under reflux in methanol (50 ml) for 20 minutes. Evaporation of the solvent and trituration with ethyl acetate gave the desired product as its hydrochloride salt (1.94 g).

MS (ESP): 344 (MH$^+$) for $C_{17}H_{18}FN_5O_2$

NMR (DMSO-d$_6$) δ: 2.63 (s, 2H); 3.24 (2d, 2H); 3.72 (d, 2H); 3.92 (m, 1H); 4.23 (t, 1H); 4.83 (d, 2H); 5.15 (m, 1H); 6.03 (s, 1H); 7.29 (dd, 1H); 7.42 (m, 2H); 7.76 (s, 1H); 8.17 (s, 1H); 9.24 (s, 2H); +1H for HCl salt.

EXAMPLE 47

(5R)-3-(4-(1-Formyl-1,2,5,6-tetrahydropyridin-4-yl)-3-fluorophenyl)-5-(1,2,3-triazol-1-ylmethyl)oxazolidin-2-one (5R)-3-(4-(1,2,5,6-Tetrahydropyridin-4-yl)-3-fluorophenyl)-5-(1,2,3-triazol-1-ylmethyl)-oxazolidin-2-one hydrochloride (450 mg, 1.19 mM) and triethylamine (156 mg, 1.56 mM) were heated under reflux for 48 hours in ethyl formate (20 ml). The reaction mixture was diluted with ethyl acetate (30 ml) and washed with water and brine. Drying (sodium sulfate) and evaporation gave a gum which crystallised on trituration with diethyl ether to give the desired product (358 mg).

MS (ESP): 372 (MH$^+$) for $C_{18}H_{18}FN_5O_3$

NMR (DMSO-d$_6$) δ: 2.38 (br, 2H); 3.59 (m, 2H); 3.91 (dd, 1H); 4.06 (dd, 2H); 4.22 (t, 1H); 4.83 (d, 2H); 5.13 (m, 1H); 6.00 (2×s, 1H); 7.23 (dd, 1H); 7.38 (m, 2H); 7.75 (s, 1H); 8.14 (2×s, 1H); 8.17 (s, 1H).

EXAMPLE 48

(5R)-3-(4-(1-Benzyl-1,2,5,6-tetrahydropyridin-4-yl)-3,5-difluorophenyl)-5-(1,2,3-triazol-1-ylmethyl)oxazolidin-2-one (5R)-3-(4-(1-Benzyl-1,2,5,6-tetrahydropyridin-4-yl)-3,5-difluorophenyl)-5-azidomethyl-oxazolidin-2-one (850 mg, 2 mM) was reacted by essentially the technique of Example 45, to give the desired product (550 mg).

MS (ESP): 452 (MH$^+$) for $C_{24}H_{23}F_2N_5O_2$

NMR (DMSO-d$_6$) δ: 2.29 (s, 2H); 2.61 (t, 2H); 3.05 (s, 2H); 3.59 (s, 2H); 3.88 (dd, 1H); 4.21 (t, 1H); 4.80 (d, 2H); 5.15 (m, 1H); 5.78 (s, 1H); 7.29 (m, 7H); 7.75 (s, 1H); 8.15 (s, 1H).

The intermediates for this compound were prepared as follows:

(5R)-3-(4-(1-Benzyl-1,2,5,6-tetrahydropyridin-4-yl)-3,5-difluorophenyl)-5-methanesulfonyl-oxymethyloxazolidin-2-one (5R)-3-(4-(1-Benzyl-1,2,5,6-tetrahydropyridin-4-yl)-3,5-di fluorophenyl)-5-hydroxymethyl-oxazolidin-2-one (WO 99-64417; 8.4 g, 21 mM) was reacted by essentially the technique of the related intermediate of Example 1, to give the desired product without chromatography after trituration with diethyl ether (9.38 g).

NMR (DMSO-d$_6$) δ: 2.30 (s, 2H); 2.62 (t, 2H); 3.05 (d, 2H); 3.24 (s, 3H); 3.58 (s, 2H); 3.82 (dd, 1H); 4.17 (t, 1H); 4.46 (m, 2H); 5.02 (br s, 1H); 5.78 (s, 1H); 7.30 (m, 7H).

(5R)-3-(4-(1-Benzyl-1,2,5,6-tetrahydropyridin-4-yl)-3,5-difluorophenyl)-5-azidomethyl-oxazolidin-2-one (5R)-3-(4-(1-Benzyl-1,2,5,6-tetrahydropyridin-4-yl)-3,5-difluorophenyl)-5-methanesulfonyl-oxymethyloxazolidin-2-one (4.06 g, 8.5 mM) was reacted by essentially the technique of the related intermediate of Example 1, except that dimethylsulfoxide was used as solvent. After work-up, the residue was purified by MPLC on silica, eluting with 50% isohexane in ethyl acetate, to give the desired product as a gum which crystallised on trituration with ethyl acetate and isohexane (2.84 g).

MS (ESP): 408 (MH$^+$) for $C_{22}H_{21}F_2N_5O_2$

NMR (DMSO-d$_6$) δ: 2.31 (s, 2H); 2.62 (t, 2H); 3.05 (d, 2H); 3.60 (s, 2H); 3.75 (m, 3H); 4.12 (t, 1H); 4.90 (m, 1H); 5.88 (s, 1H); 7.30 (m, 7H).

EXAMPLE 49

(5R)-3-(4-(1,2,5,6-tetrahydropyridin-4-yl)-3,5-difluorophenyl)-5-(1,2,3-triazol-1-ylmethyl)oxazolidin-2-one (5R)-3-(4-(1-Benzyl-1,2,5,6-tetrahydropyridin-4-yl)-3-fluorophenyl)-5-(1,2,3-triazol-1-ylmethyl)oxazolidin-2-one (1.13 g, 2.5 mM) was reacted by essentially the technique of Example 46, to give the desired product as its hydrochloride salt (665 mg).

MS (ESP): 362 (MH$^+$) for $C_{17}H_{17}F_2N_5O_2$

NMR (DMSO-d$_6$) δ: 2.55 (overlapping DMSO, ~2H); 3.29 (overlapping H$_2$O, ~2H); 3.79 (d, 2H); 3.90 (dd, 1H); 4.23 (t, 1H); 4.82 (d, 2H); 5.19 (m, 1H); 5.90 (s, 1H); 7.31 (d, 2H); 7.76 (s, 1H); 8.18 (s, 1H); 9.25 (s, 2H); +1H for HCl salt.

EXAMPLE 50

(5R)-3-(4-(1-Formyl-1,2,5,6-tetrahydropyridin-4-yl)-3,5-difluorophenyl)-5-(1,2,3-triazol-1-ylmethyl)oxazolidin-2-one (5R)-3-(4-(1,2,5,6-Tetrahydropyridin-4-yl)-3,5-difluorophenyl)-5-(1,2,3-triazol-1-ylmethyl)-oxazolidin-2-one hydrochloride (450 mg, 1.13 mM) was reacted by essentially the technique of Example 47, to give the desired product (387 mg).

MS (ESP): 390 (MH$^+$) for $C_{18}H_{17}F_2N_5O_3$

NMR (DMSO-d$_6$) δ: 2.33 (2×s, 2H); 3.60 (m, 2H); 3.90 (dd, 1H); 4.05 (2×d, 2H); 4.23 (t, 1H); 4.82 (d, 2H); 5.18 (m, 1H); 5.90 (2×s, 1H); 7.28 (d, 2H); 7.75 (s, 1H); 8.13 (2×s, 1H); 8.16 (2×s, 1H).

EXAMPLE 51

(5R)-3-(4-(1-(2-Acetoxyacetyl)-1,2,5,6-tetrahydropyridin-4-yl)-3,5-difluorophenyl)-5-(1,2,3-triazol-1-ylmethyl)oxazolidin-2-one A solution of (5R)-3-(4-(1,2,5,6-tetrahydropyridin-4-yl)-3,5-difluorophenyl)-5-(1,2,3-triazol-1-ylmethyl)oxazolidin-2-one hydrochloride (650 mg, 1.64 mM) in acetone (20 ml) and water (10 ml), was treated with sodium bicarbonate (1.38 g, 16.4 mM) and the mixture cooled to 0–4°. Acetoxyacetyl chloride (448 mg, 3.28 mM) was added dropwise and the reaction mixture stirred at 0–4° for 20 minutes before allowing to warm to ambient temperature. After dilution with water the mixture was extracted well with ethyl acetate. The organic phase was separated, dried (sodium sulfate), solvent evaporated, and the residue triturated with diethyl ether to give the desired product (702 mg).

MS (ESP): 462 (MH$^+$) for $C_{21}H_{21}F_2N_5O_5$

NMR (DMSO-d$_6$) δ: 2.09 (s, 3H); 2.36 (2×s, 2H); 3.60 (m, 2H); 3.89 (dd, 1H); 4.09 (br, 2H); 4.23 (t, 1H); 4.83 (m, 4H); 5.18 (m, 1H); 5.89 (s, 1H); 7.29 (d, 2H); 7.78 (s, 1H); 8.20 (s, 1H).

EXAMPLE 52

((5R)-3-(4-(1-(2-Hydroxyacetyl)-1,2,5,6-tetrahydropyridin-4-yl)-3,5-difluorophenyl)-5-(1,2,3-triazol-1-ylmethyl)oxazolidin-2-one (5R)-3-(4-(1-(2-Acetoxyacetyl)-1,2,5,6-tetrahydropyridin-4-yl)-3,5-difluorophenyl)-5-(1,2,3-triazol-1-ylmethyl)oxazolidin-2-one (430 mg, 0.93 mM) was stirred at ambient temperature with saturated methanolic ammonia (10 ml) for 18 hours. The initial suspension gave a solution from which the product crystallised. The reaction mixture was diluted with diethyl ether and the product filtered off and washed with diethyl ether (337 mg).

MS (ESP): 420 (MH$^+$) for $C_{19}H_{19}F_2N_5O_4$

NMR (DMSO-d$_6$) δ: 2.32 (2×s, 2H); 3.54 (br, 1H); 3.68 (br, 1H); 3.99 (dd, 1H); 4.10 (m, 4H); 4.24 (t, 1H); 4.58 (m, 1H); 4.82 (d, 2H); 5.18 (m, 1H); 5.88 (br, 1H); 7.28 (d, 2H); 7.77 (s, 1H); 8.17 (s, 1H).

EXAMPLE 53

(5R)-3-(4-(1-((4S)-2,2-dimethyl-1,3-dioxolane-4-carbonyl)-1,2,5,6-tetrahydropyridin-4-yl)-3,5-difluorophenyl)-5-(1,2,3-triazol-1-ylmethyl)oxazolidin-2-one A solution of (5R)-3-(4-(1,2,5,6-tetrahydropyridin-4-yl)-3,5-difluorophenyl)-5-(1,2,3-triazol-1-ylmethyl)oxazolidin-2-one hydrochloride (650 mg, 1.64 mM) in dry dichloromethane (20 ml) at 0–4°, was treated with pyridine (648 mg, 8.2 mM) followed by dropwise addition of (4S)-2,2-dimethyl-1,3-dioxolane-4-carbonyl chloride (430 mg, 2.64 mM). The solution was allowed to warm to ambient temperature and stir for 1 hour. The reaction mixture was washed with water and brine, dried (sodium sulfate) and evaporated to a gum which crystallised readily on trituration with diethyl ether to give the title compound (788 mg).

MS (ESP): 490 (MH$^+$) for $C_{23}H_{25}F_2N_5O_5$

NMR (DMSO-d$_6$) δ: 1.32 (d, 6H); 2.34 (2×s, 2H); 3.87 (dd, 1H); 4.09 (t, 1H); 4.20 (t, 2H); 3.00–4.30 (m, 4H); 4.80 (d, 2H); 4.90 (m, 1H); 5.15 (m, 1H); 5.89 (s, 1H); 7.25 (d, 2H); 7.75 (s, 1H); 8.17 (s, 1H).

EXAMPLE 54

(5R)-3-(4-(1-((2S)-2,3-Dihydroxypropionyl)-1,2,5,6-tetrahydropyridin-4-yl)-3,5-difluorophenyl)-5-(1,2,3-triazol-1-ylmethyl)oxazolidin-2-one To a stirred solution of (5R)-3-(4-(1-((4S)-2,2-dimethyl-1,3-dioxolane-4-carbonyl)-1,2,5,6-tetrahydropyridin-4-yl)-3,5-difluorophenyl)-5-(1,2,3-triazol-1-ylmethyl)oxazolidin-2-one (700 mg, 1.43 mM) in tetrahydrofuran (25 ml) was added aqueous hydrochloric acid (1M, 15 ml) and the mixture stirred at ambient temperature for 2 days. Solvent was evaporated and the residue treated with water (10 ml). Aqueous sodium acetate (10%, 10 ml) was added, and the precipitate filtered and washed with ethanol and diethyl ether to give the title compound (514 mg).

MS (ESP): 450 (MH$^+$) for $C_{20}H_{21}F_2N_5O_5$

NMR (DMSO-d$_6$) δ: 2.33 (m, 2H); 3.51 (m, 3H); 3.71 (br, 2H); 3.90 (dd, 1H); 4.00–4.40 (complex, 3H); 4.67 (m, 1H); 4.82 (d, 2H); 4.92 (m, 1H); 5.15 (m, 1H); 5.87 (s, 1H); 7.27 (d, 2H); 7.76 (s, 1H); 8.17 (s, 1H).

EXAMPLE 55

(5R)-3-(4-(1-(2-Acetoxyacetyl)-1,2,5,6-tetrahydropyridin-4-yl)-3-fluoro-phenyl)-5-(1,2,3-triazol-1-ylmethyl)oxazolidin-2-one (5R)-3-(4-(1,2,5,6-Tetrahydropyridin-4-yl)-3-fluorophenyl)-5-(1,2,3-triazol-1-ylmethyl)-oxazolidin-2-one hydrochloride (803 mg, 2.11 mM) was reacted by essentially the technique of Example 51, to give the desired product (767 mg).

MS (ESP): 444 (MH$^+$) for $C_{21}H_{22}FN_5O_5$

NMR (DMSO-d$_6$) δ: 2.00 (s, 3H); 2.41 (s, 2H); 3.59 (m, 2H); 3.90 (dd, 1H); 4.09 (s, 2H); 4.25 (t, 1H); 4.83 (m, 4H); 5.15 (m, 1H); 5.98 (s, 1H); 7.25 (dd, 1H); 7.40 (m, 2H); 7.76 (s, 1H); 8.17 (s, 1H).

EXAMPLE 56

(5R)-3-(4-(1-(2-Hydroxyacetyl)-1,2,5,6-tetrahydropyridin-4-yl)-3-fluoro-phenyl)-5-(1,2,3-triazol-1-ylmethyl)oxazolidin-2-one (5R)-3-(4-(1-(2-Acetoxyacetyl)-1,2,5,6-tetrahydropyridin-4-yl)-3-fluorophenyl)-5-(1,2,3-triazol-1-ylmethyl)oxazolidin-2-one (443 mg, 1 mM) was reacted by essentially the technique of Example 51, to give the desired product (370 mg).

MS (ESP): 402 (MH$^+$) for $C_{19}H_{20}FN_5O_4$

NMR (DMSO-d$_6$) δ: 2.45 (s, 2H); 3.60 (m, 2H); 3.89 (dd, 1H); 4.12 (m, 4H); 4.25 (t, 1H); 4.55 (m, 1H); 4.82 (d, 2H); 5.15 (m, 1H); 6.00 (d, 1H); 7.25 (dd, 1H); 7.40 (m, 2H); 7.75 (s, 1H); 8.16 (s, 1H).

EXAMPLE 57

(5R)-3-(4-(1-((4S)-2,2-dimethyl-1,3-dioxolane-4-carbonyl)-1,2,5,6-tetrahydropyridin-4-yl)-3-fluorophenyl)-5-(1,2,3-triazol-1-ylmethyl)oxazolidin-2-one (5R)-3-(4-(1,2,5,6-Tetrahydropyridin-4-yl)-3-fluorophenyl)-5-(1,2,3-triazol-1-ylmethyl)-oxazolidin-2-one hydrochloride (651 mg, 1.71 mM) was reacted by essentially the technique of Example 53, to give the desired product (697 mg).

MS (ESP): 472 (MH$^+$) for $C_{23}H_{26}FN_5O_5$

NMR (DMSO-d$_6$) δ: 1.31 (m, 6H); 2.40 (s, 2H); 3.60–4.30 (complex, 8H); 4.83 (d, 2H); 4.90 (m, 1H); 5.15 (m, 1H); 6.00 (s, 1H); 7.15 (dd, 1H); 7.40 (m, 2H); 7.73 (s, 1H); 8.15 (s, 1H).

EXAMPLE 58

(5R)-3-(4-(1-((2S)-2,3-Dihydroxypropionyl)-1,2,5,6-tetrahydropyridin-4-yl)-3-fluorophenyl)-5-(1,2,3-triazol-1-ylmethyl)oxazolidin-2-one (5R)-3-(4-(1-((4S)-2,2-Dimethyl-1,3-dioxolane-4-carbonyl)-1,2,5,6-tetrahydropyridin-4-yl)-3-fluorophenyl)-5-(1,2,3-triazol-1-ylmethyl)oxazolidin-2-one (600 mg, 1.27 mM)

was reacted by essentially the technique of Example 54, to give the desired product (443 mg).

MS (ESP): 432 (MH$^+$) for $C_{20}H_{22}FN_5O_5$

NMR (DMSO-d$_6$) δ: 2.40 (br, 2H); 3.35–3.85 (complex, 4H); 3.90 (dd, 1H); 4.10 (s, 1H); 4.25 (t, 2H); 4.35 (m, 1H); 4.65 (m, 1H); 4.82 (d, 2H); 4.93 (m, 1H); 5.13 (m, 1H); 6.00 (s, 1H); 7.22 (dd, 1H); 7.38 (m, 2H); 7.73 (s, 1H); 8.15 (s, 1H)

EXAMPLE 59

(5R)-3-(4-(1-Benzyl-1,2,5,6-tetrahydropyridin-4-yl)-3,5-difluorophenyl)-5-(1,2,3-triazol-2-ylmethyl)oxazolidin-2-one (5R)-3-(4-(1-Benzyl-1,2,5,6-tetrahydropyridin-4-yl)-3,5-difluorophenyl)-5-methanesulfonyl-oxymethyloxazolidin-2-one (2.39 g, 5.0 mM) was dissolved in N,N-dimethylformamide (25 ml), and treated with 1,2,3-triazole (690 mg, 10 mM) and anhydrous potassium carbonate (1.38 g, 10 mM), then stirred at 80° for 3 hours. The reaction mixture was diluted with water and extracted with ethyl acetate. The organic phase was washed with water, brine, dried (magnesium sulfate) and evaporated to a gum, which was purified by MPLC on silica, eluting with a gradient from 10 to 100% ethyl acetate in isohexane. Combination of appropriate fractions gave two products as gums which crystallised on trituration with diethyl ether. The less polar product was identified as the desired product (1.45 g).

MS (ESP): 452 (MH$^+$) for $C_{24}H_{23}F_2N_5O_2$

NMR (DMSO-d$_6$) δ: 2.31(s, 2H); 2.62 (t, 2H); 3.05 (d, 2H); 3.59 (s, 2H); 3.89 (dd, 1H); 4.21 (t, 1H); 4.83 (m, 2H); 5.21 (m, 1H); 5.78 (s, 1H); 7.27 (m, 7H); 7.82 (s, 2H).

The more polar product (760 mg) was identified as the 1-substituted triazole isomer of Example 48.

EXAMPLE 60

(5R)-3-(4-(1-Benzyl-1,2,5,6-tetrahydropyridin-4-yl)-3,5-difluorophenyl)-5-(1,2,4-triazol-1-ylmethyl)oxazolidin-2-one (5R)-3-(4-(1-Benzyl-1,2,5,6-tetrahydropyridin-4-yl)-3,5-difluorophenyl)-5-methanesulfonyl-oxymethyloxazolidin-2-one (956 mg, 2.0 mM) was dissolved in N,N-dimethylformamide (12 ml), treated with 1,2,4-triazole (173 mg, 2.5 mM) and anhydrous potassium carbonate (690 mg, 5.0 mM) and stirred at 80° for 18 hours. The reaction mixture was diluted with water and extracted with ethyl acetate. The organic phase was washed with water, brine, dried (magnesium sulfate) and evaporated to a gum which was purified by MPLC on silica eluting with a gradient from 0 to 20% acetonitrile in ethyl acetate. Evaporation of appropriate fractions gave the title compound (719 mg) after trituration with diethyl ether.

MS (ESP): 452 (MH$^+$) for $C_{24}H_{23}F_2N_5O_2$

NMR (DMSO-d$_6$) δ: 2.30 (s, 2H); 2.61 (s, 2H); 3.05 (d, 2H); 3.69 (s, 2H); 3.80 (dd, 1H); 4.20 (t, 1H); 4.60 (m, 2H); 5.09 (m, 1H); 5.80 (s, 1H); 7.30 (m, 7H); 6.99 (s, 1H); 8.56 (s, 1H).

EXAMPLE 61

(5R)-3-(4-(1,2,5,6-Tetrahydropyridin-4-yl)-3,5-difluorophenyl)-5-(1,2,4-triazol-1-ylmethyl)oxazolidin-2-one (5R)-3-(4-(1-Benzyl-1,2,5,6-tetrahydropyridin-4-yl)-3,5-difluorophenyl)-5-(1,2,4-triazol-1-ylmethyl)oxazolidin-2-one one (631 mg, 1.4 mM) was reacted by essentially the technique of Example 46, to give the desired product as its hydrochloride salt (401 mg).

MS (ESP): 362 (MH$^+$) for $C_{17}H_{17}F_2N_5O_2$

NMR (DMSO-d$_6$) δ: 2.55 (overlapping DMSO, 2H); 3.25 (overlapping H$_2$O, 2H); 3.73 (s, 2H); 3.9 (dd, 1H); 4.17 (t, 1H); 4.60 (t, 2H); 5.10 (m, 1H); 5.87 (s, 1H); 7.27 (d, 2H); 7.98 (s, 1H); 8.55 (s, 1H); 9.23 (s, 2H); +1H for HCl salt.

EXAMPLE 62

(5R)-3-(4-(1-((4S)-2,2-Dimethyl-1,3-dioxolane-4-carbonyl)-1,2,5,6-tetrahydropyridin-4-yl)-3,5-difluorophenyl)-5-(1,2,4-triazol-1-ylmethyl)oxazolidin-2-one (5R)-3-(4-(1,2,5,6-Tetrahydropyridin-4-yl)-3,5-difluorophenyl)-5-(1,2,4-triazol-1-ylmethyl)-oxazolidin-2-one hydrochloride (399 mg, 1.0 mM) was reacted by essentially the technique of Example 53, except that purification by MPLC on silica eluting with 5% methanol in dichloromethane was needed, to give the desired product (288 mg). MS (ESP): 490 (MH$^+$) for $C_{23}H_{25}F_2N_5O_5$ NMR (DMSO-d$_6$) δ: 1.32 (d, 6H); 2.35 (m, 2H); 3.70 (m, 2H); 3.90 (dd, 1H); 3.95–4.30 (complex, 5H); 4.60 (in, 2H); 4.88 (m, 1H); 5.10 (m, 1H); 5.85 (s, 1H); 7.25 (d, 2H); 7.98 (s, 1H); 8.55 (s, 1H).

EXAMPLE 63

(5R)-3-(4-(1-((2S)-2,3-Dihydroxypropionyl)-1,2,5,6-tetrahydropyridin-4-yl)-3,5-difluorophenyl)-5-(1,2,4-triazol-1-ylmethyl)oxazolidin-2-one (5R)-3-(4-(1-((4S)-2,2-Dimethyl-1,3-dioxolane-4-carbonyl)-1,2,5,6-tetrahydropyridin-4-yl)-3,5-difluorophenyl)-5-(1,2,4-triazol-1-ylmethyl)oxazolidin-2-one (269 mg, 0.55 mM) was reacted by essentially the technique of Example 54, to give the desired product (130 mg).

MS (ESP): 450 (MH$^+$) for $C_{20}H_{21}F_2N_5O_5$

NMR (DMSO-d$_6$) δ: 2.35 (m, 2H); 3.52 (m, 2H); 3.72 (br, 2H); 3.92 (dd, 1H); 4.00–4.45 (complex, 4H); 4.65 (m, 3H); 4.98 (m, 1H); 5.15 (m, 1H); 5.90 (s, 1H); 7.30 (d, 2H); 8.00 (s, 1H); 8.55 (s, 1H).

EXAMPLE 64

(5R)-3-(4-(1-((2R)-2-Hydroxy-3-methylthiopropionyl)-1,2,5,6-tetrahydropyridin-4-yl)-3-fluorophenyl)-5-(1,2,3-triazol-1-ylmethyl)oxazolidin-2-one (5R)-3-(4-(1,2,5,6-Tetrahydropyridin-4-yl-3-fluorophenyl)-5-(1,2,3-triazol-1-ylmethyl)-oxazolidin-2-one hydrochloride (400 mg, 1.05 mM), (2R)-2-hydroxy-3-methylthiopropionic acid (143 mg, 1.05 mM; WO 92-00276), 1-hydroxybenzotriazole (184 mg, 1.37 mM) and N,N-diisopropylethylamine (177 mg, 1.37 mM) were dissolved in dichloromethane (10 ml) and 1-(3-dimethylaminopropyl)-3-ethylcarbodiimide hydrochloride (263 mg, 1.37 mM) was added portionwise, and the mixture was stirred overnight. Solvent was removed and crude product purified by flash chromatography on silica eluting with 2% methanol in dichloromethane, to afford the title compound as a clear oil that readily crystallised (480 mg).

MS (ESP): 462 (MH$^+$) for $C_{21}H_{24}FN_5O_4S$

NMR (DMSO-d$_6$) δ: 2.10 (s, 3H); 2.43 (m, 2H); 2.61 (m, 1H); 2.78 (m, 1H); 3.65 (m, 2H); 3.90 (m, 1H); 4.17 (m, 2H);

4.24 (t, 1H); 4.50 (m, 1H); 4.84 (d, 2H); 5.15 (m, 1H); 5.44 (dd, 1H); 6.03 (s, 1H); 7.20–7.45 (m, 3H); 7.77 (s, 1H); 8.17 s, 1H).

EXAMPLE 65

(5R)-3-(4-(1-((2R)-2-Hydroxy-3-methanesulfonyl-propionyl)-1,2,5,6-tetrahydropyridin-4-yl)-3-fluorophenyl)-5-(1,2,3-triazol-1-ylmethyl)oxazolidin-2-one (5R)-3-(4-(1-((2R)-2-Hydroxy-3-methylthiopropionyl)-1,2,5,6-tetrahydropyridin-4-yl)-3-fluorophenyl)-5-(1,2,3-triazol-1-ylmethyl)oxazolidin-2-one (430 mg, 0.93 mM) was stirred in dichloromethane (15 ml) at 0°, and 3-chloroperoxybenzoic acid (70%, 456 mg, 1.87 mM) was added portionwise. The solution was stirred at 0° for 1 hour. Dichloromethane (50 ml) was added and the mixture washed with saturated aqueous sodium bicarbonate (50 ml), dried (magnesium sulfate) and evaporated. Crude product was purified by flash chromatography on silica eluting with 4% methanol in dichloromethane to give the title compound as a white solid (349 mg).

MS (ESP): 494 (MH$^+$) for $C_{21}H_{24}FN_5O_6S$

NMR (DMSO-d$_6$) δ: 2.18–4.23 (m, 8H); 3.03 (s, 3H); 3.92 (m, 1H); 4.23 (t, 1H); 4.78 (m, 1H); 4.83 (d, 2H); 5.14 (m, 1H); 6.02 (dd, 1H); 6.04 (s, 1H); 7.20–7.46 (m, 3H); 7.75 (s, 1H); 8.17 (s, 1H).

EXAMPLE 66

(5S)-3-(4-(1-Benzyl-1,2,5,6-tetrahydropyridin-4-yl)-3-fluorophenyl)-5-(2-oxo-3H-1,3-oxazol-3-ylmethyl)oxazolidin-2-one (5R)-3-(4-(1-Benzyl-1,2,5,6-tetrahydropyridin-4-yl)-3-fluorophenyl)-5-hydroxymethyl-oxazolidin-2-one (2.92 g, 7.3 mM; WO 97-30995) was stirred in tetrahydrofuran (60 ml), and 3H-oxazol-2-one (0.69 g, 8.12 mM) and tributylphosphine (1.77 g, 8.75 mM) were added. The mixture was stirred at 0° under nitrogen, and 1,1'-azodicarbonyldipiperidine (2.06 g, 8.18 mM) was added portionwise. The reaction mixture was allowed to warm to ambient temperature and stirred overnight. The precipitate was filtered off and solvent removed. The resulting oil was dissolved in dichloromethane (30 ml), stirred at 0° for 30 minutes, and further precipitate removed. The filtrate was purified by MPLC on silica eluting with a gradient from 60 to 80% ethyl acetate in isohexane, to give a mixture of starting material and product, which was rechromatographed eluting with 3% MeOH in dichloromethane to give the title compound as a white solid (30 mg).

MS (ESP): 468 (MH$^+$) for $C_{25}H_{23}F_2N_3O_4$

NMR (DMSO-d$_6$) δ: 2.28 (m, 2H); 2.62 (t, 2H); 3.04 (m, 2H); 3.57 (s, 2H); 3.78–3.95 (m, 3H); 4.17 (t, 1H); 4.96 (m, 1H); 5.78 (s, 1H); 7.07 (d, 1H) 7.19 (d, 1H); 7.21–7.35 (m, 7H).

EXAMPLE 67

(5S)-3-(4-(3,6-Dihydro-2H-pyran-4-yl)-3-fluorophenyl)-5-(2-oxo-1H-pyridin-1-ylmethyl)oxazolidin-2-one 2-Hydroxypyridine (108 mg, 1.14 mM) was added at room temperature, under an atmosphere of nitrogen, to a stirred suspension of sodium hydride (60% dispersion in oil, 48 mg, 1.2 mM) in N,N-dimethylformamide (5 ml). The reaction was stirred for 30 minutes then (5R)-3-(4-(3,6-dihydro-2H-pyran-4-yl)-3-fluorophenyl)-5-methanesulfonyloxymethyloxazolidin-2-one (400 mg, 1.08 mM; WO 97-09328) was added in one portion. The mixture was stirred and heated at 60° for 5 hour before quenching in water (20 ml) and extracting with ethyl acetate. The extract was washed twice with water and once with saturated brine, dried (magnesium sulfate) and evaporated to an orange oil, which was purified by flash chromatography on silica, eluting with 2.5% methanol in dichloromethane to give the title compound (115 mg) as a colourless solid.

MS (ESP): 371 (MH$^+$) for $C_{20}H_{19}FN_2O_4$

NMR (CDCl$_3$) δ: 2.50 (m, 2H); 3.90 (m, 3H); 4.15 (t, 1H); 4.22 (dd, 1H); 4.31 (m, 2H); 4.46 (dd, 1H); 5.17 (m, 1H); 6.06 (m, 1H); 6.25 (t, 1H); 6.60 (d, 1H); 7.14 (dd, 1H); 7.26 (t, 1H); 7.30–7.45 (m, 3H).

EXAMPLE 68

(5R)-3-(4-(3,6-Dihydro-2H-pyran-4-yl)-3-fluorophenyl)-5-(2-oxo-2H-pyridaz-1-ylmethyl)oxazolidin-2-one Diisopropylazodicarboxylate (248 mg, 1.2 mM) was added at room temperature to (5R)-3-(4-(3,6-dihydro-2H-pyran-4-yl)-3-fluorophenyl)-5-hydroxymethyloxazolidin-2-one (300 mg, 1.02 mM), 2H-pyridazin-3-one (118 mg, 1.22 mM) and triphenylphosphine (340 mg, 1.30 mM) in tetrahydrofuran (8 ml). The reaction was stirred for 30 minutes then solvent evaporated and the residue purified by flash chromatography on silica, eluting with a gradient from 0 to 10% methanol in ethyl acetate, to give the title compound as a colourless solid (219 mg).

MS (ESP): 372 (MH$^+$) for $C_{19}H_{18}FN_3O_4$

NMR (CDCl$_3$) δ: 2.50 (m, 2H); 3.90 (t, 2H); 3.96 (d, 1H); 4.12 (t, 1H); 4.32 (m, 2H); 4.50 (dd, 1H); 4.58 (dd, 1H); 5.14 (m, 1H); 6.05 (m, 1H); 6.96 (dd, 1H); 7.17–7.28 (m, 3H); 7.38 (dd, 1H); 7.81 (m, 1H).

EXAMPLE 69

(5R)-3-(4-(1-Benzyl-1,2,5,6-tetrahydropyridin-4-yl)-3-fluorophenyl)-5-(tetrazol-1-ylmethyl)oxazolidin-2-one and (5R)-3-(4-(1-Benzyl-1,2,5,6-tetrahydropyridin-4-yl)-3-fluorophenyl)-5-(tetrazol-2-ylmethyl)oxazolidin-2-one Diethylazodicarboxylate (2.28 g, 13.1 mM) was added, under an atmosphere of nitrogen, to a mixture of (5R)-3-(4-(1-benzyl-1,2,5,6-tetrahydropyridin-4-yl)-3-fluorophenyl)-5-hydroxymethyloxazolidin-2-one (5.0 g, 13.1 mM; WO 97-30995), 1H-tetrazole (0.91 g, 13.0 mM) and triphenylphosphine (3.43 g, 13.1 mM) in tetrahydrofuran (150 ml), pre-cooled in ice/water. The reaction was then allowed to warm to room temperature and stirred 18 hours. Solvent was evaporated and the resulting brown oil dissolved in dichloromethane (80 ml) and cooled in ice/water before filtering. The filtered solution was purified by MPLC on silica, eluting with ethyl acetate to give the title compounds; the 2-tetrazole isomer is the less polar, and elutes first. Each was then individually purified by strong cation ion-exchange chromatography (10 g Bond Elut®), eluting with a gradient from 0 to 5% methanol in dichloromethane, followed by 3% 880 ammonia in a 9:1 mixture of dichloromethane and methanol, to give 2-tetrazole (2.61 g) and 1-tetrazole isomers (0.44 g) as colourless solids.

2-Tetrazole:
  MS (ESP): 435 (MH$^+$) for $C_{23}H_{23}FN_6O_2$
  NMR (DMSO-d$_6$) δ: 2.42 (m, 2H); 2.60 (t, 2H), 3.05 (d, 2H), 3.58 (s, 2H); 3.91 (dd, 1H); 4.30 (t, 1H); 5.11–5.31 (m, 3H); 5.97 (m, 1H); 7.19–7.44 (m, 8H); 9.01 (s, 1H).

1-Tetrazole:
  MS (ESP): 435 (MH$^+$) for $C_{23}H_{23}FN_6O_2$
  NMR (DMSO-d$_6$) δ: 2.43 (m, 2H); 2.60 (t, 2H), 3.04 (d, 2H); 3.58 (s, 2H); 3.92 (dd, 1H); 4.25 (t, 1H); 4.93 (d, 2H); 5.17 (m, 1H); 5.97 (m, 1H); 7.19–7.44 (m, 8H); 9.48 (s, 1H).

EXAMPLE 70

(5R)-3-(4-(1,2,5,6-Tetrahydropyridin-4-yl)-3-fluorophenyl)-5-(tetrazol-2-ylmethyl)oxazolidin-2-one 1-Chloroethyl chloroformate (1.18 g, 8.3 mM) was added dropwise, under an atmosphere of nitrogen, to a stirred solution of (5R)-3-(4-(1-benzyl-1,2,5,6-tetrahydropyridin-4-yl)-3-fluoro-phenyl)-5-(tetrazol-2-ylmethyl)oxazolidin-2-one (2.56 g, 5.90 mM) and N,N-diisopropylethylamine (0.230 mg, 1.77 mM) in dichloromethane (50 ml) with cooling in ice/water. The reaction was stirred for 30 minutes at ice temperature, and the brown solution purified by MPLC on silica, eluting with 75% ethyl acetate in isohexane. The resulting carbamate intermediate was dissolved in methanol (60 ml) and heated at 60° for 30 minutes. Evaporation of the solvent and trituration with diethyl ether gave the title compound (1.76 g) as its hydrochloride salt. MS (ESP): 345 (MH$^+$) for $C_{16}H_{17}FN_6O_2$
  NMR (DMSO-d$_6$) δ: 2.65 (s, 2H); 3.28 (t, 2H); 3.72 (d, 2H); 3.92 (dd, 1H); 4.30 (t, 1H); 5.11–5.32 (m, 3H); 6.03 (m, 1H); 7.28 (m, 1H); 7.38–7.50 (m, 2H); 9.05 (s, 1H); 9.30 (br s; 2H).

EXAMPLE 71

(5R)-3-(4-(1-((4S)-2,2-Dimethyl-1,3-dioxolane-4-carbonyl)-1,2,5,6-tetrahydropyridin-4-yl)-3-fluorophenyl)-5-(tetrazol-2-ylmethyl)oxazolidin-2-one (4S)-2,2-Dimethyl-1,3-dioxolane-4-carbonyl chloride (350 mg, 2.10 mM) was added dropwise to a stirred suspension of (5R)-3-(4-(1,2,5,6-tetrahydropyridin-4-yl)-3-fluoro-phenyl)-5-(tetrazol-2-ylmethyl)oxazolidin-2-one hydrochloride (500 mg, 1.31 mM) and pyridine (0.52 g, 6.57 mM) in dichloromethane (20 ml) with ice/water cooling. The reaction was allowed to warm to room temperature and stirred 1 hour. The resulting solution was washed with water and saturated brine, dried (magnesium sulfate) and evaporated to a small volume. Addition of diethyl ether gave the title compound (600 mg) as a yellow solid.
  MS (ESP): 473 (MH$^+$) for $C_{22}H_{25}FN_6O_5$
  NMR (DMSO-d$_6$) δ: 1.30–1.38 (m, 6H); 2.43 (partly obscured by DMSO, 2H); 3.61–3.80 (m, 2H); 3.94 (dd, 1H); 4.06–4.33 (m, 5H); 4.90 (m, 1H); 5.10–5.31 (m, 3H); 6.01 (m, 1H); 7.24 (m, 1H); 7.35–7.48 (m, 2H); 9.04 (s, 1H).

EXAMPLE 72

(5R)-3-(4-(1-(2-Acetoxyacetyl)-1,2,5,6-tetrahydropyridin-4-yl)-3-fluoro-phenyl)-5-(tetrazol-2-ylmethyl)oxazolidin-2-one Acetoxyacetyl choride (0.356 mg, 2.63 mM) was added dropwise to a stirred solution of (5R)-3-(4-(1,2,5,6-tetrahydropyridin-4-yl)-3-fluorophenyl)-5-(tetrazol-2-ylmethyl) oxazolidin-2-one hydrochloride (500 mg, 1.31 mM) and sodium hydrogen carbonate (1.10 g, 13.1 mM) in a mixture of water (10 ml) and acetone (20 ml) with ice/water cooling. The reaction was allowed to warm- to room temperature and stirred 16 hours, then diluted with water (80 ml) and extracted with ethyl acetate (3×80 ml). The combined extracts were washed with saturated brine, dried (magnesium sulfate) and evaporated to a yellow oil. Trituration with diethyl ether gave the title compound as a yellow solid (390 mg).
  MS (ESP): 445 (MH$^+$) for $C_{20}H_{21}FN_6O_5$
  NMR (DMSO-d$_6$) δ: 2.10 (s, 3H); 2.42 (partly obscured by DMSO, 2H); 3.51–3.68 (m, 2H); 3.94 (dd, 1H); 4.09 (m, 2H); 4.29 (t, 1H); 4.82 (m, 2H); 5.10–5.30 (m, 3H); 6.00 (m, 1H); 7.24 (m, 1H); 7.35–7.49 (m, 2H); 9.02 (s, 1H).

EXAMPLE 73

(5R)-3-(4-(1-((2S)-2,3-Dihydroxypropionyl)-1,2,5,6-tetrahydropyridin-4-yl)-3-fluorophenyl)-5-(tetrazol-2-ylmethyl)oxazolidin-2-one (5R)-3-(4-(1-((4S)-2,2-Dimethyl-1,3-dioxolane-4-carbonyl)-1,2,5,6-tetrahydropyridin-4-yl)-3-fluorophenyl)-5-(tetrazol-2-ylmethyl)oxazolidin-2-one (550 mg, 1.17 mM) in a mixture of tetrahydrofuran (25 ml) and aqueous hydrochloric acid (1M, 10 ml) was stirred at room temperature for 24 hours, then concentrated by evaporation to a solid. The solid was filtered, washed with water, followed by a small volume of ethanol, then triturated with diethyl ether to give the title compound as a colourless solid (450 mg).
  MS (ESP): 433 (MH$^+$) for $C_{19}H_{21}FN_6O_5$
  NMR (DMSO-d$_6$) δ: 2.41 (partly obscured by DMSO, 2H); 3.41–4.42 (m, 1H); 5.11–5.32 (m, 3H); 6.01 (m, 1H); 7.25 (m, 1H); 7.35–7.48 (m, 2H); 9.04 (s, 1H).

EXAMPLE 74

(5R)-3-(4-(1-(2-Hydroxyacetyl)-1,2,5,6-tetrahydropyridin-4-yl)-3-fluoro-phenyl)-5-(tetrazol-2-ylmethyl)oxazolidin-2-one (5R)-3-(4-(1-(2-Acetoxyacetyl)-1,2,5,6-tetrahydropyridin-4-yl)-3-fluorophenyl)-5-(tetrazol-2-ylmethyl)oxazolidin-2-one (365 mg, 0.82 mM) was treated with a saturated solution of ammonia in methanol (40 ml), warmed slightly to dissolve completely, then stirred at room temperature for 20 hours. The solvent was evaporated to give an orange oil which was triturated with diethyl ether to give the title compound as a pale yellow solid (211 mg).
  MS (ESP): 403 (MH$^+$) for $C_{18}H_{19}FN_6O_4$
  NMR (DMSO-d$_6$) δ: 2.45 (partly obscured by DMSO, 2H); 3.50–3.70 (m, 2H); 3.92 (dd, 1H); 4.03–4.19 (m, 4H); 4.30 (t, 1H); 4.55–4.65 (m, 1H); 5.10–5.31 (m, 3H); 5.95–6.04 (m, 1H); 7.23 (m, 1H); 7.34–7.48 (m, 2H); 9.04 (s, 1H).

EXAMPLE 75

(5R)-3-(3,5-Difluoro-4-(3,6-dihydro-1,1-dioxo-2H-thiopyran-4-yl)phenyl)-5-(tetrazol-1-ylmethyl)oxazolidin-2-one and (5R)-3-(3,5-Difluoro-4-(3,6-dihydro-1,1-dioxo-2H-thiopyran-4-yl)phenyl)-5-(tetrazol-2-ylmethyl)oxazolidin-2-one (5R)-3-(3,5-Difluoro-4-(2,6-dihydro-1,1-dioxo-2H-thiopyran-4-yl)phenyl)-5-methane-sulfonyloxymethyloxazolidin-2-one (437 mg, 1 mM), was treated with 1H-tetrazole (105 mg, 1.5 mM) essentially as in Example 34 except that the mixture was heated to 75° for 2 hours. Crude product after the ethyl acetate extraction was purified by chromatography on a 10 g silica Mega Bond Elut® column, eluting with a gradient increasing in polarity from 0 to 100% ethyl acetate in dichloromethane. Relevant fractions of the first eluting product were combined to give the less polar tetrazol-2-yl isomer (206 mg).

MS (ESP): 412 (MH$^+$) for $C_{16}H_{15}F_2N_5O_4S$

NMR (DMSO-d$_6$) δ: 2.82 (m, ~2H); 3.32 (m overlapped by H$_2$O, 2H); 3.93 (overlapping m, 3H); 4.28 (t, 1H); 5.15 (d, 1H); 5.24 (d, 1H); 5.30 (m, 1H); 5.75 (br s, 1H); 7.31 (d, 2H); 9.03 (s, 1H).

The second eluting product was the 1-isomer (105 mg).

MS (ESP): 412 (MH$^+$) for $C_{16}H_{15}F_2N_5O_4S$

NMR (DMSO-d$_6$) δ: 2.81 (m, 2H); 3.33 (m overlapped by H$_2$O, ~2H); 3.92 (overlapping m, 3H); 4.26 (t, 1H); 4.93 (d, 2H); 5.18 (m, 1H); 5.74 (s, 1H); 7.31 (d, 2H); 9.48 (s, 1H).

EXAMPLE 76

(5R)-3-(4-(1-Isopropylsulfonyl-1,2,5,6-tetrahydropyridin-4-yl)-3-fluoro-phenyl)-5-(1,2,3-triazol-1-ylmethyl)oxazolidin-2-one (5R)-3-(4-(1,2,5,6-Tetrahydropyridin-4-yl)-3-fluorophenyl)-5-(1,2,3-triazol-1-ylmethyl)-oxazolidin-2-one hydrochloride (380 mg, 1 mM) was dissolved in water (5 ml), which was then diluted with acetone (10 ml), and solid sodium bicarbonate (0.84 g, 10 mM) added. The mixture was stirred and cooled to 0° C., and isopropylsulfonyl chloride (285 mg, 2 mM) added dropwise. After stirring for 5 hours, an equal portion of sulfonyl chloride was added, and stirring continued for 18 hours. Most acetone was removed by evaporation, the residue diluted with water (50 ml), and extracted with ethyl acetate (3×20 ml). The extracts were washed with brine and dried (magnesium sulfate). The residual oil after evaporation was purified by chromatography on a 10 g silica Mega Bond Elut® column, eluting with a gradient increasing in polarity from 0 to 5% methanol in dichloromethane. Relevant fractions were combined and evaporated to give the desired product (205 mg).

MS (ESP): 450 (MH$^+$) for $C_{20}H_{24}FN_5O_4S$

NMR (CDCl$_3$) δ: 1.37 (d, 6H); 2.53 (br, 2H); 3.22 (heptet, 1H); 3.56 (td, 2H); 3.94 (dd, 1H); 4.03 (m, 2H); 4.16 (t, 1H); 4.78 (d, 2H); 5.06 (m, 1H); 5.92 (m, 1H); 7.07 (dd, 1H); 7.19 (td, 1H); 7.29 (dd, 1H); 7.74 (d, 1H); 7.78 (d, 1H).

EXAMPLE 77

(5R)-3-(4-(1-Methylsulfonyl-1,2,5,6-tetrahydropyridin-4-yl)-3-fluoro-phenyl)-5-(1,2,3-triazol-1-ylmethyl)oxazolidin-2-one (5R)-3-(4-(1,2,5,6-Tetrahydropyridin-4-yl)-3-fluorophenyl)-5-(1,2,3-triazol-1-ylmethyl)-oxazolidin-2-one hydrochloride (380 mg, 1 mM) was suspended in dichloromethane (15 ml), 4-dimethylaminopyridine (305 mg, 2.5 mM) added, and the mixture stirred vigorously for 15 minutes. After cooling to 0° C. under nitrogen, methanesulfonyl chloride (229 mg, 2 mM) was added dropwise, and the mixture stirred 18 hours at ambient temperature. Precipitated solid was removed, and the organic solution concentrated, then purified by chromatography on a 10 g silica Mega Bond Elut® column, eluting with a gradient increasing in polarity from 0 to 5% methanol in dichloromethane. Relevant fractions were combined and evaporated to give the desired product (30 mg). MS (ESP): 422 (MH$^+$) for $C_{18}H_{20}FN_5O_4S$ NMR (DMSO-d$_6$) δ: 2.52 (br, 2H); 2.92 (s, 3H); 3.34 (t, 2H); 3.84 (m, 2H); 3.89 (dd, 1H); 4.23 (t, 1H); 4.82 (d, 2H); 6.01 (br, 1H); 7.23 (dd, 1H); 7.36 (t, 1H); 7.40 (dd, 1H); 7.74 (d, 1H); 8.14 (d, 1H).

EXAMPLE 78

(5R)-3-(4-(1-Ethylsulfonyl-1,2,5,6-tetrahydropyridin-4-yl)-3-fluorophenyl)-5-(1,2,3-triazol-1-ylmethyl)oxazolidin-2-one (5R)-3-(4-(1,2,5,6-Tetrahydropyridin-4-yl)-3-fluorophenyl)-5-(1,2,3-triazol-1-ylmethyl)-oxazolidin-2-one hydrochloride (380 mg, 1 mM) was), was treated with ethanesulfonyl chloride essentially as in Example 77 to give the desired product (21 mg) after chromatography. MS (ESP): 436 (MH$^+$) for $C_{19}H_{22}FN_5O_4S$ NMR (CDCl$_3$) δ: 1.39 (t, 3H); 2.55 (br, 2H); 3.02 (q, 2H); 3.53 (t, 2H); 3.94 (dd, 1H); 3.99 (m, 2H); 4.16 (t, 1H); 4.78 (d, 2H); 5.06 (m, 1H); 5.92 (br, 1H); 7.06 (dd, 1H); 7.19 (t, 1H); 7.29 (dd, 1H); 7.74 (d, 1H); 7.78 (d, 1H).

EXAMPLE 79

(5R)-3-(4-(1-Trifluoromethylsulfonyl-1,2,5,6-tetrahydropyridin-4-yl)-3-fluorophenyl)-5-(1,2,3-triazol-1-ylmethyl)oxazolidin-2-one (5R)-3-(4-(1,2,5,6-Tetrahydropyridin-4-yl)-3-fluorophenyl)-5-(1,2,3-triazol-1-ylmethyl)-oxazolidin-2-one hydrochloride (380 mg, 1 mM) was treated with trifluoromethanesulfonyl chloride essentially as in Example 76. Crude material was purified by chromatography on a 5 g silica Mega Bond Elut® column, eluting with a gradient increasing in polarity from 0 to 10% methanol in dichloromethane. Relevant fractions were combined and evaporated to give the desired product (444 mg). MS (ESP): 476 (MH$^+$) for $C_{18}H_{17}F_4N_5O_4S$ NMR (DMSO-d$_6$) δ: 2.55 (br, 2H); 3.71 (t, 2H); 3.88 (dd, 1H); 4.16 (m, 2H); 4.23 (t, 1H); 4.81 (d, 2H); 5.13 (m, 1H); 6.02 (br, 1H); 7.24 (dd, 1H); 7.38 (t, 1H); 7.42 (dd, 1H); 7.74 (d, 1H); 8.14 (d, 1H).

EXAMPLE 80

(5R)-3-(4-(1-(3-Chloropropyl)sulfonyl-1,2,5,6-tetrahydropyridin-4-yl)-3-fluorophenyl)-5-(1,2,3-triazol-1-ylmethyl)oxazolidin-2-one (5R)-3-(4-(1,2,5,6-Tetrahydropyridin-4-yl)-3-fluorophenyl)-5-(1,2,3-triazol-1-ylmethyl)-oxazolidin-2-one hydrochloride (380 mg, 1 mM) was treated with 3-chloropropylsulfonyl chloride essentially as in Example 76. After the reaction, the precipitate was filtered, washed with water (10 ml), diethyl ether (2×10 ml), and dried to give the desired product (245 mg).

MS (ESP): 484 (MH$^+$) for $C_{20}H_{23}ClFN_5O_4S$

NMR (DMSO-d$_6$) δ: 2.12 (quintet, 2H); 2.49 (br, obscured by DMSO, ~2H); 3.21 (t, 2H); 3.42 (t, 2H); 3.73 (t, 2H); 3.89 (overlapping m, 3H); 4.23 (t, 1H); 4.82 (d, 2H); 5.13 (m, 1H); 6.01 (br, 1H); 7.23 (dd, 1H); 7.35 (t, 1H); 7.41 (dd, 1H); 7.74 (d, 1H); 8.14 (d, 1H).

EXAMPLE 81

(5R)-3-(4-(1-(2-Methoxyethyl)sulfonyl-1,2,5,6-tetrahydropyridin-4-yl)-3-fluorophenyl)-5-(1,2,3-triazol-1-ylmethyl)oxazolidin-2-one (5R)-3-(4-(1,2,5,6-Tetrahydropyridin-4-yl)-3-fluorophenyl)-5-(1,2,3-triazol-1-ylmethyl)-oxazolidin-2-one hydrochloride (380 mg, 1 mM) was treated with 2-methoxyethylsulfonyl chloride essentially as in Example 79. Chromatography gave the desired product (65 mg).

MS (ESP): 466 (MH$^+$) for $C_{20}H_{24}FN_5O_5S$

NMR (CDCl$_3$) δ: 2.55 (br, 2H); 3.25 (t, 2H); 3.37 (s, 3H); 3.50 (t, 2H); 3.77 (t, 2H); 3.92 (m, 1H); 3.97 (m, 2H); 4.16 (t, 1H); 4.78 (d, 2H); 5.06 (m, 1H); 5.91 (br, 1H); 7.06 (dd, 1H); 7.18 (t, 1H); 7.29 (dd, 1H); 7.74 (d, 1H); 7.78 (d, 1H).

EXAMPLE 82

(5R)-3-[3-Fluoro-4-(1 (R,S)-oxo-3,6-dihydro-2H-thiopyran-4-yl)phenyl]-5-(1,2,3-triazol-1-ylmethyl)oxazolidin-2-one

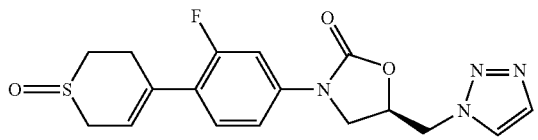

(5R)-3-[4-(3,6-dihydro-2H-thiopyran-4-yl)-3-fluorophenyl]-5-(1,2,3-triazol-1-ylmethyl)oxazolidin-2-one (Example 83; 1.25 g, 3.5 mmol) was stirred in a mixture of methanol and ethyl acetate (1:1, 50 ml) at ambient temperature. Sodium periodate (0.93 g, 4.3 mmol) in water (10 ml) was added dropwise, and it was stirred for 18 hours. Precipitated salts were removed by filtration and solvents were removed under vacuum. The residue was chromatographed on silica gel, washing with 25% acetone in dichloromethane, then eluting with 5 to 7% methanol in dichloromethane to give the title product (1.152 g).

MS (ESP): 377 (MH$^+$) for $C_{17}H_{17}FN_4O_3S$ $^1$H-NMR (DMSO-d$_6$) δ: 2.57 (m, 1H); 2.91 (m, 1H); 2.97 (m, 1H); 3.13 (m, 1H); 3.39 (m, 1H); 3.67 (m, 1H); 3.92 (dd, 1H); 4.27 (dd, 1H); 4.86 (m, 2H); 5.17 (m, 1H); 5.84 (m, 1H); 7.28 (dd, 1H); 7.39 (dd, 1H); 7.45 (dd, 1H); 7.79 (d, 1H); 8.20 (d, 1H).

EXAMPLE 83

(5R)-3-[4-(3,6-dihydro-2H-thiopyran-4-yl)-3-fluorophenyl]-5-(1,2,3-triazol-1-ylmethyl)oxazolidin-2-one

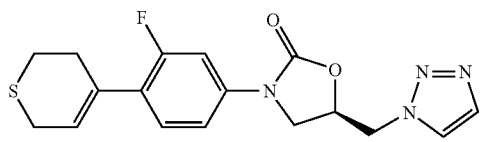

(5R)-3-[4-(3,6-dihydro-2H-thiopyran-4-yl)-3-fluorophenyl]-5-azidomethyloxazolidin-2-one (2 g, 5.7 mmol) was dissolved in dioxane (10 ml). Bicyclo[2.2.1]hepta-2,5-diene (3.1 ml, 28.7 mmol) was added and it was refluxed under nitrogen for 18 hours. The solvent was evaporated in vacuo and the residue subjected to chromatography on silica gel eluting with 25% ethylacetate in dichloromethane to give the title compound (1.51 g).

MS (ESP): 361 (MH$^+$) for $C_{17}H_{17}FN_4O_2S$ $^1$H-NMR (DMSO-d$_6$) δ: 2.56 (m, 2H); 2.83 (dd, 2H); 3.31 (m, 2H); 3.91 (dd, 1H); 4.26 (dd, 1H); 4.86 (m, 2H); 5.17 (m, 1H); 6.06(m, 1H); 7.25 (dd, 1H); 7.33 (dd, 1H); 7.42 (dd, 1H); 7.78 (d, 1H); 8.19 (d, 1H).

The above Examples 82 & 83 were prepared from the intermediates below:

(5R)-3-[4-(3,6-dihydro-2H-thiopyran-4-yl)-3-fluorophenyl]-5-azidomethyloxazolidin-2-one Methanesulfonic acid (5R)-3-[4-(3,6-dihydro-2H-thiopyran-4-yl)-3-fluorophenyl]-2-oxo-oxazolidin-5-ylmethyl ester (8 g, 19.7 mmol) and sodium azide (4 g, 61.5 mmol) were heated in N,N-dimethylformamide (75 ml) at 80° C. for 2 hours. It was cooled to room temperature, diluted with ethyl acetate, washed with potassium phosphate buffer (pH 7) and with water and dried over sodium sulfate. After evaporation of the solvent the title product was obtained as a brown oil (~7 g, crude).

$^1$H-NMR (DMSO-d$_6$) δ: 2.56 (m, 2H); 2.83 (dd, 2H); 3.31 (m, 2H); 3.71 (dd, 1H); 3.80 (dd, 1H); 3.81 (dd, 1H); 4.17 (dd, 1H); 4.92 (m, 1H); 6.06(m, 1H); 7.34 (m, 2H); 7.50 (m, 1H).

Methanesulfonic acid (5R)-3-[4-(3,6-dihydro-2H-thiopyran-4-yl)-3-fluorophenyl]-2-oxo-oxazolidin-5-ylmethyl ester

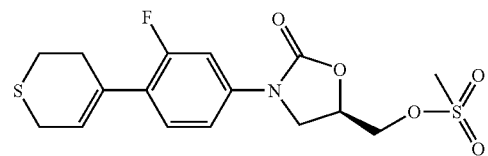

(5R)-3-[4-(3,6-dihydro-2H-thiopyran-4-yl)-3-fluorophenyl]-5-hydroxymethyloxazolidin-2-one (14 g, 45.3 mmol) was dissolved in dichloromethane (300 ml) and triethylamine (8.8 ml, 63.3 mmol) was added. It was cooled to −20° C. and methanesulfonyl chloride (4.22 ml, 54.4 mmol), dissolved in dichloromethane (50 ml), was added dropwise. The reaction mixture was allowed to warm to room temperature and was quenched with potassium phosphate buffer (pH 7). Dichloromethane was removed under vacuum and it was extracted with ethyl acetate, washed with water and dried over magnesium sulfate. The title compound (16.9 g) was precipitated from dichloromethane by addition of hexane.

$^1$H-NMR (DMSO-d$_6$) δ: 2.56 (m, 2H); 2.83 (dd, 2H); 3.28 (s, 3H); 3.32 (m, 2H); 3.85 (dd, 1H); 4.21 (dd, 1H); 4.48 (dd, 1H); 4.53 (dd, 1H); 5.04 (m, 1H); 6.07 (m, 1H); 7.33 (dd, 1H); 7.36 (dd, 1H); 7.50 (dd, 1H).

(5R)-3-[4-(3,6-dihydro-2H-thiopyran-4-yl)-3-fluorophenyl]-5-hydroxymethyloxazolidin-2-one 4-(2-Fluoro-4-benzyloxycarbonylaminophenyl)-3,6-dihydro-2H-thiopyran (15.3 g, 44.6 mM) was dissolved in dry tetrahydrofuran (175 ml) and stirred under nitrogen at −70° C. n-Butyllithium (1.6M in hexanes, 30 ml, 175 mM) was run in over 20 minutes, keeping the temperature below −60°, and the mixture then stirred a further 10 minutes at −70° C. A solution of (R)-glycidyl butyrate (6.42 g, 44.62 mM) dissolved in dry tetrahydrofuran (10 ml) was added dropwise over 10 minutes keeping temperature below −60°, and the mixture left to warm to ambient temperature over 18 hours. Methanol (29 ml) was added, and the mixture stirred for 10 minutes only. Saturated aqueous sodium bicarbonate (200 ml) was added, and the mixture extracted with ethyl acetate (400 ml). The extract was washed with saturated aqueous sodium bicarbonate (100 ml), brine (100 ml), dried (magnesium sulfate). Filtered and evaporated. The crude product was purified on a 300 g silica sinter column, eluting with a gradient from 0% to 100% ethyl acetate in dichloromethane. Relevant fractions were combined, reduced to a small volume, and diluted with an excess of isohexane to precipitate the desired product (11.3 g). MS (ESP): 310 (MH$^+$) for $C_{15}H_{16}FNO_3S$ NMR (DMSO-d$_6$) δ: 2.52 (m overlapped by DMSO, 2H); 2.78 (t, 2H); 3.27 (m, 2H); 3.52 (m, 1H); 3.65 (m, 1H); 3.80 (dd, 1H); 4.06 (dd, 1H); 4.65 (m, 1H); 5.19 (t, 1H); 6.01 (s, 1H); 7.28 (m, 2H); 7.47 (dd, 1H).

4-(2-Fluoro-4-benzyloxycarbonylaminophenyl)-3,6-dihydro-2H-thiopyran

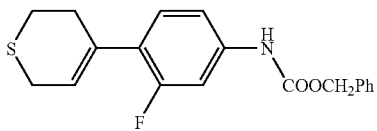

4-(2-Fluoro-4-aminophenyl)-3,6-dihydro-2H-thiopyran (9.8 g, 46.8 mM) was dissolved in dry dichloromethane (196 ml), pyridine (6.23 g, 79.1 mM) added, and the mixture stirred under nitrogen at −20°. A solution of benzyl chloroformate (9.54 g, 53.9 mM) dissolved in dry dichloromethane (25 ml) was added dropwise, and the mixture left to warm to ambient temperature over 18 hours. The mixture was washed with 1M hydrochloric acid (200 ml), then brine (100 ml), dried (magnesium sulfate), filtered and evaporated to a small volume. The addition of isohexane (300 ml) precipitated the desired product (15.5 g).

MS (Negative ESP): 342 (M—H—) for $C_{19}H_{18}FNO_2S$
NMR (DMSO-d$_6$) δ: 2.50 (s, 2H); 2.79 (t, 2H); 3.26 (m, 2H); 5.15 (s, 2H); 5.99 (s, 1H); 7.18 (m, 2H); 7.38 (m, 6H); 10.01 (s, 1H).

4-(2-Fluoro-4-aminophenyl)-3,6-dihydro-2H-thiopyran

4-Hydroxy-4-(2-fluoro-4-aminophenyl)tetrahydrothiopyran (11.35 g, 50 mM) and butylated hydroxytoluene (50 mg) as antioxidant were suspended in a mixture of concentrated hydrochloric acid (37%, 200 ml) and water (50 ml), and stirred at 80° under nitrogen for 18 hours. Glacial acetic acid (150 ml) was added, and reaction continued at 80° for a further 5 hours. After cooling, the reaction was made basic by the cautious addition of concentrated ammonia and ice. The mixture was extracted with diethyl ether (400 ml), the extract washed with water (100 ml), brine (100 ml), dried (magnesium sulfate), filtered and evaporated to give the title product (10 g) as a dark oil.

NMR (CDCl$_3$) δ: 2.59 (m, 2H); 2.72 (t, 2H); 3.30 (m, 2H); 3.80 (br, 2H); 5.93 (m, 1H); 6.35 (dd, 1H); 6.39 (dd, 1H); 6.97 (t, 1H).

EXAMPLE 84

(5R)-3-[4-(1,1-dioxo-3,6-dihydro-2H-thiopyran-4-yl)-3-fluorophenyl]-5-(1,2,3-triazol-1-ylmethyl)oxazolidin-2-one

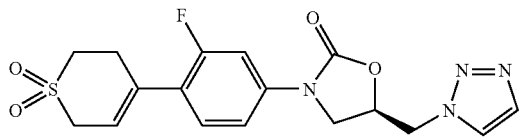

(5R)-3-[4-(3,6-dihydro-2H-thiopyran-4-yl)-3-fluorophenyl]-5-(1,2,3-triazol-1-ylmethyl)oxazolidin-2-one (250 mg, 0.7 mmol) was dissolved in dichloromethane (10 ml). Metachloroperbenzoic acid (~70%, 0.54 g, ~2.2 mmol), dissolved in dichloromethane (5 ml) was added dropwise under ice-cooling. It was allowed to warm to room temperature and stirred for 2 hours. The reaction mixture was diluted with ethylacetate, washed with 5% aqueous sodium thiosulfate solution, saturated aqueous sodiumhydrogen carbonate solution and with water. It was dried over sodium sulfate and the solvent evaporated under vacuum. The residue was chromatographed on silica gel, eluting with 3% methanol in dichloromethane to give the title product (197 mg). MS (ESP): 393 (MH$^+$) for $C_{17}H_{17}FN_4O_4S$ $^1$H-NMR (DMSO-d$_6$) δ: 2.97 (m, 2H); 3.36 (m, 2H); 3.93 (m, 3H); 4.27 (dd, 1H); 4.86 (m, 2H); 5.18 (m, 1H); 5.83 (m, 1H); 7.29 (dd, 1H); 7.40 (dd, 1H); 7.47 (dd, 1H); 7.78 (s, 1H); 8.19 (s, 1H).

EXAMPLE 85

(5R)-3-[3,5-Difluoro-4-(1(R,S)-oxo-3,6-dihydro-2H-thiopyran-4-yl)-phenyl]-5-(1,2,3-triazol-1-ylmethyl)oxazolidin-2-one

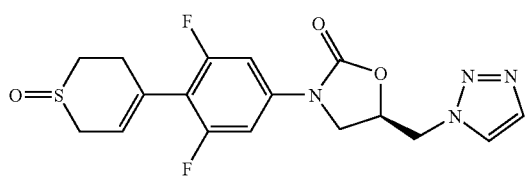

(5R)-3-[4-(3,6-dihydro-2H-thiopyran-4-yl)-3,5-difluorophenyl]-5-(1,2,3-triazol-1-ylmethyl)oxazolidin-2-one (Example 86; 0.86 g, 2.3 mmol) was stirred in a mixture of methanol and ethyl acetate (1:1, 20 ml) at ambient temperature. Sodium periodate (0.50 g, 2.4 mmol) in water (10 ml) was added dropwise, and the mixture stirred for 3 hours. Precipitated salts were removed by filtration and washed with ethyl acetate. The filtrate was washed with brine, dried over magnesium sulfate and concentrated to dryness. The residue was chromatographed on silica gel eluting with 5% methanol in dichloromethane to give the title product (0.69 g). MS (ESP): 395 (MH$^+$) for $C_{17}H_{16}F_2N_4O_3S$ $^1$H-NMR (DMSO-d$_6$) δ: 2.41 (brs, 1H); 2.80 (m, 1H); 2.97 (brs, 1H); 3.15 (m, 1H); 3.39 (m, 1H); 3.67 (brs, 1H);

3.94 (m, 1H); 4.25 (dd, 1H); 4.85 (brs, 2H); 5.19 (m, 1H); 5.75 (brs, 1H); 7.33 (d, 2H); 7.79 (brs, 1H); 8.20 (brs, 1H).

EXAMPLE 86

(5R)-3-[4-(3,6-Dihydro-2H-thiopyran-4-yl)-3,5-difluorophenyl-5-(1,2,3-triazol-1-ylmethyl)oxazolidin-2-one Methanesulfonic acid (5R)-3-[4-(3,6-dihydro-2H-thiopyran-4-yl)-3,5-difluorophenyl]-2-oxo-oxazolidin-5-ylmethyl ester (1.1 g, 5.7 mmol) was dissolved in dry N,N-dimethylformamide (5 ml) and sodium azide (0.35 g, 5.43 mmol) was added. It was heated at 60° C. for 18 hours. The reaction mixture was cooled to room temperature, diluted with ethylacetate, washed with water and dried over magnesium sulfate. Solvent was removed under vacuum to give an oil. The crude intermediate azide was not characterized. It was taken up in 1,4-dioxane (20 ml), bicyclo[2.2.1]hepta-2,5-diene (1.0 g, 10.9 mmol) was added and it was refluxed for 12 hours. Solvent was removed under vacuum and the residue chromatographed on silica gel with 5% methanol in dichloromethane to give the title compound (0.62 g).

MS (ESP): 379 (MH$^+$) for $C_{17}H_{16}F_2N_4O_2S$

NMR (DMSO-d$_6$) δ: 2.43 (brs, 2H); 2.83 (dd, 2H); 3.31 (brs, 2H); 3.92 (m, 1H); 4.25 (dd, 1H); 4.84 (d, 2H); 5.18 (m, 1H); 5.98 (brs, 1H); 7.28 (d, 2H); 7.79 (brs, 1H); 8.19 (brs, 1H).

The above Examples 85 & 86 were prepared from the intermediates prepared analagously to those used in Examples 82 & 83.

EXAMPLE 87

(5R)-3-[3,5-Difluoro-4-(1 (R,S)-oxo-3,6-dihydro-2H-thiopyran-4-yl)-phenyl]-5-(1,2,3-triazol-2-ylmethyl)oxazolidin-2-one

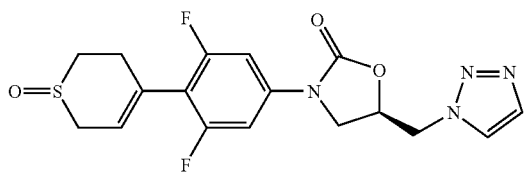

(5R)-3-[4-(3,6-dihydro-2H-thiopyran-4-yl)-3,5-difluorophenyl]-5-(1,2,3-triazol-2-ylmethyl)oxazolidin-2-one (Example 88; 0.48 g, 1.3 mmol) was stirred in a mixture of methanol and ethyl acetate (1:1, 20 ml) at ambient temperature. Sodium periodate (0.28 g, 1.4 mmol) in water (10 ml) was added dropwise, and the mixture stirred for 3 hours. Precipitated salts were removed by filtration and washed with ethyl acetate. The filtrate was washed with brine, dried over magnesium sulfate and concentrated to dryness. Crystallisation from dichloromethane gave the title compound (0.38 g). MS (ESP): 395 (MH$^+$) for $C_{17}H_{16}F_2N_4O_3S$ $^1$H-NMR (DMSO-d$_6$) δ: 2.41 (brs, 1H); 2.83 (m, 1H); 2.97 (m, 1H); 3.11 (m, 1H); 3.41 (m, 1H); 3.67 (brs, 1H); 3.93 (m, 1H); 4.26 (dd, 1H); 4.88 (m, 2H); 5.24 (m, 1H); 5.76 (brd, 1H); 7.31 (d, 2H); 7.86 (s, 2H).

EXAMPLE 88

(5R)-3-[4-(3,6-dihydro-2H-thiopyran-4-yl)-3,5-difluorophenyl]-5-(1,2,3-triazol-2-ylmethyl)oxazolidin-2-one

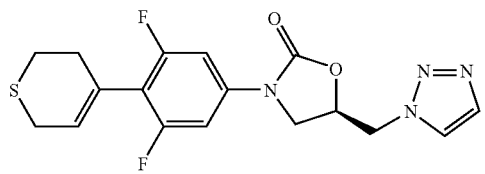

Sodium hydride (60% in oil, 148 mg, 3.7 mmol) was suspended in dry N,N-dimethylformamide (5 ml) and 1,2,3-triazole (0.26 g, 3.7 mmol) was added under nitrogen. It was stirred for 5 minutes at room temperature and methanesulfonic acid (5R)-3-[4-(3,6-dihydro-2H-thiopyran-4-yl)-3,5-difluorophenyl]-2-oxo-oxazolidin-5-ylmethyl ester (see Example 86; 1.0 g, 2.47 mmol) was added. It was heated to 75° C. for 3.5 hours, then cooled to room temperature, diluted with aqueous sodium hydrogencarbonate solution (5%, 100 ml) and extracted with ethylacetate (2×100 ml). The organic phase was washed with water (2×50 ml), brine (100 ml), dried over magnesium sulfate and the solvent was evaporated in vacuo. Chromatography on silica gel with a gradient of 10–50% ethylacetate in hexanes gave the title compound (0.65 g). MS (ESP): 379. (MH$^+$) for $C_{17}H_{16}F_2N_4O_2S$ NMR (CDCl$_3$) δ: 2.53 (m, 2H); 2.89 (dd, 2H); 3.35 (m, 2H); 3.95 (m, 1H); 4.25 (dd, 1H); 4.83 (m, 2H); 5.09 (m, 1H); 5.96 (brs, 1H); 7.05 (d, 2H); 7.79 (d, 2H).

EXAMPLE 89

5(R)-(3-Oxo-isoxazol-2-ylmethyl)-3-(4-(1,2,5,6-tetrahydropyrid-4-yl)-3,5-difluorophenyl)oxazolidin-2-one PCT Application No. GB99/01753 (Publication No. WO 99/64417) describes the preparation of 5(R)-Hydroxymethyl-3-(4-(1-benzyl-1,2,5,6-tetrahydropyrid-4-yl)-3,5-difluorophenyl)oxazolidin-2-one (Reference Example 4 of GB99/01753), which is reacted under Mitsunobu conditions with 3-hydroxyisoxazole to give 5(R)-Isoxazol-3-yloxymethyl-3-(4-(1-benzyl-1,2,5,6-tetrahydropyrid-4-yl)-3,5-difluorophenyl)oxazolidin-2-one (Reference Example 5 of GB99/01753). Purification (by column chromatography) and subsequent reaction with 1-chloroethyl chloroformate and work-up gives 5(R)-Isoxazol-3-yloxymethyl-3-(4-(1,2,5,6-tetrahydropyrid-4-yl)-3,5-difluorophenyl)oxazolidin-2-one (Reference Example 6 of GB99/01753).

During the Mitsunobu reaction the ambident nucleophile 3-hydroxyisoxazole reacts with 5(R)-Hydroxymethyl-3-(4-(1-benzyl-1,2,5,6-tetrahydropyrid-4-yl)-3,5-difluorophenyl) oxazolidin-2-one to give a quantity of 5(R)-(3-Oxo-isoxazol-2-ylmethyl)-3-(4-(1-benzyl-1,2,5,6-tetrahydropyrid-4-yl)-3,5-difluorophenyl)oxazolidin-2-one. Failure to purify (e.g. by suitable column chromatography) the product from the Mitsunobu reaction described in GB99/01753 before subsequent reaction with 1-chloroethyl chloroformate and work-up using hydrochloric acid gives a quantity of 5(R)-(3-Oxo-isoxazol-2-ylmethyl)-3-(4-(1,2,5,6-tetrahydropyrid-4-yl)-3,5-difluorophenyl)oxazolidin-2-one as the hydrochloride salt, which is identified in the mixture by correlation TOCSY NMR (TOtal Correlation SpectroscopY)— methylene carbon attached to the nitrogen of the isoxazolone ring has a shift of 48 ppm (characteristic of this linkage), and by LC-MS (MH+ 378-less chloride) using C-18 Hichrom RPB column, 5 mm, 25 cm×0.46 mm i.d; Eluant—650 ml Water, 350 ml Acetonitrile, 1 ml TFA (biograde); Flow—1.5 ml/min; Retention Times N-linked-Piperidene—Rt=2.0 min, O-linked Piperidene—Rt=3.25 min.

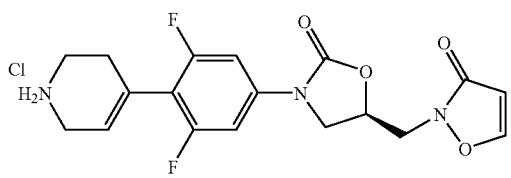

EXAMPLE 90

5(R)-(3-Oxo-isoxazol-2-ylmethyl)-3-(4-(1-(3-tert-butoxy-2(S)-hydroxypropanoyl)-1,2,5,6-tetrahydropyrid-4-yl)-3,5-difluorophenyl)oxazolidin-2-one

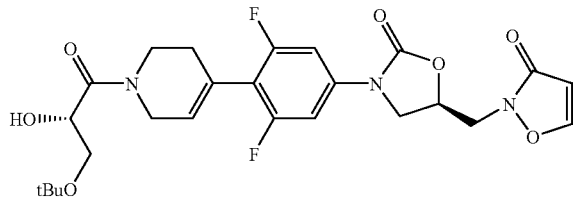

To 3-tert-butoxy-2(S)-hydroxypropanoic acid (343 mmol) in dimethylformamide (DMF) at 20–25° C. was added (4-(1,2,5,6-tetrahydropyrid-4-yl)-3,5-difluorophenyl)oxazolidin-2-one hydrochloride salt (264 mmol; Reference Example 6 of GB99/01753, prepared as described in Example 89 without purification following the Mitsunobu reaction of 3-hydroxyisoxazole reacts with 5(R)-Hydroxymethyl-3-(4-(1-benzyl-1,2,5,6-tetrahydropyrid-4-yl)-3,5-difluorophenyl)oxazolidin-2-one). To the mixture was added 1-hydroxybenzotriazole hydrate (HOBt; 0.4 eq.) and further DMF (to 6 vol.). The solution was placed under a nitrogen atmosphere, cooled to 16–18° C. and Et₃N (1.5 eq.) added. 1-[3-(Dimethylamino)propyl]-3-ethylcarbodiimide hydrochloride (EDCl; 1.4 eq.) dissolved in water (1.5 vol.) was added dropwise keeping the temperature below 25° C. After approximately one hour the reaction was complete and tert-butyl methylether (MTBE; 1 vol.) followed by water (12 vol.) was added. After vigorous stirring for 1 hour the resultant solid was filtered, washed with water and MTBE, and dried under vacuum at 35–40° C.

The resultant product (3.71 kg) was dissolved in DCM (8.5 liters) and purified by column chromatography eluting with EtOAc/iso-hexane (80:20) collecting the appropriate fractions and removing the solvent under reduced pressure to give 5(R)-Isoxazol-3-yloxymethyl-3-(4-(1-(3-tert-butoxy-2(S)-hydroxypropanoyl)-1,2,5,6-tetrahydropyrid-4-yl)-3,5-difluorophenyl)oxazolidin-2-one as a white foam (3.03 kg, 82% yield). The column was eluted further with methanol (50.5 liters) and the solvent removed under reduced pressure to give a brown gum (100 g). Trituration of the gum with EtOAc (500 ml) gave the title compound as a dark yellow solid (100 g).

IR (KBr disk) (cm⁻¹) 1737 (C=O, oxazolidinone), 1638 (C=O, amide); MS (MH+) 522; ¹H NMR (500 MHz) assigned via TOCSY and HMQC (Heteronuclear Multiple Quantum Coherence spectra—A 1H/13C correlation)—methylene carbon attached to the nitrogen of the isoxazolone ring has a shift of 49 ppm (characteristic of this linkage).

EXAMPLE 91

5(R)-(3-Oxo-isoxazol-2-ylmethyl)-3-(4-(1-(2(S), 3-dihydroxypropanoyl)-1,2,5,6-tetrahydropyrid-4-yl)-3,5-difluorophenyl)oxazolidin-2-one

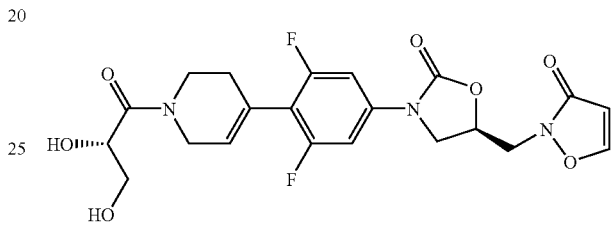

Example 90 (5.0 g) was slurried in 4M HCl in dioxane (25 ml) and stirred at ambient temperature for 24 hours. The gum that formed was washed with dioxane (20 ml) and triturated with isobutanol (50 ml). The solid that resulted was washed with isobutanol (2×10 ml) and dried under reduced pressure to give the title compound as a yellow solid (3.4 g).

¹H NMR (500 MHz) assigned via TOCSY and HMQC correlation spectra. Methylene carbon attached to the nitrogen of the isoxazolone ring has a shift of 47 ppm (characteristic of this linkage vs O-linkage); MS (MH+) 466.

EXAMPLE 92

The following illustrate representative pharmaceutical dosage forms containing a compound of the formula (I), an in-vivo hydrolysable ester or a pharmaceutically-acceptable salt thereof, including a pharmaceutically-acceptable salt of an in-vivo hydrolysable ester, (hereafter compound X), for therapeutic or prophylactic use in humans:

| (a) | Tablet I | mg/tablet |
|---|---|---|
| | Compound X | 500 |
| | Lactose Ph.Eur | 430 |
| | Croscarmellose sodium | 40 |
| | Polyvinylpyrrolidone | 20 |
| | Magnesium stearate | 10 |
| (b) | Tablet II | mg/tablet |
| | Compound X | 100 |
| | Lactose Ph.Eur | 179 |
| | Croscarmellose sodium | 12 |
| | Polyvinylpyrrolidone | 6 |
| | Magnesium stearate | 3 |

-continued (c) Tablet III — mg/tablet

| | |
|---|---|
| Compound X | 50 |
| Lactose Ph.Eur | 229 |
| Croscarmellose sodium | 12 |
| Polyvinylpyrrolidone | 6 |
| Magnesium stearate | 3 |

(d) Tablet IV — mg/tablet

| | |
|---|---|
| Compound X | 1 |
| Lactose Ph.Eur | 92 |
| Croscarmellose sodium | 4 |
| Polyvinylpyrrolidone | 2 |
| Magnesium stearate | 1 |

(e) Capsule — mg/capsule

| | |
|---|---|
| Compound X | 10 |
| Lactose Ph.Eur | 389 |
| Croscarmellose sodium | 100 |
| Magnesium stearate | 1 |

(f) Injection I

| | |
|---|---|
| Compound X | 50% w/v |
| Isotonic aqueous solution | to 100% |

(g) Injection II (e.g. bolus)

| | |
|---|---|
| Compound X | 10% w/v |
| Isotonic aqueous solution | to 100% |

(h) Injection III

| | |
|---|---|
| Compound X | 5% w/v |
| Isotonic aqueous solution | to 100% |

(i) Injection IV (e.2. infusion)

| | |
|---|---|
| Compound X | 1% w/v |
| Isotonic aqueous solution | to 100% |

Buffers, pharmaceutically-acceptable surfactants, oils or cosolvents such as polyethylene glycol, polypropylene glycol, glycerol or ethanol, glidants (such as silicon dioxide) or complexing agents such as a cyclodextrin (for example, hydroxypropyl β-cyclodextrin or sulfobutylether β-cyclodextrin) may be used to aid formulation. Also, improvements in aqueous solubility, if desired, may be achieved, for example, by conjugation of a compound of formula (I) with a phospholipid (such as a (phospho)choline derivative) to form a micellar emulsion.

Note: The above formulations may be obtained by conventional procedures well known in the pharmaceutical art, for example as described in "Remington: The Science & Practice of Pharmacy" Vols. I & II (Ed. A. R. Gennaro (Chairman) et al; Publisher: Mack Publishing Company, Easton, Pa.; 19th Edition —1995) and "Pharmaceutics— The Science of Dosage Form Design" (Ed. M. E. Aulton; Publisher: Churchill Livingstone; first published 1988). The tablets (a)–(d) may be (polymer) coated by conventional means, for example to provide an enteric coating of cellulose acetate phthalate.

The invention claimed is:

1. A compound of the formula (I), or a pharmaceutically-acceptable salt, or an in-vivo-hydrolysable ester thereof,

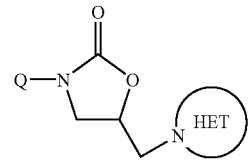

(I)

wherein
HET is an N-linked triazole;
Q is Q1:—

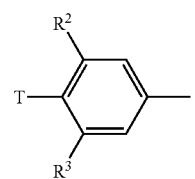

Q1 wherein $R^2$ and $R^3$ are independently hydrogen or fluoro;
wherein T is selected from the groups (TC5) and (TC6);

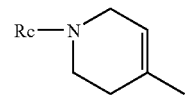

(TC5)

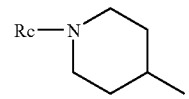

(TC6)

wherein Rc is selected from groups (Rc1) to (Rc5):—
(Rc1) (1–6C)alkyl {optionally monosubstituted by cyano, (1–4C)alkoxy, trifluoromethyl, (1–4C)alkoxycarbonyl, phenyl (optionally substituted as for AR defined hereinafter), (1–4C)alkylS(O)q-(q is 0, 1 or 2); or, on any but the first carbon atom of the (1–6C)alkyl chain, optionally substituted by one or more groups (including geminal distribution) each independently selected from hydroxy and fluoro, and/or optionally monosubstituted by oxo, —NRvRw [wherein Rv is hydrogen or (1–4C) alkyl; Rw is hydrogen or (1–4C)alkyl], (1–6C)alkylS (O)$_p$NH— or (1–4C)alkylS(O)$_p$-((1–4C)alkyl)N-(p is 1 or 2)};
(Rc2) $R^{13}$CO—, $R^{13}$SO$_2$- or $R^{13}$CS—
wherein $R^{13}$ is selected from (Rc2a) to (Rc2e):—
(Rc2a) AR1, AR2, AR2a, AR2b, AR3, AR3a, AR3b, AR4, AR4a, CY1, CY2;
(Rc2b) hydrogen, (1–4C) alkoxycarbonyl, trifluoromethyl, —NRvRw [wherein Rv is hydrogen or (1–4C) alkyl; Rw is hydrogen or (1–4C)alkyl], ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl) ethenyl, 2-((1–4C)alkoxycarbonyl)ethenyl, 2-(AR1) ethenyl, 2-(AR2)ethenyl, 2-(AR2a)ethenyl;

(Rc2C) (1–10C)alkyl
{optionally substituted by one or more groups (including geminal distribution) each independently selected from hydroxy, (1–10C)alkoxy, (1–4C)alkoxy-(1–4C)alkoxy, (1–4C)alkoxy-(1–4C)alkoxy-(1–4C)alkoxy, (1–4C)alkanoyl, phosphoryl [—O—P(O)(OH)$_2$, and mono- and di-(1–4C)alkoxy derivatives thereof], phosphiryl [—O—P(OH)$_2$ and mono- and di-(1–4C)alkoxy derivatives thereof], and amino; and/or optionally substituted by one group selected from phosphonate [phosphono, —P(O)(OH)$_2$, and mono- and di-(1–4C)alkoxy derivatives thereof], phosphinate [-P(OH)$_2$ and mono- and di-(1–4C)alkoxy derivatives thereof], cyano, halo, trifluoromethyl, (1–4C)alkoxycarbonyl, (1–4C)alkoxy-(1–4C)alkoxycarbonyl, (1–4C)alkoxy-(1–4C)alkoxy-(1–4C)alkoxycarbonyl, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminoca rbonyl, (1–4C)alkylS(O)$_p$NH—, (1–4C)alkyl S(O)$_p$-((1–4C)alkyl)N—, fluoro(1–4C)alkylS (O)$_p$NH—, fluoro (1–4C)alkylS(O)$_p$((1–4C)alkyl)N—, (1–4C)alkylS(O)$_q$-[the (1–4C)alkyl group of (1–4C)alkylS(O)$_q$— being optionally substituted by one substituent selected from hydroxy, (1–4C)alkoxy, (1–4C)alkanoyl, phosphoryl (—O—P(O)(OH)$_2$, and mono- and di-(1–4C)alkoxy derivatives thereof], phosphiryl [-O—P(OH)$_2$ and mono- and di-(1–4C)alkoxy derivatives thereof], amino, cyano, halo, trifluoromethyl, (1–4C)alkoxycarbonyl, (1–4C)alkoxy-(1–4C)alkoxycarbonyl (1–4C)alkoxy-(1–4C)alkoxy-(1–4C)alkoxycarbonyl, carboxy, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)$_p$NH—, (1–4C)alkylS(O)$_p$-((1–4C)alkyl)N—, (1–4C)alkylS(O)$_q$—, AR1-S(O)$_q$—, AR2-S(O)$_q$—, AR3-S(O)$_q$— and also AR2a, AR2b, AR3a and AR3b versions of AR2 and AR3 containing groups], CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-AR1-, AR3-NH— (p is 1 or 2 and q is 0, 1 or 2), and also AR2a, AR2b, AR3a and AR3b versions of AR2 and AR3 containing groups};

(Rc2d) R$^{14}$C(O)O(1–6C)alkyl wherein R$^{14}$ is AR1, AR2, (1–4C)alkylamino (the (1–4C)alkyl group being optionally substituted by (1–4C)alkoxycarbonyl or by carboxy), benzyloxy-(1–4C)alkyl or (1–10C)alkyl {optionally substituted as defined for (Rc2c)};

(Rc2e) R$^{15}$O— wherein R$^{15}$ is benzyl, (1–6C)alkyl {optionally substituted as defined for (Rc2c)}, CY1, CY2 or AR2b;

(Rc3) hydrogen, cyano, 2-cyanoethenyl, 2-cyano-2-((1–4C)alkyl)ethenyl, 2-(1–4C)alkylaminocarbonyl)ethenyl), 2-((1–4C)alkoxycarbonyl)ethenyl, 2-nitroethenyl, 2-nitro-2-((1–4C)alkyl)ethenyl, 2-(AR1)ethenyl, 2-(AR2)ethenyl, or of the formula (Rc3a)

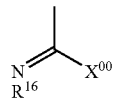

(Rc3a)

wherein X$^{00}$ is —OR$^{17}$, —SR$^{17}$, —NHR$^{17}$ and N(R$^{17}$)$_2$; wherein R$^{17}$ is hydrogen (when X$^{00}$ is —NHR$^{17}$ and —N(R$^{17}$)$_2$), and R$^{17}$ is (1–4C)alkyl, phenyl or AR2 (when X$^{00}$ is —OR$^{17}$, —SR$^{17}$ and —NHR$^{17}$); and R$^{16}$ is cyano, nitro, (1–4C)alkylsulfonyl, (4–7C)cycloalkylsulfonyl, phenylsulfonyl (1–4C)alkanoyl and (1–4C)alkoxycarbonyl;

(Rc4) trityl, AR1, AR2, AR2a, AR2b, AR3, AR3a, AR3b;

(Rc5) RdOC(Re)═CH(C═O)—, RfC(═O)C(═O)—, RgN═C(Rh)C(═O)— or RiNHC(Rj)═CHC(═O)— wherein Rd is (1–6C)alkyl; Re is hydrogen or (1–6C)alkyl, or Rd and Re together form a (3–4C)alkylene chain; Rf is hydrogen, (1–6C)alkyl, hydroxy(1–6C)alkyl, (1–6C)alkoxy(1–6C)alkyl, —NRvRw [wherein Rv is hydrogen or (1–4C)alkyl; Rw is hydrogen or (1–4C)alkyl], (1–6C)alkoxy, (1–6C)alkoxy(1–6C)alkoxy, hydroxy(2–6C)alkoxy, (1–4C)alkylamino (2–6C)alkoxy, di-1–4C)alkylamino(2–6C)alkoxy; Rg is (1–6C)alkyl, hydroxy or (1–6C)alkoxy; Rh is hydrogen or (1–6C)alkyl; R$^1$ is hydrogen, (1–6!)alkyl, AR1, AR2, AR2a, AR2b and Rj is hydrogen or (1–6C)alkyl;

wherein

AR1 is an optionally substituted phenyl or optionally substituted naphthyl;

AR2 is an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;

AR2a is a partially hydrogenated version of AR2 (i.e. AR2 systems retaining some, but not the full, degree of unsaturation), linked via a ring carbon atom or linked via a ring nitrogen atom if the ring is not thereby quaternised;

AR2b is a fully hydrogenated version of AR2 (i.e. AR2 systems having no unsaturation), linked via a ring carbon atom or linked via a ring nitrogen atom;

AR3 is an optionally substituted 8-, 9- or 10-membered, fully unsaturated (i.e with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;

AR3a is a partially hydrogenated version of AR3 (i.e. AR3 systems retaining some, but not the full, degree of unsaturation), linked via a ring carbon atom, or linked via a ring nitrogen atom if the ring is not thereby quaternised, in either of the rings comprising the bicyclic system;

AR3b is a fully hydrogenated version of AR3 (i.e. AR3 systems having no unsaturation), linked via a ring carbon atom, or linked via a ring nitrogen atom, in either of the rings comprising the bicyclic system;

AR4 is an optionally substituted 13- or 14-membered, fully unsaturated (i.e with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;

AR4a is a partially hydrogenated version of AR4 (i.e. AR4 systems retaining some, but not the fall, degree of unsaturation), linked via a ring carbon atom, or linked via a ring nitrogen atom if the ring is not thereby quaternised, in any of the rings comprising the tricyclic system;

CY1 is an optionally substituted cyclobutyl, cyclopentyl or cyclohexyl ring;

CY2 is an optionally substituted cyclopentenyl or cyclohexenyl ring.

2. A compound as claimed in claim 1, or a pharmaceutically-acceptable salt, or an in-vivo-hydrolysable ester thereof; in which the optional substituents in AR are independently selected from halo, (1–4C)alkyl, hydroxy, nitro, carbamoyl, (1–4C)alkylcarbamoyl, di-((1–4C)alkyl)carbamoyl, cyano, trifluoromethyl, trifluoromethoxy, amino, (1–4C)alkylamino, di((1–4C)allyl)amino, (1–4C)alkyl S(O)$_q$ — (q is 0, 1 or 2), carboxy, (1–4C)alkoxycarbonyl, (2–4C)alkenyl, (2–4C)alkynyl, (1–1C)alkanoyl, (1–4C) alkoxy, (1–4C)alkylS(O)$_2$amino, (1–4C)alkanoylamino, benzoylamino, benzoyl, phenyl (optionally substituted by up to three substituents selected from halo, (1–4C)alkoxy or cyano), furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C) alkoxyimino(1–4C)alkyl, hydroxy-(1–4C)alkyl, halo-(1–4C)alkyl, nitro(1–4C)alkyl, amino(1–4C)alkyl, cyano (~1–4C)alkyl, (1–4C)alkanesulfonamido, aminosulfonyl, (1–4C)alkylaminosulfonyl and di-((1–4C)alkyl)aminosulfonyl.

3. A compound as claimed in claim 1, wherein the compound has a structure of the formula (IC), or a pharmaceutically-acceptable salt, or an in-vivo-hydrolysable ester thereof,

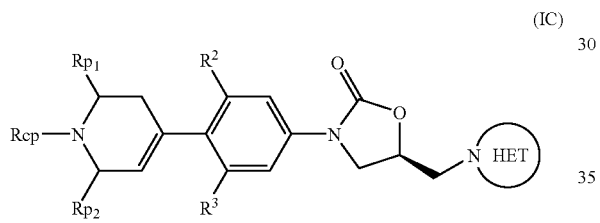

(IC)

wherein HET is an N-linked 5-membered triazole ring, which ring is optionally substituted on a C atom by an oxo or thioxo group; and/or the ring is optionally substituted on a C atom by 1 or 2 (1–4C)alkyl groups; and/or on an available nitrogen atom (provided that the ring is not thereby quaternized) by (1–4C)alkyl;

$R^2$ and $R^3$ are independently hydrogen or fluoro; Rp1 and Rp2 are independently hydrogen, AR-oxymethyl or AR-thiomethyl [wherein AR is phenyl, phenyl-(1–4C) alkyl, naphthyl, furan, pyrrole, pyrazole, imidazole, triazole, pyrimidine, pyridazine, pyridine, isoxazole, oxazole, isothiazole, thiazole or thiophene], (1–4C) alkyl, carboxy, (1–4C)alkoxycarbonyl, hydroxymethyl, (1–4C) alkoxymethyl or carbamoyl and Rcp is cyano, pyrimidin-2-yl, 2-cyanoethenyl, 2-cyano-2-((1–4C) alkyl)ethenyl or Rcp is of the formula $R^{10p}CO$—, $R^{10p}SO_2$- or $R^{10p}CS$— wherein $R^{10p}$ is hydrogen, (1–5C)alkyl [optionally substituted by one or more groups each independently selected from hydroxy and amino, or optionally monosubstituted by (1–4C)alkoxy, (1–4C)alkylS(O)$_q$—, (1–4C)alkylamino, (1–4C)alkanoyl, naphthoxy, (2–6C)alkanoylamino or (1–4C) alkylS(O)$_p$NH— wherein p is 1 or 2 and q is 0, 1 or 2], imidazole, triazole, pyrimidine, pyridazine, pyridine, isoxazole, oxazole, isothiazole, thiazole, pyridoimidazole, pyrimidoimidazole, quinoxaline, quinazoline, phthalazine, cinnoline or naphthyridine, or $R^{10p}$ is of the formula $R^{11p}C(O)O(1-6C)$alkyl wherein $R^{11p}$ is (1–6C)alkyl}, or Rcp is of the formula RfC(=O)C (=O)— wherein Rf is (1–6C)alkoxy.

4. A compound, as claimed in claim 1, selected from the group consisting of
((5R)-3-(4-(1-(2-Hydroxyacetyl)-1,2,5,6-tetrahydropyridin-4-yl)-3,5-difluorophenyl)-5-(1,2,3-triazol-1-ylmethyl)oxazolidin-2-one;
(5R)-3-(4-(1-((2S)-2,3-Dihydroxypropionyl)-1,2,5,6-tetrahydropyridin-4-yl)-3,5-difluorophenyl)-5-(1,2,3-triazol-1-ylmethyl)oxazolidin-2-one;
(5R)-3-(4(1-(2-Hydroxyacetyl)-1,2,5,6-tetrahydropyridin-4-yl-3-fluorophenyl)-5-(1,2,3-triazol-1-ylmethyl) oxazolidin-2-one; and
(5R)-3-(4-(1-((2S)-2,3-Dihydroxypropionyl)-1,2,5,6-tetrahydropyridin-1-yl)-3-fluorophenyl)-5-(1,2,3-triazol-1-ylmethyl)oxazolidin-2-one; or a pharmaceutically-acceptable salt, or an in-vivo-hydrolysable ester thereof.

5. A pharmaceutical composition which comprises a compound as claimed in any one of claims 1, or 3, or a pharmaceutically-acceptable salt or an in-vivo hydrolyzable ester thereof, and a pharmaceutically-acceptable diluent or carrier.

* * * * *